US006114142A

United States Patent [19]
Grieve et al.

[11] Patent Number: 6,114,142
[45] Date of Patent: Sep. 5, 2000

[54] PARASITIC HELMINTH NUCLEIC ACID MOLECULES/AND USES THEREOF

[75] Inventors: Robert B. Grieve, Windsor; Glenn R. Frank, Wellington; Marcia Mika-Grieve, Windsor; Cynthia Ann Tripp, Ft. Collins, all of Colo.

[73] Assignees: Heska Corporation; Colorado State University Research Foundation, both of Ft. Collins, Colo.

[21] Appl. No.: 08/473,034

[22] Filed: Jun. 6, 1995

Related U.S. Application Data

[63] Continuation-in-part of application No. 08/003,389, Jan. 12, 1993, abandoned, application No. 08/101,283, Aug. 3, 1993, abandoned, and application No. PCT/US94/00679, Jan. 12, 1994, said application No. 08/003,389, is a continuation-in-part of application No. 07/654,226, Feb. 12, 1991, abandoned, said application No. 08/101,283, is a continuation of application No. 07/654,226, Feb. 12, 1991, abandoned.

[51] Int. Cl.[7] .......................... C12N 15/11; C12N 15/30; A61K 39/00
[52] U.S. Cl. .................... 435/69.3; 435/69.1; 435/252.3; 435/320.1; 435/172.1; 424/191.1; 424/192.1; 424/265.1; 536/23.1; 536/23.4; 536/23.5; 530/300; 530/350; 530/387.1; 530/388.6; 930/210
[58] Field of Search .................................. 536/23.1, 23.4, 536/23.5; 435/320.1, 252.3, 69.1, 69.3, 172.1; 424/191.1, 192.1, 265.1; 930/210; 530/350, 300, 387.1, 388.6

[56] References Cited

U.S. PATENT DOCUMENTS

| 4,842,999 | 6/1989 | Fuller et al. ................................. 435/7 |
| 5,021,342 | 6/1991 | Green et al. . | |

FOREIGN PATENT DOCUMENTS

| 8776729 | 2/1988 | Australia . |
| 9213560 | 8/1992 | WIPO . |

OTHER PUBLICATIONS

Abraham, et al., "Passive Transfer of Protective Immunity to Larval *Dirofilaria Immitis* from Dogs to Balb/C Mice", pp. 254–257, 1991, *J. Parasitol.*, vol. 77(2)

Abraham, et al., "Genetic Control of Murine Immune Responses to Larval *Dirofilaria Immitis*", pp. 523–528, 1990, *J. Parasitol.*, vol. 76(4).

Abraham, et al., "*Dirofilaria Immitis:* Molting Process of Third–Stage Larvae", pp. 314–322, 1990, *Exp. Parasitol.*, vol. 70.

Abraham, et al., "Active and Passive Immunization of Mice Against Larval *Dirofilaria Immitis*", pp. 275–282, 1988, *J. Parasitol.*, vol. 74(2).

Amiri, et al., "The *Schistosomatium Douthitti* Cerarial Elastase is Biochemically and Structurally Distinct from that of *Schistosoma Mansoni*," pp. 113–120, 1988, *Mol. Biochem. Parasitol.*, vol. 28.

Awobuluyi, et al., "Immunureactivity of Cloned *Dirofilaria Immitis* Proteins in Dogs Following Vaccination with Irradiated Infective Larvae," p. 139, 1989, 38th Annual Meeting, *Am. J. Trop. Med. Hyg.*, Abstract #150, Dec.

Bianco, et al., "Developmentally Regulated Expression and Secretion of a Polymorphic Antigen by Onchocerca Infective–Stage Larvae", pp. 203–212, 1990, *Mol. Biochem. Parasitol.*, vol. 39.

Blair, et al., "Immunization of Dogs Against *Dirofilaria Immitis* by Means of Chemically Abbreviated Infections", 1982, *Fifth International Congress of Parasitol.*, Toronto, Canada, Aug.

Boyer, et al., "Differential Antigen Content and Isotype Recognition of *O. Volvulvus* Antigens from Nodules Removed from Guatemalan Children", p. 169, 1990, 39th Annual Meeting, *Am. J. Trop. Med. Hyg.*, Abstract #221, Nov.

Chomczynski, et al., "Single–Step Method of RNA Isolation by Acid Guanidinium Thiocyanate–Phenol–Chloroform Extraction", pp. 156–159, 1987, *Anal. Biochem.*, vol. 162.

Coleman, et al., "Use of Implantable Intraperitoneal Diffusion Chambers to Study Bordetella Pertussis Pathogenesis: Growth and Toxin Production in Vivo", pp. 33–39, 1986, *J. Infect. Dis.*, vol. 154(1), Jul.

Culpepper, et al., "Molecular Characterization of a *Dirofilaria Immitis* cDNA Encoding a Highly Immunoreactive Antigen", pp. 51–62, 1992, *Mol. Biochem. Parasitol.*, vol. 54.

Dalton, et al., "Thiol Proteases Released in Vitro by *Fasciola Hepatica*", pp. 161–166, 1989, *Mol. Biochem. Parasitol.*, vol. 35.

Davis, et al., "Purification and Biochemical and Immunologic Characterization of a 25KD Glycoprotein from the Surface of *Dirofilaria Immitis* Fourth Stage Larvae", p. 256, 1988, 37th Annual Meeting, *Am. Soc. Trop. Med. Hyg.*, Abstract #404.

Delves, et al., "Neurosecretory–Like Material in 3rd– and 4th–Stage *Dirofilaria Immitis* Larvae (Nematoda: Filarioidea)", pp. 99–104, 1989, *J. Parasitol.*, vol. 99.

Denham, "Vacination Against Filarial Worms Using Radiation–Attenuated Vaccines", pp. 105–111, 1980, *Inter. J. Nucl. Med. Biol.*, vol. 7.

(List continued on next page.)

*Primary Examiner*—Anthony C. Caputa
*Assistant Examiner*—Khalid Masood
*Attorney, Agent, or Firm*—Sheridan Ross P.C.

[57] ABSTRACT

The present invention relates to parasitic helminth proteins of about 39 kD (i.e., P39 proteins); to parasitic helminth P39 nucleic acid molecules, including those that encode such proteins; and to antibodies raised against such proteins. The present invention also includes methods to obtain such proteins, nucleic acid molecules, and antibodies. Also included in the present invention are therapeutic compositions comprising such proteins, nucleic acid molecules, and/or antibodies as well as the use of such therapeutic compositions to protect animals from diseases caused by parasitic helminths.

10 Claims, 9 Drawing Sheets

OTHER PUBLICATIONS

Frank, et al., "Metabolic Labeling of *Dirofilaria Immitis* Third– and Fourth–Stage Larvae and Their Excretory–Secretory Products", pp. 950–956, 1991, *J. Parasitol.*, vol. 77(6).

Gamble, et al., "Purification of a 44 Kilodalton Protease which Mediates the Ecdysis of Infective *Haemonchus Contortus* Larvae", pp. 49–58 (1989), *Mol. Biochem. Parasitol.*, vol. 33.

Grieve, et al., "Identification of *Dirofilaria Immitis* Larval Anitgens with Immunoprophylactic Potential Using Sera from Immune Dogs", pp. 2511–2515, 1992, *J. Immunol.*, vol. 148(8), Apr.

Grieve, "Potential for Immunoprophylaxis Against Heartworm (*Dirofilaria Immitis*) Infection", pp. 187–190, 1989, *Proc. Heartworm Symp.*

Grieve, et al., "Induction of Protective Immunity in Dogs to Infection with *Dirofilaria Immitis* Using Chemically–Abbreviated Infections", pp. 373–379, 1988, *Am. J. Trop. Med. Hyg.*, vol. 39(4).

Grieve, et al., "Epidemiology of Canine Heartworm Infection", pp. 220–246, 1983, *Epidem. Rev.*, vol. 5.

Hewick, et al., "A Gas–Liquid Solid Phase Peptide and Protein Sequenator", pp. 7990–7997, 1981, *J. Biol. Chem.*, vol. 256(15).

Hotez, et al., "Isolation and Characterization of a Proteolytic Enzyme from the Adult Hookworm *Ancylostoma Caninum*", pp. 7343–7348, 1985, *J. Biol. Chem.*, vol. 260(12).

Ibrahim, et al., "Antigen Shedding from the Surface of the Infective Stage Larvae of *Dirofilaria Immitis*", pp. 89–97, 1989, *J. Parasitol.*, vol. 99.

Jwo, et al., "Fractionated Sera from *Schistosoma Mansoni* Infected Patients Confers Passive Protection in Mice", pp. 553–562, 1989, *Am. J. Trop. Med. Hyg.*, vol. 41(5).

Kassis, et al., "Antibody–Dependent Complement–Mediated Killing of Schistosomula in Intraperitoneal Diffusion Chambers in Mice", pp. 1659–1662, 1979, *J. Immunol.*, vol. 123(4), Oct.

Lackey, et al., "Extracellular Proteases Of Onchocerca", pp. 176–185, 1989, *Exp. Parasitol.*, vol. 68.

Lal, et al, "Characterization of Stage–Specific Antigens of Infective of the Filarial Parasite *Brugia Malayi*", pp. 2032–2038, 1989, *J. Immunol.*, vol. 140.

Maki, et al., "Demonstration of Carboxyl and Thiol Protease Activities in Adult *Schistosoma Mansoni, Dirofilaria Immitis, Angiostrongylus Cantonensis* and *Ascaris Suum*", pp. 31–37, 1986, *J. Helminthol.*, vol. 60.

McKerrow, et al., "Proteinases From Invasive Larvae Of The Trematode Parasite *Schistosoma Mansoni* Degrade Connective–Tissue And Basement–Membrane Macromolecules", pp. 47–51, 1985, *Biochem J.*, vol. 231.

McKerrow, et al., "*Schistosoma Mansoni:* Cercarial Degradation of a Radioactively Labeled Collagen Gel", pp. 249–254, 1982, *Exp. Parasitol.*, vol. 53.

McReynolds, et al., "A Large Cuticular Protein from *D. Immitis* that is Also an Excretory or Secretory Product," pp. 173–174, 1989, 38th Annual Meeting, *Am. J. Trop. Med. Hyg.*, Abstract #233, Dec.

McReynolds, et al., "Cloning of a Highly Repeated Protein Located in the Gut of Filarial Parasites," p. 295, 1989, 38th Annual Meeting, *Am. J. Trop. Med. Hyg.*, Abstract #445, Dec.

Mok, et al., "Solubilization of Epicuticular Antigen from *Dirofilaria Immitis* Third–Stage Larvae", pp. 173–182, 1988, *Mol. Biochem. Parasitol.*, vol. 31.

Noble, et al., "*Phylum Nematoda*", pp. 256–322, 1982 (See p. 256), *Parasitol.: The Biology of Animal Parasites,* Section V.

Parab, et al., "Characterization of a Monoclonal Antibody Against Infective Larvae of *Brugia Malayi*", pp. 169–174, 1988, *J. Immunol.*, vol. 64.

Petralanda, et al., "Studies on a Filarial Antigen With Collagenase Activity", pp. 51–59, 1986, *Mol. Biochem. Parasitol.*, vol. 19.

Phillipp, et al., "Biochemical and Immunologic Characterization of a Major Surface Antigen of *Dirofilaria Immitis* Infective Larvae", pp. 2621–2627, 1986, *J. Immunol.*, vol. 136(7), Apr.

Richer, et al., "*Dirofilaria Immitis:* Proteases Produced By Third– And Fourth–Stage Larvae", pp. 213–222, 1992, *Exp. Parasitol.*, vol. 75.

Robertson, et al., "*Toxocara Canis:* Proteolytic Enzymes Secreted by the Infective Larvae in Vitro", pp. 30–36, 1989, *Exp. Parasitol.*, vol. 69.

Rogers, "Enzymes in the Exsheathing Fluid of Nematodes and Their Biological Significance," pp. 495–502, 1982, *J. Parasitol.*, vol. 12(6).

Scott, et al., "Surface–Associated Antigens of Second, Third and Fourth Stage Larvae of *Dirofilaria Immitis*", pp. 339–353, 1990, *Acta Tropica,* vol. 47.

Sher, et al., "Passive Transfer of Acquired Resistance to *Schistosoma Mansoni* in Laboratory Mice", pp. 347–357, 1975, *J. Parasitol.*, vol. 70.

Sim, et al., "Immune Responses in Human *Brugia Malayi* Infections: Serum Dependent Cell–Mediated Destruction of Infective Larvae in Vitro", pp. 362–370, 1982, *Trans. Roy. Soc. Trop. Med. Hyg.*, vol. 76(3).

Strosberg, et al., "Receptor–Based Assays", pp. 30–36, 1991, *Current Opin. in Biotech.,* vol. 2.

Tamashiro, et al., "Proteolytic Cleavage Of IgG and Other Protein Substrated By *Dirofilaria Immitis* Microfilarial Enzymes", pp. 149–154, 1987, *J. Parasitol.*, vol. 73.

Tanner, et al., "*Dipetalonema Viteae* (Filarioidea): Development of the Infective Larvae in Micropore Chambers Implanted Into Normal, Infected and Immunized Jirds", pp. 173–174, 1981, *Trans. Roy. Soc. Trop. Med. Hyg.,* vol. 75(1).

Wang, et al., "Parenteral Formulations of Proteins and Peptides: Stability and Stabilizers", pp. S3–S26, 1988, *J. Parent. Sci. Tech.*, vol. 42.

Willadsen, et al., "Immunologic Control of a Parasitic Arthropod, Identification of a Protective Antigen from *Boophilus Microplus*", pp. 1346–1351, 1989, *J. Immunol.*, vol. 143, Aug.

Wolff, et al., "Direct Gene Transfer Into Mouse Muscle In Vivo", pp. 1465–1468, 1990, *Science,* vol. 247, Mar.

Wong, et al., "*Dirofilaria Immitis:* Fate and Immunogenicity of Irradiated Infective Stage Larvae in Beagles", pp. 465–474, 1974, *Exp. Parasitol.*, vol. 35.

Young, et al., "Efficient Isolation of Genes by Using Antibody Probes", pp. 1194–1198. 1983, *Proc. Natl. Acad. Sci. USA,* vol. 80, Mar.

Alberts et al. (1983) Mol. Biol. of the Cell., 769–772, Garland Publishing, Inc., New York & London.

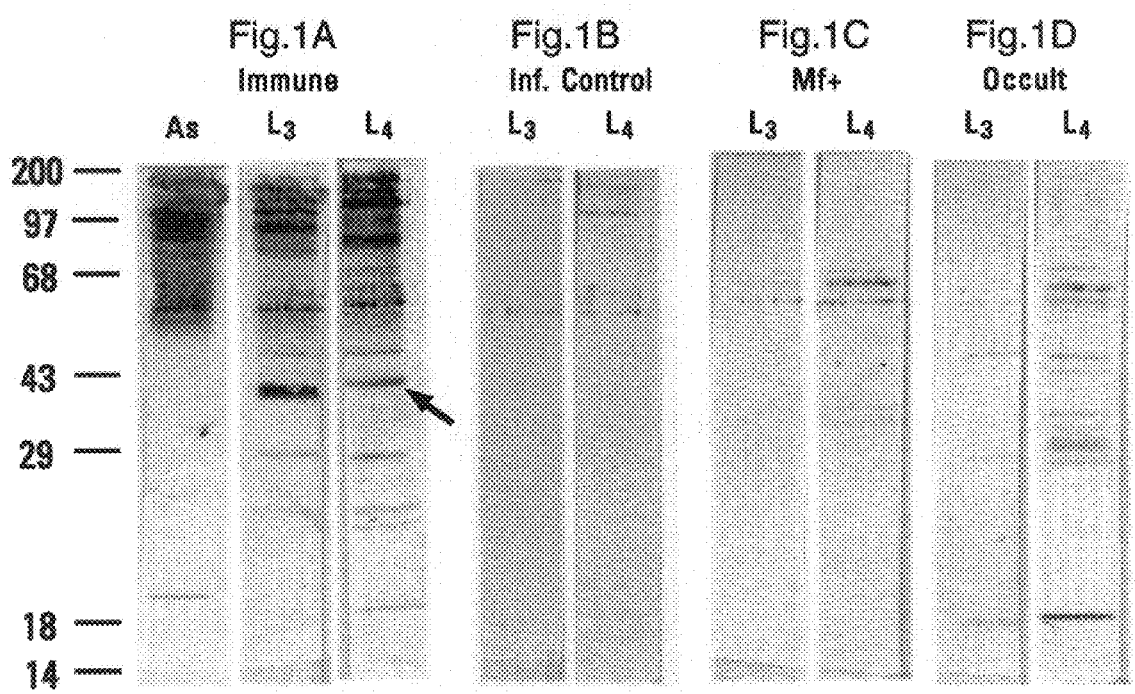

Day 29 PI

Day 142 PI

Day 345 PI

Day 554 PI
Day 22 PC

Day 642 PI
Day 110 PC

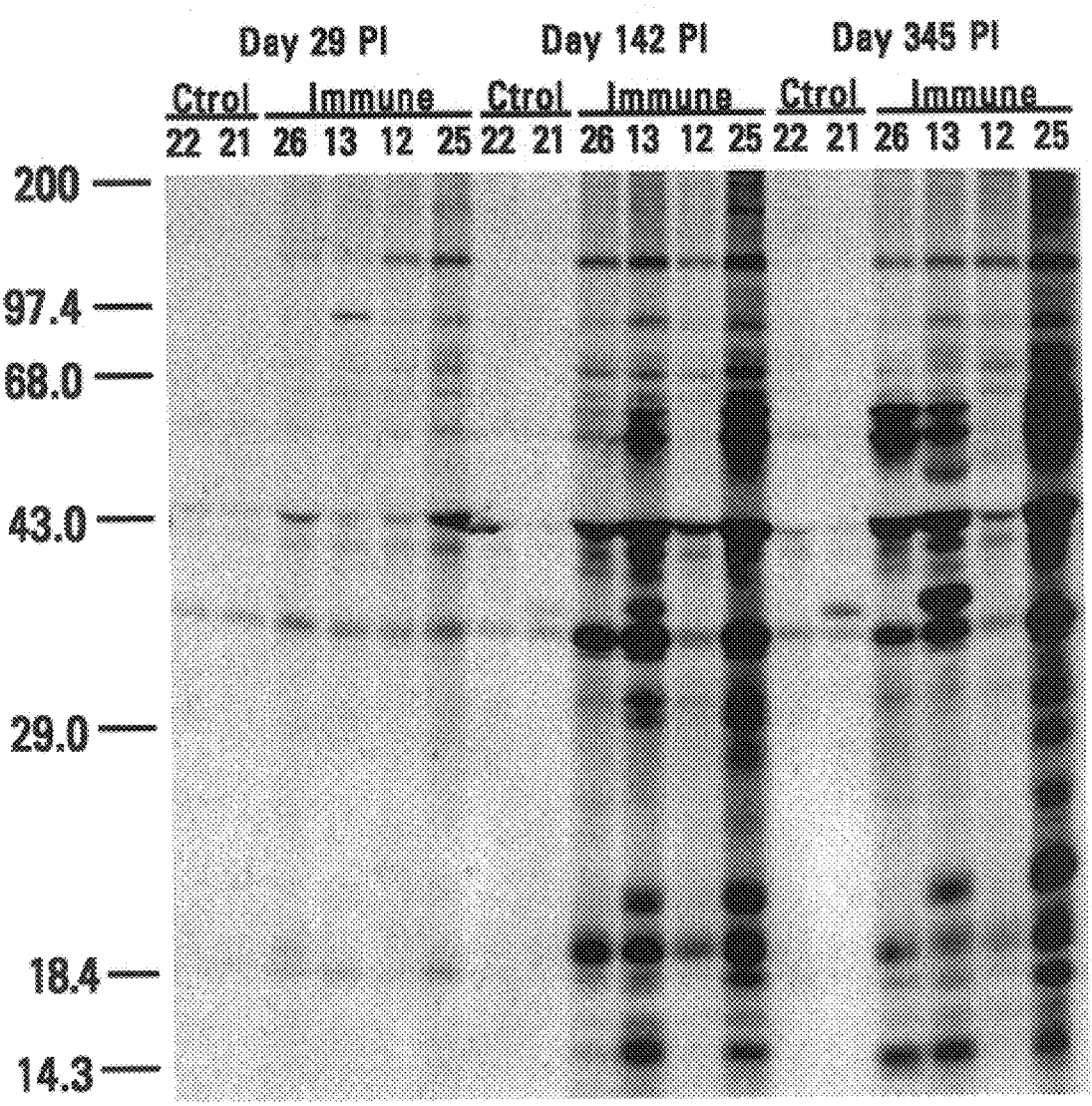

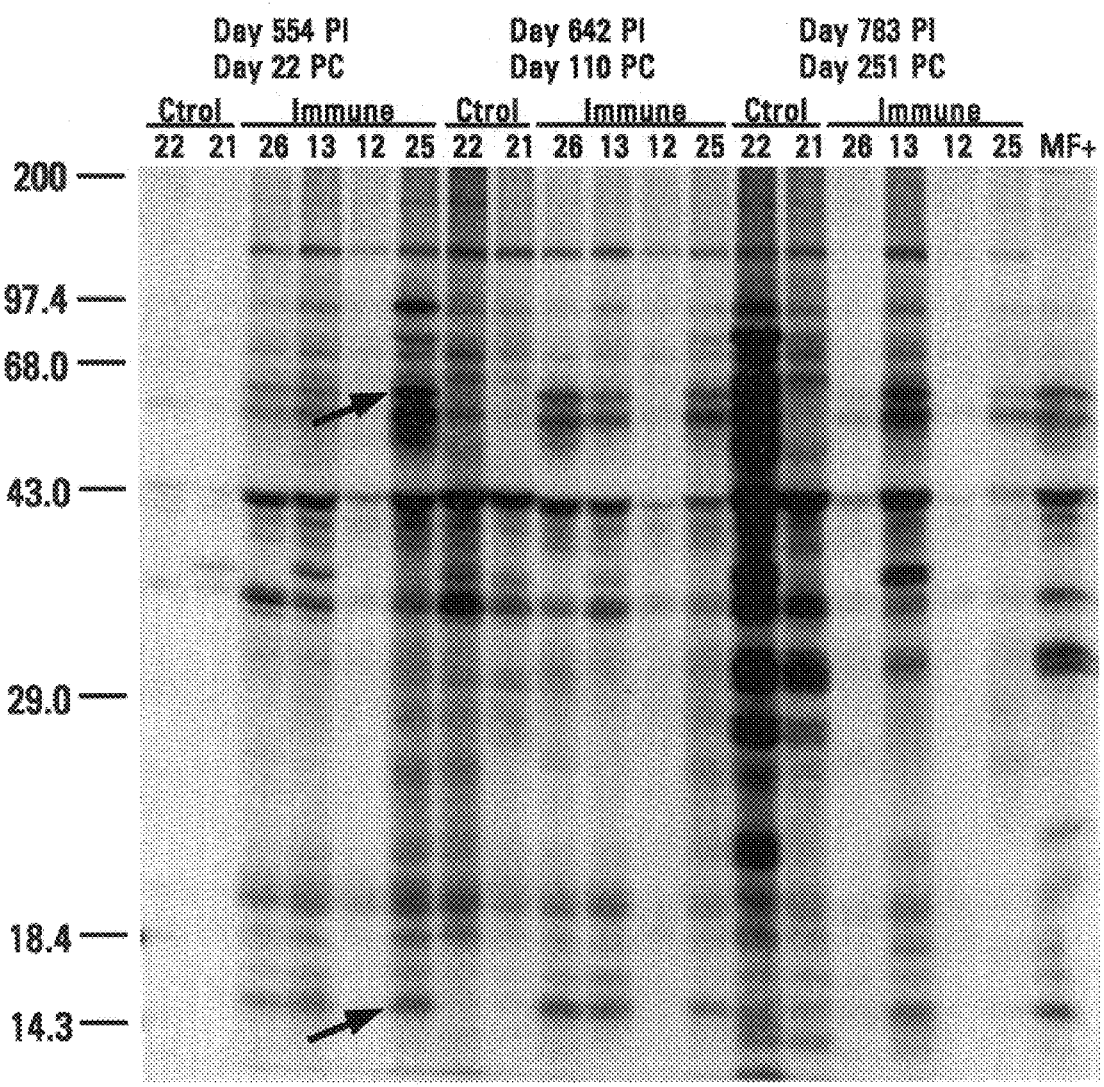

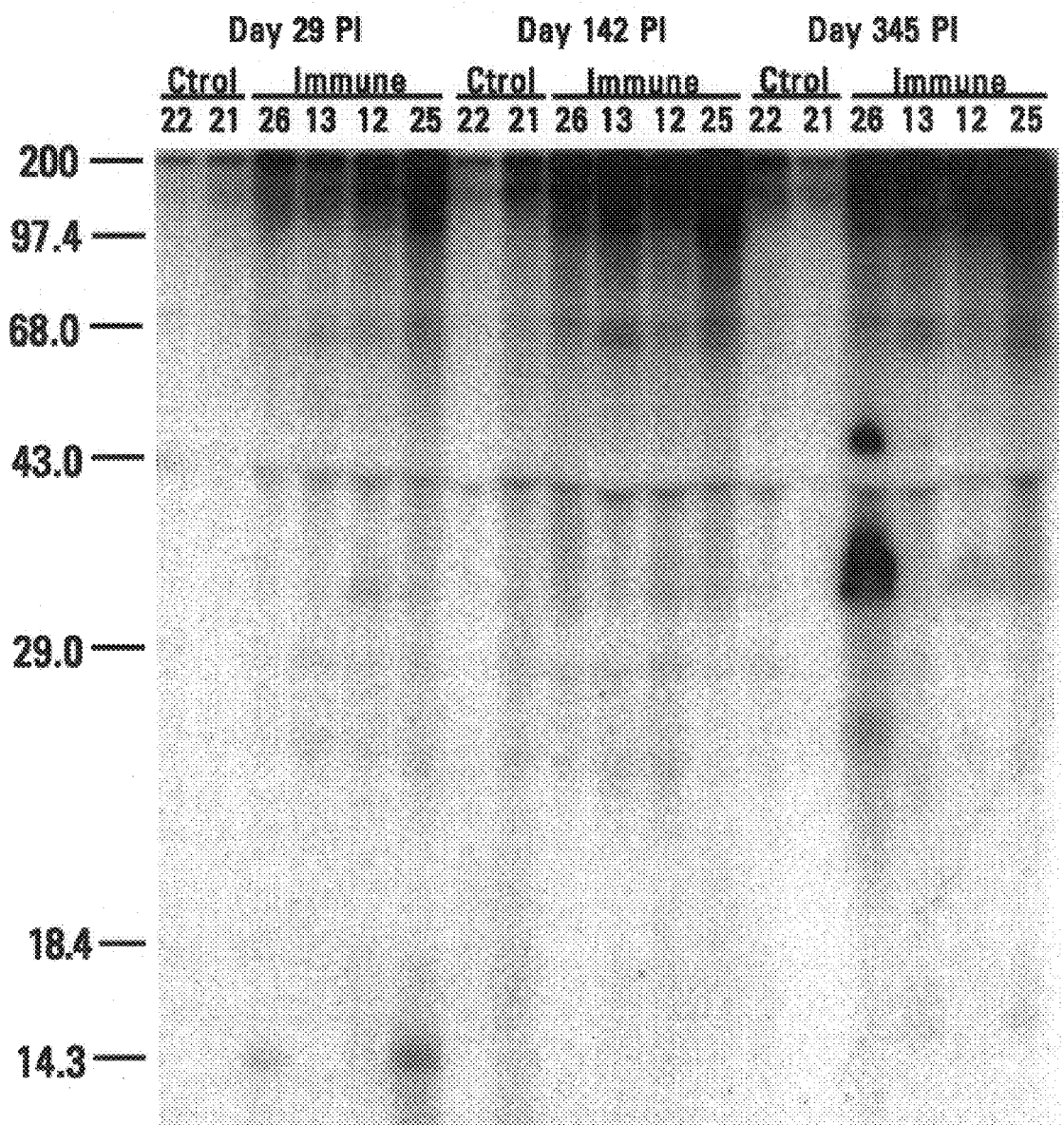

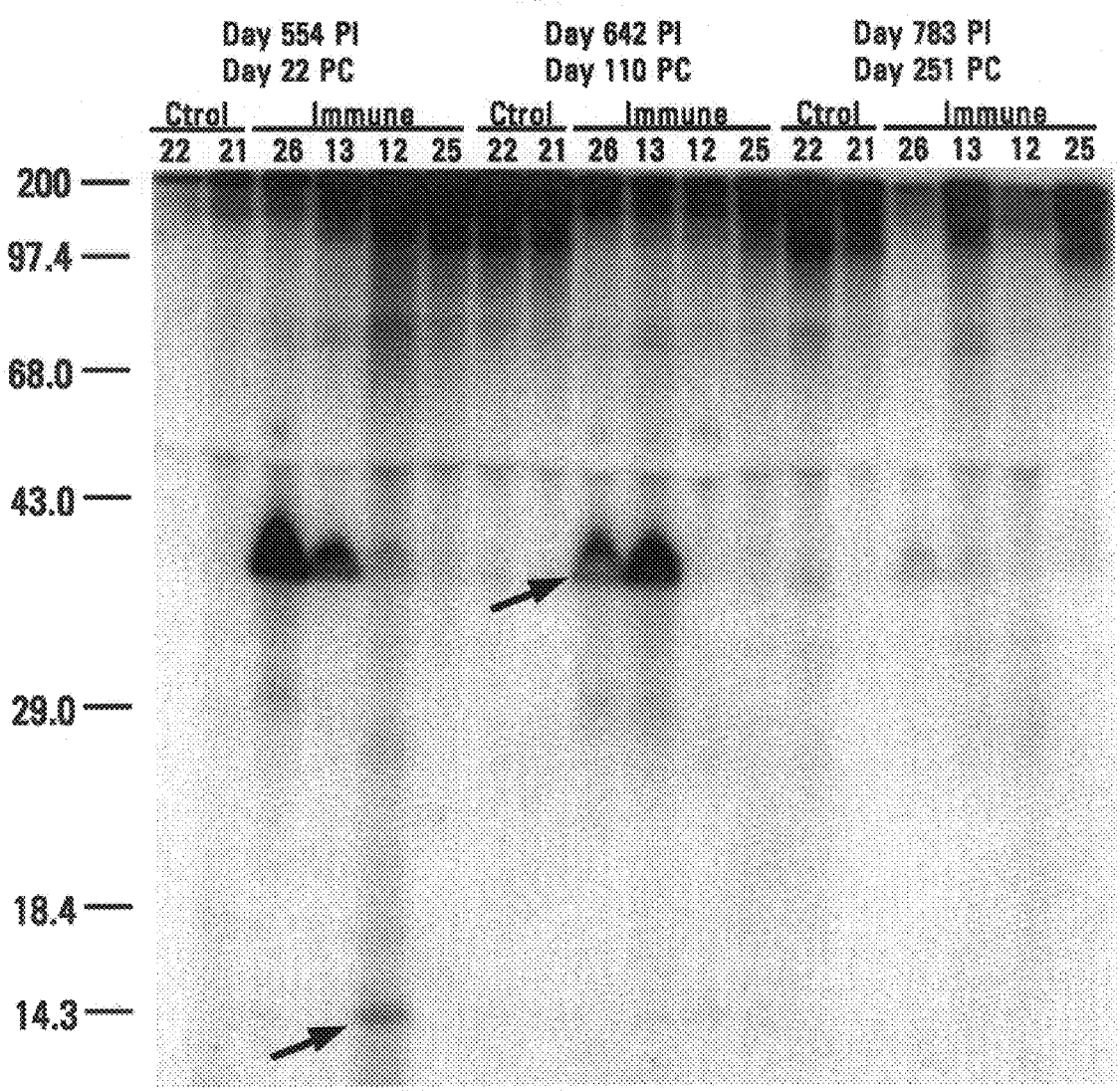

```
                       SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 1185 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 216..1118

(xi) SEQUENCE DESCRIPTION: SEQ ID NO:1:

GTTGTGCTTC TCAACTTTGT CAAATATGCT AATGAGCGAA TACGTCGTGT TGTTTCATCT      60

GAAGTTATTA CTAAAATGAC TGCTGGTATG AACATCCGTC TCAATTGCAC TGACATTCGG    120

CGTAGGTTAA GAGGAATGTT TGTATCGGAA GTACTTACGA ATTGGTTTTC GTTGGGTGAA    180

CTGAAATTTG AATTCCCTGT TGAGCAAATG AGATC ATG ATA GAT TTG AAG AAG       233
                                     Met Ile Asp Leu Lys Lys
                                       1               5

ATT GTG GAT GAT GAA TAT AAC ATT GAT GTG AAG CCT GAT AAA AAT GGC      281
Ile Val Asp Asp Glu Tyr Asn Ile Asp Val Lys Pro Asp Lys Asn Gly
            10                  15                  20

ATT GAA GAG AAG AAA GTG ATA GAA CTG GAA ACG CAG AAT GTG CGG AAT      329
Ile Glu Glu Lys Lys Val Ile Glu Leu Glu Thr Gln Asn Val Arg Asn
        25                  30                  35
```

```
GAT GTA GAT AAA ATT GAT AGC GAT GAT GAT GAC TTC CCT GAA TAT GAA       377
Asp Val Asp Lys Ile Asp Ser Asp Asp Asp Asp Phe Pro Glu Tyr Glu
        40                  45                  50

ATT CCT GCA GGA GAA TTG ATT CTG AAA AAG GAA GAA AAT GAT GAA GAA       425
Ile Pro Ala Gly Glu Leu Ile Leu Lys Lys Glu Glu Asn Asp Glu Glu
55                  60                  65                  70

TAT CGC TGT GTA GAA ATC CCA TAT TAT ATT AGG GAT TGT ATT GAG TTG       473
Tyr Arg Cys Val Glu Ile Pro Tyr Tyr Ile Arg Asp Cys Ile Glu Leu
                75                  80                  85

CTC AAT GAG CAG AAT GAT TGT GCC AAA TTT GAG GCT GCA TTC AAT GCT       521
Leu Asn Glu Gln Asn Asp Cys Ala Lys Phe Glu Ala Ala Phe Asn Ala
        90                  95                  100

CTG AAA CCA ATG ATT AGA CGA CGA GCT GTT GGT TAT GAA CAA TCC GCG       569
Leu Lys Pro Met Ile Arg Arg Arg Ala Val Gly Tyr Glu Gln Ser Ala
                105                 110                 115

GAA GAA CTA CTC TGC CGA CTT ATT GAT CTT AGT GAT CGC TTC AAA ATT       617
Glu Glu Leu Leu Cys Arg Leu Ile Asp Leu Ser Asp Arg Phe Lys Ile
120                 125                 130

GAA CAT TTC CAG GAG AAG CGA CTA CAG CTT ATT GAA TCA TGT CTA GTG       665
Glu His Phe Gln Glu Lys Arg Leu Gln Leu Ile Glu Ser Cys Leu Val
135                 140                 145                 150

ACG AGT CCT TAT CTG GGA AAT GTA GCT ATT GAT GTC ATG TTT TCG AGA       713
Thr Ser Pro Tyr Leu Gly Asn Val Ala Ile Asp Val Met Phe Ser Arg
                155                 160                 165

AAA TGT TCA ATG ATG AAT AGA TAT ATC GTT TTA AAG GCT CTA TCA GAT       761
Lys Cys Ser Met Met Asn Arg Tyr Ile Val Leu Lys Ala Leu Ser Asp
                170                 175                 180

GCG GCG TCA GAA TAT TCA TCT CCA GCC GGA ATT GTC GAA AAT CCA GCC       809
Ala Ala Ser Glu Tyr Ser Ser Pro Ala Gly Ile Val Glu Asn Pro Ala
                185                 190                 195

ATC GAA ATT CCA AAA AAC GGA GGT GAT GTT GAA GGG CAT GTC TCT CTC       857
Ile Glu Ile Pro Lys Asn Gly Gly Asp Val Glu Gly His Val Ser Leu
200                 205                 210

TGC GAT GGC GAT GGA AAA CTG ATC TCC AAG ACA AAA CTT TTC GTG AGA       905
Cys Asp Gly Asp Gly Lys Leu Ile Ser Lys Thr Lys Leu Phe Val Arg
215                 220                 225                 230

GCA CCA ATT ACG ATG TTA AAG GAA AAC AGA TTT ACA CCA ATA GCA AAT       953
Ala Pro Ile Thr Met Leu Lys Glu Asn Arg Phe Thr Pro Ile Ala Asn
                235                 240                 245

TCC TTC TTC TAT CCC TTG ACT GCA ATC GAT CAG CAT CGT GAA CAT CTT      1001
Ser Phe Phe Tyr Pro Leu Thr Ala Ile Asp Gln His Arg Glu His Leu
                250                 255                 260

GAT CTC ATT GGG AGA GAT TCG GAA TTA CTG AGT AAG ATT CTT TTC TGT      1049
Asp Leu Ile Gly Arg Asp Ser Glu Leu Leu Ser Lys Ile Leu Phe Cys
                265                 270                 275

ATG GCT CAT TTG ATC AAA TGT TCT GGC ACT TCT CCA TGT ACG CTT AGA      1097
Met Ala His Leu Ile Lys Cys Ser Gly Thr Ser Pro Cys Thr Leu Arg
        280                 285                 290

ATG TGT AGG TAT GTT GAC TGAATGGAAC TGTTGGCTTG TCTTTCAATT             1145
Met Cys Arg Tyr Val Asp
295                 300

TTAGATAATT GTAAAGTTTG CCAAAATAAA ATTTGAGTTA                          1185

(2) INFORMATION FOR SEQ ID NO:2:

(i) SEQUENCE CHARACTERISTICS:
        (A) LENGTH: 300 amino acids
        (B) TYPE: amino acid
        (D) TOPOLOGY: linear (ii) MOLECULE TYPE: protein
```

(xi) SEQUENCE DESCRIPTION: SEQ ID NO:2:

```
Met Ile Asp Leu Lys Lys Ile Val Asp Asp Glu Tyr Asn Ile Asp Val
 1               5                  10                  15

Lys Pro Asp Lys Asn Gly Ile Glu Glu Lys Lys Val Ile Glu Leu Glu
                20                  25                  30

Thr Gln Asn Val Arg Asn Asp Val Asp Lys Ile Asp Ser Asp Asp Asp
            35                  40                  45

Asp Phe Pro Glu Tyr Glu Ile Pro Ala Gly Glu Leu Ile Leu Lys Lys
        50                  55                  60

Glu Glu Asn Asp Glu Glu Tyr Arg Cys Val Glu Ile Pro Tyr Tyr Ile
 65                  70                  75                  80

Arg Asp Cys Ile Glu Leu Leu Asn Glu Gln Asn Asp Cys Ala Lys Phe
                85                  90                  95

Glu Ala Ala Phe Asn Ala Leu Lys Pro Met Ile Arg Arg Arg Ala Val
               100                 105                 110

Gly Tyr Glu Gln Ser Ala Glu Glu Leu Leu Cys Arg Leu Ile Asp Leu
           115                 120                 125

Ser Asp Arg Phe Lys Ile Glu His Phe Gln Glu Lys Arg Leu Gln Leu
       130                 135                 140

Ile Glu Ser Cys Leu Val Thr Ser Pro Tyr Leu Gly Asn Val Ala Ile
145                 150                 155                 160

Asp Val Met Phe Ser Arg Lys Cys Ser Met Met Asn Arg Tyr Ile Val
               165                 170                 175

Leu Lys Ala Leu Ser Asp Ala Ala Ser Glu Tyr Ser Pro Ala Gly
           180                 185                 190

Ile Val Glu Asn Pro Ala Ile Glu Ile Pro Lys Asn Gly Gly Asp Val
           195                 200                 205

Glu Gly His Val Ser Leu Cys Asp Gly Asp Gly Lys Leu Ile Ser Lys
           210                 215                 220

Thr Lys Leu Phe Val Arg Ala Pro Ile Thr Met Leu Lys Glu Asn Arg
225                 230                 235                 240

Phe Thr Pro Ile Ala Asn Ser Phe Phe Tyr Pro Leu Thr Ala Ile Asp
               245                 250                 255

Gln His Arg Glu His Leu Asp Leu Ile Gly Arg Asp Ser Glu Leu Leu
           260                 265                 270

Ser Lys Ile Leu Phe Cys Met Ala His Leu Ile Lys Cys Ser Gly Thr
       275                 280                 285

Ser Pro Cys Thr Leu Arg Met Cys Arg Tyr Val Asp
       290                 295                 300
```

(2) INFORMATION FOR SEQ ID NO:3:

(i) SEQUENCE CHARACTERISTICS:
        (A) LENGTH: 900 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ATGATAGATT TGAAGAAGAT TGTGGATGAT GAATATAACA TTGATGTGAA GCCTGATAAA    60

AATGGCATTG AAGAGAAGAA AGTGATAGAA CTGGAAACGC AGAATGTGCG GAATGATGTA   120

GATAAAATTG ATAGCGATGA TGATGACTTC CCTGAATATG AAATTCCTGC AGGAGAATTG   180
```

-continued

```
ATTCTGAAAA AGGAAGAAAA TGATGAAGAA TATCGCTGTG TAGAAATCCC ATATTATATT      240

AGGGATTGTA TTGAGTTGCT CAATGAGCAG AATGATTGTG CCAAATTTGA GGCTGCATTC      300

AATGCTCTGA AACCAATGAT TAGACGACGA GCTGTTGGTT ATGAACAATC CGCGGAAGAA      360

CTACTCTGCC GACTTATTGA TCTTAGTGAT CGCTTCAAAA TTGAACATTT CCAGGAGAAG      420

CGACTACAGC TTATTGAATC ATGTCTAGTG ACGAGTCCTT ATCTGGGAAA TGTAGCTATT      480

GATGTCATGT TTTCGAGAAA ATGTTCAATG ATGAATAGAT ATATCGTTTT AAAGGCTCTA      540

TCAGATGCGG CGTCAGAATA TTCATCTCCA GCCGGAATTG TCGAAAATCC AGCCATCGAA      600

ATTCCAAAAA ACGGAGGTGA TGTTGAAGGG CATGTCTCTC TCTGCGATGG CGATGGAAAA      660

CTGATCTCCA AGACAAAACT TTTCGTGAGA GCACCAATTA CGATGTTAAA GGAAAACAGA      720

TTTACACCAA TAGCAAATTC CTTCTTCTAT CCCTTGACTG CAATCGATCA GCATCGTGAA      780

CATCTTGATC TCATTGGGAG AGATTCGGAA TTACTGAGTA AGATTCTTTT CTGTATGGCT      840

CATTTGATCA AATGTTCTGG CACTTCTCCA TGTACGCTTA GAATGTGTAG GTATGTTGAC      900
```

(2) INFORMATION FOR SEQ ID NO:4:

(i) SEQUENCE CHARACTERISTICS:
        (A) LENGTH: 912 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..912

(xi) SEQUENCE DESCRIPTION: SEQ ID NO:4:

```
GCA AAT GAG ATC ATG ATA GAT TTG AAG AAG ATT GTG GAT GAT GAA TAT       48
Ala Asn Glu Ile Met Ile Asp Leu Lys Lys Ile Val Asp Asp Glu Tyr
 1               5                  10                  15

AAC ATT GAT GTG AAG CCT GAT AAA AAT GGC ATT GAA GAG AAG AAA GTG       96
Asn Ile Asp Val Lys Pro Asp Lys Asn Gly Ile Glu Glu Lys Lys Val
                20                  25                  30

ATA GAA CTG GAA ACG CAG AAT GTG CGG AAT GAT GTA GAT AAA ATT GAT      144
Ile Glu Leu Glu Thr Gln Asn Val Arg Asn Asp Val Asp Lys Ile Asp
            35                  40                  45

AGC GAT GAT GAT GAC TTC CCT GAA TAT GAA ATT CCT GCA GGA GAA TTG      192
Ser Asp Asp Asp Asp Phe Pro Glu Tyr Glu Ile Pro Ala Gly Glu Leu
 50                  55                  60

ATT CTG AAA AAG GAA GAA AAT GAT GAA GAA TAT CGC TGT GTA GAA ATC      240
Ile Leu Lys Lys Glu Glu Asn Asp Glu Glu Tyr Arg Cys Val Glu Ile
 65                  70                  75                  80

CCA TAT TAT ATT AGG GAT TGT ATT GAG TTG CTC AAT GAG CAG AAT GAT      288
Pro Tyr Tyr Ile Arg Asp Cys Ile Glu Leu Leu Asn Glu Gln Asn Asp
                85                  90                  95

TGT GCC AAA TTT GAG GCT GCA TTC AAT GCT CTG AAA CCA ATG ATT AGA      336
Cys Ala Lys Phe Glu Ala Ala Phe Asn Ala Leu Lys Pro Met Ile Arg
            100                 105                 110

CGA CGA GCT GTT GGT TAT GAA CAA TCC GCG GAA GAA CTA CTC TGC CGA      384
Arg Arg Ala Val Gly Tyr Glu Gln Ser Ala Glu Glu Leu Leu Cys Arg
        115                 120                 125

CTT ATT GAT CTT AGT GAT CGC TTC AAA ATT GAA CAT TTC CAG GAG AAG      432
Leu Ile Asp Leu Ser Asp Arg Phe Lys Ile Glu His Phe Gln Glu Lys
130                 135                 140

CGA CTA CAG CTT ATT GAA TCA TGT CTA GTG ACG AGT CCT TAT CTG GGA      480
Arg Leu Gln Leu Ile Glu Ser Cys Leu Val Thr Ser Pro Tyr Leu Gly
```

-continued

```
                                                                   145                 150                 155                         160
AAT GTA GCT ATT GAT GTC ATG TTT TCG AGA AAA TGT TCA ATG ATG AAT    528
Asn Val Ala Ile Asp Val Met Phe Ser Arg Lys Cys Ser Met Met Asn
            165                 170                 175

AGA TAT ATC GTT TTA AAG GCT CTA TCA GAT GCG GCA TCA GAA TAT TCA    576
Arg Tyr Ile Val Leu Lys Ala Leu Ser Asp Ala Ala Ser Glu Tyr Ser
            180                 185                 190

TCT CCA GCC GGA ATT GTC GAA AAT CCA GCC ATC GAA ATT CCA AAA AAC    624
Ser Pro Ala Gly Ile Val Glu Asn Pro Ala Ile Glu Ile Pro Lys Asn
            195                 200                 205

GGA GGT GAT GTT GAA GGG CAT GTC TCT CTC TGC GAT GGC GAT GGA AAA    672
Gly Gly Asp Val Glu Gly His Val Ser Leu Cys Asp Gly Asp Gly Lys
            210                 215                 220

CTG ATC TCC AAG ACA AAA CTT TTC GTG AGA GCA CCA ATT ACG ATG TTA    720
Leu Ile Ser Lys Thr Lys Leu Phe Val Arg Ala Pro Ile Thr Met Leu
225                 230                 235                 240

AAG GAA AAC AGA TTT ACA CCA ATA GCA AAT TCC TTC TTC TAT CCC TTG    768
Lys Glu Asn Arg Phe Thr Pro Ile Ala Asn Ser Phe Phe Tyr Pro Leu
            245                 250                 255

ACT GCA ATC GAT CAG CAT CGT GAA CAT CTT GAT CTC ATT GGG AGA GAT    816
Thr Ala Ile Asp Gln His Arg Glu His Leu Asp Leu Ile Gly Arg Asp
            260                 265                 270

TCG GAA TTA CTG AGT AAG ATT CTT TTC TGT ATG GCT CAT TTG ATC AAA    864
Ser Glu Leu Leu Ser Lys Ile Leu Phe Cys Met Ala His Leu Ile Lys
            275                 280                 285

TGT TCT GGC ACT TCT CCA TGT ACG CTT AGA ATG TGT AGG TAT GTT GAC    912
Cys Ser Gly Thr Ser Pro Cys Thr Leu Arg Met Cys Arg Tyr Val Asp
            290                 295                 300
```

(2) INFORMATION FOR SEQ ID NO:5:

(i) SEQUENCE CHARACTERISTICS:
        (A) LENGTH: 304 amino acids
        (B) TYPE: amino acid
        (D) TOPOLOGY: linear (ii) MOLECULE TYPE: protein (xi) SEQUENCE DESCRIPTION: SEQ ID NO:5:

```
Ala Asn Glu Ile Met Ile Asp Leu Lys Lys Ile Val Asp Asp Glu Tyr
1               5                   10                  15

Asn Ile Asp Val Lys Pro Asp Lys Asn Gly Ile Glu Glu Lys Lys Val
            20                  25                  30

Ile Glu Leu Glu Thr Gln Asn Val Arg Asn Asp Val Asp Lys Ile Asp
        35                  40                  45

Ser Asp Asp Asp Phe Pro Glu Tyr Glu Ile Pro Ala Gly Glu Leu
    50                  55                  60

Ile Leu Lys Lys Glu Glu Asn Asp Glu Glu Tyr Arg Cys Val Glu Ile
65              70                  75                  80

Pro Tyr Tyr Ile Arg Asp Cys Ile Glu Leu Leu Asn Glu Gln Asn Asp
            85                  90                  95

Cys Ala Lys Phe Glu Ala Ala Phe Asn Ala Leu Lys Pro Met Ile Arg
                100                 105                 110

Arg Arg Ala Val Gly Tyr Glu Gln Ser Ala Glu Glu Leu Leu Cys Arg
            115                 120                 125

Leu Ile Asp Leu Ser Asp Arg Phe Lys Ile Glu His Phe Gln Glu Lys
        130                 135                 140

Arg Leu Gln Leu Ile Glu Ser Cys Leu Val Thr Ser Pro Tyr Leu Gly
145                 150                 155                 160
```

```
Asn Val Ala Ile Asp Val Met Phe Ser Arg Lys Cys Ser Met Met Asn
            165                 170                 175
Arg Tyr Ile Val Leu Lys Ala Leu Ser Asp Ala Ala Ser Glu Tyr Ser
            180                 185                 190
Ser Pro Ala Gly Ile Val Glu Asn Pro Ala Ile Glu Ile Pro Lys Asn
            195                 200                 205
Gly Gly Asp Val Glu Gly His Val Ser Leu Cys Asp Gly Asp Gly Lys
        210                 215                 220
Leu Ile Ser Lys Thr Lys Leu Phe Val Arg Ala Pro Ile Thr Met Leu
225                 230                 235                 240
Lys Glu Asn Arg Phe Thr Pro Ile Ala Asn Ser Phe Phe Tyr Pro Leu
            245                 250                 255
Thr Ala Ile Asp Gln His Arg Glu His Leu Asp Leu Ile Gly Arg Asp
            260                 265                 270
Ser Glu Leu Leu Ser Lys Ile Leu Phe Cys Met Ala His Leu Ile Lys
            275                 280                 285
Cys Ser Gly Thr Ser Pro Cys Thr Leu Arg Met Cys Arg Tyr Val Asp
        290                 295                 300
```

(2) INFORMATION FOR SEQ ID NO:6:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..216

(xi) SEQUENCE DESCRIPTION: SEQ ID NO:6:

```
GTT GTG CTT CTC AAC TTT GTC AAA TAT GCT AAT GAG CGA ATA CGT CGT      48
Val Val Leu Leu Asn Phe Val Lys Tyr Ala Asn Glu Arg Ile Arg Arg
 1               5                  10                  15

GTT GTT TCA TCT GAA GTT ATT ACT AAA ATG ACT GCT GGT ATG AAC ATC      96
Val Val Ser Ser Glu Val Ile Thr Lys Met Thr Ala Gly Met Asn Ile
            20                  25                  30

CGT CTC AAT TGC ACT GAC ATT CGG CGT AGG TTA AGA GGA ATG TTT GTA     144
Arg Leu Asn Cys Thr Asp Ile Arg Arg Arg Leu Arg Gly Met Phe Val
        35                  40                  45

TCG GAA GTA CTT ACG AAT TGG TTT TCG TTG GGT GAA CTG AAA TTT GAA     192
Ser Glu Val Leu Thr Asn Trp Phe Ser Leu Gly Glu Leu Lys Phe Glu
    50                  55                  60

TTC CCT GTT GAG CAA ATG AGA TCA                                     216
Phe Pro Val Glu Gln Met Arg Ser
65                  70
```

(2) INFORMATION FOR SEQ ID NO:7:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:7:

```
Val Val Leu Leu Asn Phe Val Lys Tyr Ala Asn Glu Arg Ile Arg Arg
 1               5                  10                  15
```

```
Val Val Ser Ser Glu Val Ile Thr Lys Met Thr Ala Gly Met Asn Ile
             20                  25                  30

Arg Leu Asn Cys Thr Asp Ile Arg Arg Arg Leu Arg Gly Met Phe Val
             35                  40                  45

Ser Glu Val Leu Thr Asn Trp Phe Ser Leu Gly Glu Leu Lys Phe Glu
             50                  55                  60

Phe Pro Val Glu Gln Met Arg Ser
 65                  70
```

(2) INFORMATION FOR SEQ ID NO:8:

(i) SEQUENCE CHARACTERISTICS:
        (A) LENGTH: 1061 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GTTAAGAGGA ATGTTTGTAT CGGAAGTACT TACGAATTGG TTTTCGTTGG GTGAACTGAA      60
ATTTGAATTC CCTGTTGAAG CAAATGAGAT CATGATAGAT TTGAAGAAGA TTGTGGATGA     120
TGAATATAAC ATTGATGTGA AGCCTGATAA AAATGGCATT GAAGAGAAGA AAGTGATAGA     180
ACTGGAAACG CAGAATGTGC GGAATGATGT AGATAAAATT GATAGCGATG ATGATGACTT     240
CCCTGAATAT GAAATTCCTG CAGGAGAATT GATTCTGAAA AAGGAAGAAA ATGATGAAGA     300
ATATCGCTGT GTAGAAATCC CATATTATAT TAGGGATTGT ATTGAGTTGC TCAATGAGCA     360
GAATGATTGT GCCAAATTTG AGGCTGCATT CAATGCTCTG AAACCAATGA TTAGACGACG     420
AGCTGTTGGT TATGAACAAT CCGCGGAAGA ACTACTCTGC CGACTTATTG ATCTTAGTGA     480
TCGCTTCAAA ATTGAACATT TCCAGGAGAA GCGACTACAG CTTATTGAAT CATGTCTAGT     540
GACGAGTCCT TATCTGGGAA ATGTAGCTAT TGATGTCATG TTTTCGAGAA ATGTTCAAT     600
GATGAATAGA TATATCGTTT TAAAGGCTCT ATCAGATGCG GCGTCAGAAT ATTCATCTCC     660
AGCCGGAATT GTCGAAAATC CAGCCATCGA AATTCCAAAA AACGGAGGTG ATGTTGAAGG     720
GCATGTCTCT CTCTGCGATG GCGATGGAAA ACTGATCTCC AAGACAAAAC TTTTCGTGAG     780
AGCACCAATT ACGATGTTAA AGGAAAACAG ATTTACACCA ATAGCAAATT CCTTCTTCTA     840
TCCCTTGACT GCAATCGATC AGCATCGTGA ACATCTTGAT CTCATTGGGA GAGATTCGGA     900
ATTACTGAGT AAGATTCTTT TCTGTATGGC TCATTTGATC AAATGTTCTG GCACTTCTCC     960
ATGTACGCTT AGAATGTGTA GGTATGTTGA CTGAATGGAA CTGTTGGCTT GTCTTTCAAT    1020
TTTAGATAAT TGTAAAGTTT GCCAAAATAA AATTTGAGTT A                        1061
```

(2) INFORMATION FOR SEQ ID NO:9:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..990

(xi) SEQUENCE DESCRIPTION: SEQ ID NO:9:

```
TTA AGA GGA ATG TTT GTA TCG GAA GTA CTT ACG AAT TGG TTT TCG TTG        48
Leu Arg Gly Met Phe Val Ser Glu Val Leu Thr Asn Trp Phe Ser Leu
 1               5                  10                  15

GGT GAA CTG AAA TTT GAA TTC CCT GTT GAA GCA AAT GAG ATC ATG ATA        96
Gly Glu Leu Lys Phe Glu Phe Pro Val Glu Ala Asn Glu Ile Met Ile
             20                  25                  30

GAT TTG AAG AAG ATT GTG GAT GAT GAA TAT AAC ATT GAT GTG AAG CCT       144
Asp Leu Lys Lys Ile Val Asp Asp Glu Tyr Asn Ile Asp Val Lys Pro
         35                  40                  45

GAT AAA AAT GGC ATT GAA GAG AAG AAA GTG ATA GAA CTG GAA ACG CAG       192
Asp Lys Asn Gly Ile Glu Glu Lys Lys Val Ile Glu Leu Glu Thr Gln
     50                  55                  60

AAT GTG CGG AAT GAT GTA GAT AAA ATT GAT AGC GAT GAT GAT GAC TTC       240
Asn Val Arg Asn Asp Val Asp Lys Ile Asp Ser Asp Asp Asp Asp Phe
 65                  70                  75                  80

CCT GAA TAT GAA ATT CCT GCA GGA GAA TTG ATT CTG AAA AAG GAA GAA       288
Pro Glu Tyr Glu Ile Pro Ala Gly Glu Leu Ile Leu Lys Lys Glu Glu
                 85                  90                  95

AAT GAT GAA GAA TAT CGC TGT GTA GAA ATC CCA TAT TAT ATT AGG GAT       336
Asn Asp Glu Glu Tyr Arg Cys Val Glu Ile Pro Tyr Tyr Ile Arg Asp
            100                 105                 110

TGT ATT GAG TTG CTC AAT GAG CAG AAT GAT TGT GCC AAA TTT GAG GCT       384
Cys Ile Glu Leu Leu Asn Glu Gln Asn Asp Cys Ala Lys Phe Glu Ala
        115                 120                 125

GCA TTC AAT GCT CTG AAA CCA ATG ATT AGA CGA CGA GCT GTT GGT TAT       432
Ala Phe Asn Ala Leu Lys Pro Met Ile Arg Arg Arg Ala Val Gly Tyr
    130                 135                 140

GAA CAA TCC GCG GAA GAA CTA CTC TGC CGA CTT ATT GAT CTT AGT GAT       480
Glu Gln Ser Ala Glu Glu Leu Leu Cys Arg Leu Ile Asp Leu Ser Asp
145                 150                 155                 160

CGC TTC AAA ATT GAA CAT TTC CAG GAG AAG CGA CTA CAG CTT ATT GAA       528
Arg Phe Lys Ile Glu His Phe Gln Glu Lys Arg Leu Gln Leu Ile Glu
                165                 170                 175

TCA TGT CTA GTG ACG AGT CCT TAT CTG GGA AAT GTA GCT ATT GAT GTC       576
Ser Cys Leu Val Thr Ser Pro Tyr Leu Gly Asn Val Ala Ile Asp Val
            180                 185                 190

ATG TTT TCG AGA AAA TGT TCA ATG ATG AAT AGA TAT ATC GTT TTA AAG       624
Met Phe Ser Arg Lys Cys Ser Met Met Asn Arg Tyr Ile Val Leu Lys
        195                 200                 205

GCT CTA TCA GAT GCG GCG TCA GAA TAT TCA TCT CCA GCC GGA ATT GTC       672
Ala Leu Ser Asp Ala Ala Ser Glu Tyr Ser Ser Pro Ala Gly Ile Val
    210                 215                 220

GAA AAT CCA GCC ATC GAA ATT CCA AAA AAC GGA GGT GAT GTT GAA GGG       720
Glu Asn Pro Ala Ile Glu Ile Pro Lys Asn Gly Gly Asp Val Glu Gly
225                 230                 235                 240

CAT GTC TCT CTC TGC GAT GGC GAT GGA AAA CTG ATC TCC AAG ACA AAA       768
His Val Ser Leu Cys Asp Gly Asp Gly Lys Leu Ile Ser Lys Thr Lys
                245                 250                 255

CTT TTC GTG AGA GCA CCA ATT ACG ATG TTA AAG GAA AAC AGA TTT ACA       816
Leu Phe Val Arg Ala Pro Ile Thr Met Leu Lys Glu Asn Arg Phe Thr
            260                 265                 270

CCA ATA GCA AAT TCC TTC TTC TAT CCC TTG ACT GCA ATC GAT CAG CAT       864
Pro Ile Ala Asn Ser Phe Phe Tyr Pro Leu Thr Ala Ile Asp Gln His
        275                 280                 285

CGT GAA CAT CTT GAT CTC ATT GGG AGA GAT TCG GAA TTA CTG AGT AAG       912
Arg Glu His Leu Asp Leu Ile Gly Arg Asp Ser Glu Leu Leu Ser Lys
    290                 295                 300

ATT CTT TTC TGT ATG GCT CAT TTG ATC AAA TGT TCT GGC ACT TCT CCA       960
Ile Leu Phe Cys Met Ala His Leu Ile Lys Cys Ser Gly Thr Ser Pro
305                 310                 315                 320
```

```
TGT ACG CTT AGA ATG TGT AGG TAT GTT GAC                                              990
Cys Thr Leu Arg Met Cys Arg Tyr Val Asp
                325                 330
```

(2) INFORMATION FOR SEQ ID NO:10:

(i) SEQUENCE CHARACTERISTICS:
        (A) LENGTH: 330 amino acids
        (B) TYPE: amino acid
        (D) TOPOLOGY: linear (ii) MOLECULE TYPE: protein (xi) SEQUENCE DESCRIPTION: SEQ ID NO:10:

```
Leu Arg Gly Met Phe Val Ser Glu Val Leu Thr Asn Trp Phe Ser Leu
 1               5                  10                  15

Gly Glu Leu Lys Phe Glu Phe Pro Val Glu Ala Asn Glu Ile Met Ile
                20                  25                  30

Asp Leu Lys Lys Ile Val Asp Glu Tyr Asn Ile Asp Val Lys Pro
                35                  40                  45

Asp Lys Asn Gly Ile Glu Glu Lys Lys Val Ile Glu Leu Glu Thr Gln
 50                  55                  60

Asn Val Arg Asn Asp Val Asp Lys Ile Asp Ser Asp Asp Asp Asp Phe
 65                  70                  75                  80

Pro Glu Tyr Glu Ile Pro Ala Gly Leu Ile Leu Lys Lys Glu Glu
                85                  90                  95

Asn Asp Glu Glu Tyr Arg Cys Val Glu Ile Pro Tyr Tyr Ile Arg Asp
                100                 105                 110

Cys Ile Glu Leu Leu Asn Glu Gln Asn Asp Cys Ala Lys Phe Glu Ala
                115                 120                 125

Ala Phe Asn Ala Leu Lys Pro Met Ile Arg Arg Ala Val Gly Tyr
                130                 135                 140

Glu Gln Ser Ala Glu Glu Leu Leu Cys Arg Leu Ile Asp Leu Ser Asp
145                 150                 155                 160

Arg Phe Lys Ile Glu His Phe Gln Glu Lys Arg Leu Gln Leu Ile Glu
                165                 170                 175

Ser Cys Leu Val Thr Ser Pro Tyr Leu Gly Asn Val Ala Ile Asp Val
                180                 185                 190

Met Phe Ser Arg Lys Cys Ser Met Met Asn Arg Tyr Ile Val Leu Lys
                195                 200                 205

Ala Leu Ser Asp Ala Ala Ser Glu Tyr Ser Ser Pro Ala Gly Ile Val
                210                 215                 220

Glu Asn Pro Ala Ile Glu Ile Pro Lys Asn Gly Gly Asp Val Glu Gly
225                 230                 235                 240

His Val Ser Leu Cys Asp Gly Asp Gly Lys Leu Ile Ser Lys Thr Lys
                245                 250                 255

Leu Phe Val Arg Ala Pro Ile Thr Met Leu Lys Glu Asn Arg Phe Thr
                260                 265                 270

Pro Ile Ala Asn Ser Phe Phe Tyr Pro Leu Thr Ala Ile Asp Gln His
                275                 280                 285

Arg Glu His Leu Asp Leu Ile Gly Arg Asp Ser Glu Leu Leu Ser Lys
                290                 295                 300

Ile Leu Phe Cys Met Ala His Leu Ile Lys Cys Ser Gly Thr Ser Pro
305                 310                 315                 320

Cys Thr Leu Arg Met Cys Arg Tyr Val Asp
                325                 330
```

(2) INFORMATION FOR SEQ ID NO:11:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 218..531

(xi) SEQUENCE DESCRIPTION: SEQ ID NO:11:

```
GTTGTGCTTC TCAACTTTGT CAAATATGCA AACGAGCAAA TACGTCGTGC TATTTCATCT      60

GACGTTATTA CCAAAATGGC TGCTGGTATG AACATTCGTC TCAAATGCAC AGACATTCGA     120

CGTAGGTTAA GAGGAATGTT TGTATCAGAA GTACTTACGA ACTGGTTTTC GTTGGGTGAA     180

CTAAAATTTG AATTCCCTTC TGCAAGCAGA TGAGGTC ATG GTA GAT TTG AAG AAG      235
                                         Met Val Asp Leu Lys Lys
                                          1               5

ATT GTG ATG GAT GAG TAT AGT GTT GAT GTG AAG GTT GAT AAA AGT GGC      283
Ile Val Met Asp Glu Tyr Ser Val Asp Val Lys Val Asp Lys Ser Gly
         10                  15                  20

ATT GAG GAG AAA AAA GTG ATG CAA CTG GAA ATA CAG GAT GTG CGA AAT      331
Ile Glu Glu Lys Lys Val Met Gln Leu Glu Ile Gln Asp Val Arg Asn
     25                  30                  35

GAT GCA GAC AAA ATT GAT AGC GAT GAT GAT GAC TTC CCT GAG TAT GAA      379
Asp Ala Asp Lys Ile Asp Ser Asp Asp Asp Asp Phe Pro Glu Tyr Glu
 40                  45                  50

ATT CCT TCA GAA GAA TTG ATT CTG GAA AAG GAA GAA AAT GAT GAA GAC      427
Ile Pro Ser Glu Glu Leu Ile Leu Glu Lys Glu Glu Asn Asp Glu Asp
 55                  60                  65                  70

TAT CGC TGT GTA AAA GTC CCT TAT TAC ATT AAG GAT TGT ATT GAG ATG      475
Tyr Arg Cys Val Lys Val Pro Tyr Tyr Ile Lys Asp Cys Ile Glu Met
             75                  80                  85

CTA AAT GAG CAG AAC GAT TGT GCC AAA TTT GAG GCT GCA TTC AAT GCT      523
Leu Asn Glu Gln Asn Asp Cys Ala Lys Phe Glu Ala Ala Phe Asn Ala
         90                  95                 100

CTG AAA CC                                                           531
Leu Lys
```

(2) INFORMATION FOR SEQ ID NO:12:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:12:

```
Met Val Asp Leu Lys Lys Ile Val Met Asp Glu Tyr Ser Val Asp Val
 1               5                  10                  15

Lys Val Asp Lys Ser Gly Ile Glu Glu Lys Lys Val Met Gln Leu Glu
             20                  25                  30

Ile Gln Asp Val Arg Asn Asp Ala Asp Lys Ile Asp Ser Asp Asp Asp
         35                  40                  45

Asp Phe Pro Glu Tyr Glu Ile Pro Ser Glu Glu Leu Ile Leu Glu Lys
     50                  55                  60
```

```
Glu Glu Asn Asp Glu Asp Tyr Arg Cys Val Lys Val Pro Tyr Tyr Ile
 65                  70                  75                  80

Lys Asp Cys Ile Glu Met Leu Asn Glu Gln Asn Asp Cys Ala Lys Phe
                 85                  90                  95

Glu Ala Ala Phe Asn Ala Leu Lys
            100

(2) INFORMATION FOR SEQ ID NO:13:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ATGGTAGATT TGAAGAAGAT TGTGATGGAT GAGTATAGTG TTGATGTGAA GGTTGATAAA      60

AGTGGCATTG AGGAGAAAAA AGTGATGCAA CTGGAAATAC AGGATGTGCG AAATGATGCA     120

GACAAAATTG ATAGCGATGA TGATGACTTC CCTGAGTATG AAATTCCTTC AGAAGAATTG     180

ATTCTGGAAA AGGAAGAAAA TGATGAAGAC TATCGCTGTG TAAAAGTCCC TTATTACATT     240

AAGGATTGTA TTGAGATGCT AAATGAGCAG AACGATTGTG CCAAATTTGA GGCTGCATTC     300

AATGCTCTGA AA                                                        312

(2) INFORMATION FOR SEQ ID NO:14:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..345

(xi) SEQUENCE DESCRIPTION: SEQ ID NO:14:

AAT TTG AAT TCC CTT CTG CAA GCA GAT GAG GTC ATG GTA GAT TTG AAG       48
Asn Leu Asn Ser Leu Leu Gln Ala Asp Glu Val Met Val Asp Leu Lys
 1               5                  10                  15

AAG ATT GTG ATG GAT GAG TAT AGT GTT GAT GTG AAG GTT GAT AAA AGT       96
Lys Ile Val Met Asp Glu Tyr Ser Val Asp Val Lys Val Asp Lys Ser
                 20                  25                  30

GGC ATT GAG GAG AAA AAA GTG ATG CAA CTG GAA ATA CAG GAT GTG CGA      144
Gly Ile Glu Glu Lys Lys Val Met Gln Leu Glu Ile Gln Asp Val Arg
     35                  40                  45

AAT GAT GCA GAC AAA ATT GAT AGC GAT GAT GAT GAC TTC CCT GAG TAT      192
Asn Asp Ala Asp Lys Ile Asp Ser Asp Asp Asp Phe Pro Glu Tyr
 50                  55                  60

GAA ATT CCT TCA GAA GAA TTG ATT CTG GAA AAG GAA GAA AAT GAT GAA      240
Glu Ile Pro Ser Glu Glu Leu Ile Leu Glu Lys Glu Glu Asn Asp Glu
 65                  70                  75                  80

GAC TAT CGC TGT GTA AAA GTC CCT TAT TAC ATT AAG GAT TGT ATT GAG      288
Asp Tyr Arg Cys Val Lys Val Pro Tyr Tyr Ile Lys Asp Cys Ile Glu
                 85                  90                  95

ATG CTA AAT GAG CAG AAC GAT TGT GCC AAA TTT GAG GCT GCA TTC AAT      336
Met Leu Asn Glu Gln Asn Asp Cys Ala Lys Phe Glu Ala Ala Phe Asn
            100                 105                 110
```

```
GCT CTG AAA                                                        345
Ala Leu Lys
        115

(2) INFORMATION FOR SEQ ID NO:15:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:15:

Asn Leu Asn Ser Leu Leu Gln Ala Asp Glu Val Met Val Asp Leu Lys
  1               5                  10                  15

Lys Ile Val Met Asp Glu Tyr Ser Val Asp Val Lys Val Asp Lys Ser
                 20                  25                  30

Gly Ile Glu Glu Lys Lys Val Met Gln Leu Glu Ile Gln Asp Val Arg
             35                  40                  45

Asn Asp Ala Asp Lys Ile Asp Ser Asp Asp Asp Phe Pro Glu Tyr
 50                  55                  60

Glu Ile Pro Ser Glu Glu Leu Ile Leu Glu Lys Glu Asn Asp Glu
 65                  70                  75                  80

Asp Tyr Arg Cys Val Lys Val Pro Tyr Tyr Ile Lys Asp Cys Ile Glu
                 85                  90                  95

Met Leu Asn Glu Gln Asn Asp Cys Ala Lys Phe Glu Ala Ala Phe Asn
                100                 105                 110

Ala Leu Lys
        115

(2) INFORMATION FOR SEQ ID NO:16:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..210

(xi) SEQUENCE DESCRIPTION: SEQ ID NO:16:

GTT GTG CTT CTC AAC TTT GTC AAA TAT GCA AAC GAG CAA ATA CGT CGT    48
Val Val Leu Leu Asn Phe Val Lys Tyr Ala Asn Glu Gln Ile Arg Arg
  1               5                  10                  15

GCT ATT TCA TCT GAC GTT ATT ACC AAA ATG GCT GCT GGT ATG AAC ATT    96
Ala Ile Ser Ser Asp Val Ile Thr Lys Met Ala Ala Gly Met Asn Ile
                 20                  25                  30

CGT CTC AAA TGC ACA GAC ATT CGA CGT AGG TTA AGA GGA ATG TTT GTA   144
Arg Leu Lys Cys Thr Asp Ile Arg Arg Arg Leu Arg Gly Met Phe Val
             35                  40                  45

TCA GAA GTA CTT ACG AAC TGG TTT TCG TTG GGT GAA CTA AAA TTT GAA   192
Ser Glu Val Leu Thr Asn Trp Phe Ser Leu Gly Glu Leu Lys Phe Glu
 50                  55                  60

TTC CCT TCT GCA AGC AGA                                           210
Phe Pro Ser Ala Ser Arg
 65                  70

(2) INFORMATION FOR SEQ ID NO:17:
```

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:17:

Val Val Leu Leu Asn Phe Val Lys Tyr Ala Asn Glu Gln Ile Arg Arg
 1               5                  10                  15

Ala Ile Ser Ser Asp Val Ile Thr Lys Met Ala Ala Gly Met Asn Ile
                20                  25                  30

Arg Leu Lys Cys Thr Asp Ile Arg Arg Arg Leu Arg Gly Met Phe Val
            35                  40                  45

Ser Glu Val Leu Thr Asn Trp Phe Ser Leu Gly Glu Leu Lys Phe Glu
        50                  55                  60

Phe Pro Ser Ala Ser Arg
65                   70

(2) INFORMATION FOR SEQ ID NO:18:

(i) SEQUENCE CHARACTERISTICS:
        (A) LENGTH: 909 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GTTGTGCTTC TCAACTTTGT CAAATATGCA AGTAAGTTT CATTTCGCTC AAGTTTGCGC      60

TGGTCCTTTA AATTCTTAAT ATATTTAACA ATCGTCGGGT CTTAAGTATG ATATCACCAT    120

AAGATTGGAA GGTTTCAGCA AACAAATACG TCGTTCTAAT TCAAATGAAA TTGTTACTAA    180

AATGGCCTTC CTTGGTGTCA ACATCCGTCT TAAATGTTCA GATCCTCGAC GCAGGCTAAG    240

AGGAATGGTT GTAGCAGGTC CATATATTTT TTCATTTTGT TTTACTTATT TTGCATTTCA    300

GGGACATTTA GGTGCTCACA GAAGGAATCC TTTTTTATAG AAATAAGATT TTACAAGTGA    360

AGTTATGGAT TAATGTACAG ATAATATTAT AATTTTAGAA TTGTATATTT TTTTCAAGAA    420

GTGATTACGG ATTGGTTCTC TTTGGGTGAG CTGAAATTTG AATTTCCTCC TGAAGCAGAT    480

GAGATCATGA TAGACTTAAA GAAGATTGTG GATGATGAGT ACGATGCAGA TGTGCAACCT    540

CTTAAAAATG ATAATGAGGA GAAGAAAGTG ATACAACTGG AAATACGGGA TGCAGAGAAT    600

GATGCAGACA AAGTGGATAG TGATGATGAT GATGACTTTC CTGTGTACGA AATCCCCGAA    660

GAGGAATTGA CCTTAAAAAA GGTTTACATA GTTGCTGTAT ATGGCCAGTT ATATTAGGCC    720

GTAAACAATG TACTTTGGTC AGGTTTTTTT TATAGAATGC TTCTTTAGGA TATCTTTATT    780

TCTCCAGGAA GAAAATGATG AAGATTACCG TAATCTAGAG ATGCCATATT ATATTATGGA    840

TTGTATTGAG GGACTGAATG AACAGAATGA TTATGCCAAA TTTGAGGCTG CATTCAATGC    900

TCTGAAACC                                                           909

(2) INFORMATION FOR SEQ ID NO:19:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: DNA (genomic, without introns)

(ix) FEATURE:
            (A) NAME/KEY: CDS
            (B) LOCATION: 220..536

(xi) SEQUENCE DESCRIPTION: SEQ ID NO:19:

```
GTTGTGCTTC TCAACTTTGT CAAATATGCA AACAAACAAA TACGTCGTTC TAATTCAAAT      60

GAAATTGTTA CTAAAATGGC CTTCCTTGGT GTCAACATCC GTCTTAAATG TTCAGATCCT     120

CGACGCAGGC TAAGAGGAAT GGTTGTAGCA GAAGTGATTA CGGATTGGTT CTCTTTGGGT     180

GAGCTGAAAT TTGAATTTCC TCCTGAAGCA GATGAGATC ATG ATA GAC TTA AAG        234
                                           Met Ile Asp Leu Lys
                                            1               5

AAG ATT GTG GAT GAT GAG TAC GAT GCA GAT GTG CAA CCT CTT AAA AAT       282
Lys Ile Val Asp Asp Glu Tyr Asp Ala Asp Val Gln Pro Leu Lys Asn
             10                  15                  20

GAT AAT GAG GAG AAG AAA GTG ATA CAA CTG GAA ATA CGG GAT GCA GAG       330
Asp Asn Glu Glu Lys Lys Val Ile Gln Leu Glu Ile Arg Asp Ala Glu
                 25                  30                  35

AAT GAT GCA GAC AAA GTG GAT AGT GAT GAT GAT GAT GAC TTT CCT GTG       378
Asn Asp Ala Asp Lys Val Asp Ser Asp Asp Asp Asp Asp Phe Pro Val
             40                  45                  50

TAC GAA ATC CCC GAA GAG GAA TTG ACC TTA AAA AAG GAA GAA AAT GAT       426
Tyr Glu Ile Pro Glu Glu Glu Leu Thr Leu Lys Lys Glu Glu Asn Asp
 55                  60                  65

GAA GAT TAC CGT AAT CTA GAG ATG CCA TAT TAT ATT ATG GAT TGT ATT       474
Glu Asp Tyr Arg Asn Leu Glu Met Pro Tyr Tyr Ile Met Asp Cys Ile
 70                  75                  80                  85

GAG GGA CTG AAT GAA CAG AAT GAT TAT GCC AAA TTT GAG GCT GCA TTC       522
Glu Gly Leu Asn Glu Gln Asn Asp Tyr Ala Lys Phe Glu Ala Ala Phe
                 90                  95                 100

AAT GCT CTG AAA CC                                                    536
Asn Ala Leu Lys
        105
```

(2) INFORMATION FOR SEQ ID NO:20:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ile Asp Leu Lys Lys Ile Val Asp Asp Glu Tyr Asp Ala Asp Val
 1               5                  10                  15

Gln Pro Leu Lys Asn Asp Asn Glu Glu Lys Lys Val Ile Gln Leu Glu
                 20                  25                  30

Ile Arg Asp Ala Glu Asn Asp Ala Asp Lys Val Asp Ser Asp Asp Asp
             35                  40                  45

Asp Asp Phe Pro Val Tyr Glu Ile Pro Glu Glu Leu Thr Leu Lys
         50                  55                  60

Lys Glu Glu Asn Asp Glu Asp Tyr Arg Asn Leu Glu Met Pro Tyr Tyr
 65                  70                  75                  80

Ile Met Asp Cys Ile Glu Gly Leu Asn Glu Gln Asn Asp Tyr Ala Lys
                 85                  90                  95

Phe Glu Ala Ala Phe Asn Ala Leu Lys
                100                 105
```

(2) INFORMATION FOR SEQ ID NO:21:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: DNA (genomic, without introns)

(xi) SEQUENCE DESCRIPTION: SEQ ID NO:21:

```
ATGATAGACT TAAAGAAGAT TGTGGATGAT GAGTACGATG CAGATGTGCA ACCTCTTAAA      60

AATGATAATG AGGAGAAGAA AGTGATACAA CTGGAAATAC GGGATGCAGA GAATGATGCA     120

GACAAAGTGG ATAGTGATGA TGATGATGAC TTTCCTGTGT ACGAAATCCC CGAAGAGGAA     180

TTGACCTTAA AAAGGAAGA AAATGATGAA GATTACCGTA ATCTAGAGAT GCCATATTAT     240

ATTATGGATT GTATTGAGGG ACTGAATGAA CAGAATGATT ATGCCAAATT TGAGGCTGCA     300

TTCAATGCTC TGAAA                                                     315
```

(2) INFORMATION FOR SEQ ID NO:22:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: DNA (genomic, without introns)

(ix) FEATURE:
        (A) NAME/KEY: CDS
        (B) LOCATION: 1..534

(xi) SEQUENCE DESCRIPTION: SEQ ID NO:22:

```
GTT GTG CTT CTC AAC TTT GTC AAA TAT GCA AAC AAA CAA ATA CGT CGT       48
Val Val Leu Leu Asn Phe Val Lys Tyr Ala Asn Lys Gln Ile Arg Arg
 1               5                  10                  15

TCT AAT TCA AAT GAA ATT GTT ACT AAA ATG GCC TTC CTT GGT GTC AAC       96
Ser Asn Ser Asn Glu Ile Val Thr Lys Met Ala Phe Leu Gly Val Asn
             20                  25                  30

ATC CGT CTT AAA TGT TCA GAT CCT CGA CGC AGG CTA AGA GGA ATG GTT      144
Ile Arg Leu Lys Cys Ser Asp Pro Arg Arg Arg Leu Arg Gly Met Val
         35                  40                  45

GTA GCA GAA GTG ATT ACG GAT TGG TTC TCT TTG GGT GAG CTG AAA TTT      192
Val Ala Glu Val Ile Thr Asp Trp Phe Ser Leu Gly Glu Leu Lys Phe
 50                  55                  60

GAA TTT CCT CCT GAA GCA GAT GAG ATC ATG ATA GAC TTA AAG AAG ATT      240
Glu Phe Pro Pro Glu Ala Asp Glu Ile Met Ile Asp Leu Lys Lys Ile
 65                  70                  75                  80

GTG GAT GAT GAG TAC GAT GCA GAT GTG CAA CCT CTT AAA AAT GAT AAT      288
Val Asp Asp Glu Tyr Asp Ala Asp Val Gln Pro Leu Lys Asn Asp Asn
                 85                  90                  95

GAG GAG AAG AAA GTG ATA CAA CTG GAA ATA CGG GAT GCA GAG AAT GAT      336
Glu Glu Lys Lys Val Ile Gln Leu Glu Ile Arg Asp Ala Glu Asn Asp
            100                 105                 110

GCA GAC AAA GTG GAT AGT GAT GAT GAT GAT GAC TTT CCT GTG TAC GAA      384
Ala Asp Lys Val Asp Ser Asp Asp Asp Asp Asp Phe Pro Val Tyr Glu
        115                 120                 125

ATC CCC GAA GAG GAA TTG ACC TTA AAA AAG GAA GAA AAT GAT GAA GAT      432
Ile Pro Glu Glu Glu Leu Thr Leu Lys Lys Glu Glu Asn Asp Glu Asp
    130                 135                 140

TAC CGT AAT CTA GAG ATG CCA TAT TAT ATT ATG GAT TGT ATT GAG GGA      480
Tyr Arg Asn Leu Glu Met Pro Tyr Tyr Ile Met Asp Cys Ile Glu Gly
```

-continued

```
Tyr Arg Asn Leu Glu Met Pro Tyr Tyr Ile Met Asp Cys Ile Glu Gly
145                 150                 155                 160

CTG AAT GAA CAG AAT GAT TAT GCC AAA TTT GAG GCT GCA TTC AAT GCT      528
Leu Asn Glu Gln Asn Asp Tyr Ala Lys Phe Glu Ala Ala Phe Asn Ala
                165                 170                 175

CTG AAA                                                              534
Leu Lys
```

(2) INFORMATION FOR SEQ ID NO:23:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO:23:

```
Val Val Leu Leu Asn Phe Val Lys Tyr Ala Asn Lys Gln Ile Arg Arg
1               5                   10                  15

Ser Asn Ser Asn Glu Ile Val Thr Lys Met Ala Phe Leu Gly Val Asn
                20                  25                  30

Ile Arg Leu Lys Cys Ser Asp Pro Arg Arg Leu Arg Gly Met Val
            35                  40                  45

Val Ala Glu Val Ile Thr Asp Trp Phe Ser Leu Gly Glu Leu Lys Phe
    50                  55                  60

Glu Phe Pro Pro Glu Ala Asp Glu Ile Met Ile Asp Leu Lys Lys Ile
65                  70                  75                  80

Val Asp Asp Glu Tyr Asp Ala Asp Val Gln Pro Leu Lys Asn Asp Asn
                85                  90                  95

Glu Glu Lys Lys Val Ile Gln Leu Glu Ile Arg Asp Ala Glu Asn Asp
                100                 105                 110

Ala Asp Lys Val Asp Ser Asp Asp Asp Phe Pro Val Tyr Glu
            115                 120                 125

Ile Pro Glu Glu Glu Leu Thr Leu Lys Lys Glu Glu Asn Asp Glu Asp
130                 135                 140

Tyr Arg Asn Leu Glu Met Pro Tyr Tyr Ile Met Asp Cys Ile Glu Gly
145                 150                 155                 160

Leu Asn Glu Gln Asn Asp Tyr Ala Lys Phe Glu Ala Ala Phe Asn Ala
                165                 170                 175

Leu Lys
```

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:24:

```
CGCGGATCCC GCAAATGAGA TCATG                                          25
```

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (primer)

(xi) SEQUENCE DESCRIPTION: SEQ ID NO:25:

GCCAACGGAT CCATTCAGTC AACATACC                                              28

(2) INFORMATION FOR SEQ ID NO:26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:26:

GTGGAATTGT GAGCGG                                                           16

(2) INFORMATION FOR SEQ ID NO:27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:27:

GCGGGATCCT ATAAATATGA TAGATTTGAA GAAG                                       34

(2) INFORMATION FOR SEQ ID NO:28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:28:

GCTCTAGACC ATGATAGATT TGAAGAAG                                              28

(2) INFORMATION FOR SEQ ID NO:29:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:29:

CGCGGATCCG GTTGTGCTTC TCAACTTTGT C                                          31

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

-continued (xi) SEQUENCE DESCRIPTION: SEQ ID NO:30:

GGTTTCAGAG CATTGAATGC           20

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:31:

CATTTTTATC AGGCTTCAC           19

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:32:

GATAGCGATG ATGATGAC           18

(2) INFORMATION FOR SEQ ID NO:33:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:33:

GTTGAGGATC CGCCACCATG ATAGATTTGA AGAAG           35

PARASITIC HELMINTH NUCLEIC ACID MOLECULES/AND USES THEREOF

CROSS-REFERENCE TO RELATED APPLICATIONS

The present application is a continuation-in-part of U.S. patent application Ser. No. 08/003,389, (ABN) filed Jan. 12, 1993, which is a continuation-in-part of U.S. patent application Ser. No. 07/654,226, (ABN) filed Feb. 12, 1991. The present application is also a continuation-in-part of U.S. patent application Ser. No. 08/101,283, (ABN) filed Aug. 3, 1993, which is a continuation of U.S. patent application Ser. No. 07/654,226, (ABN) filed Feb. 12, 1991. The present application is also a continuation-in-part of PCT/US94/00679, the international filing date of which is Jan. 12, 1994. PCT/US94/00679 claims priority to U.S. patent application Ser. No. 08/003,389, (ABN) ibid., to U.S. patent application Ser. No. 08/003,257, (ABN) filed Jan. 12, 1993, and to U.S. patent application Ser. No. 08/109,391, U.S. Pat. No. 5,639,876) filed Aug. 19, 1993. Each of the patent applications referred to in this section is incorporated by reference herein in its entirety.

FIELD OF THE INVENTION

The present invention relates to novel parasitic helminth P39 proteins, nucleic acid molecules encoding such proteins and antibodies raised against such proteins. The present invention also includes a method to obtain such nucleic acid molecules, proteins and antibodies as well as use of such compounds to protect animals from infections caused by parasitic helminths. The present invention particularly relates to certain *Dirofilaria immitis, Onchocerca volvulus,* and *Brugia malayi* P39 nucleic acid molecules, proteins and antibodies as well as their use to protect animals from parasitic helminth infection.

BACKGROUND OF THE INVENTION

Parasitic helminth infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasitic helminth infections, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

It is particularly difficult to develop vaccines against parasitic helminth infections both because of the complexity of the parasite's life cycle and because, while administration of parasites or parasite antigens can lead to the production of a significant antibody response, the immune response is typically not sufficient to protect the animal against infection.

As an example of the complexity of parasitic helminths, the life cycle of *D. immitis,* the helminth that causes heartworm, includes a variety of life forms, each of which presents different targets, and challenges, for immunization. Adult forms of the parasite are quite large and preferentially inhabit the heart and pulmonary arteries of an animal. Sexually mature adults, after mating, produce microfilariae which traverse capillary beds and circulate in the vascular system of the dog. One method of demonstrating infection in the dog is to detect the circulating microfilariae.

If the dog is maintained in an insect-free environment, the life cycle of the parasite cannot progress. However, when microfilariae are ingested by the female mosquito during blood feeding on an infected dog, subsequent development of the microfilariae into larvae occurs in the mosquito. The microfilariae go through two larval stages (L1 and L2) and finally become mature third stage larvae (L3) which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilariae can be detected, but the existence of the adult heartworms can be determined through thoracic examination.

Heartworm not only is a major problem in dogs, which typically cannot even develop immunity upon infection (i.e., dogs can become reinfected even after being cured by chemotherapy), but is also becoming increasingly widespread in other companion animals, such as cats and ferrets. Heartworm infections have also been reported in humans. Other parasitic helminthic infections are also widespread, and all require better treatment, including a preventative vaccine program. *O. volvulus,* for example, causes onchocerciasis (also known as river blindness) in humans. Up to 50 million people throughout the world are reported to be infected with *O. volvulus,* with over a million being blinded due to infection. *Brugia filariids* can infect humans and other animals, causing diseases including filariasis (including lymphatic filariasis), elephantiasis and tropical eosinophilia.

Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. A large number of materials are immunogenic and produce sera which test positive in immunoassays for ability to react with the immunizing antigen, but which fail to protect the hosts against infection. Accordingly, the use of serum simply resulting from immunization or from infection by a parasitic helminth to screen for candidate vaccines does not provide sufficient specificity to identify protective immunogens. On the other hand, serum or other components of blood from immunized animals which is demonstrably protective against infection would contain antibodies, cells, or other factors that could selectively bind to potential antigens that, if used as therapeutic compositions, would elicit immune responses that protect against challenge. A method to use serum from immune animals to identify candidate parasitic helminth vaccines is disclosed in U.S. patent application Ser. No. 08/101,283, ibid., also published as PCT International Publication No. WO 92/13560, by Grieve et al., on Aug. 20, 1992.

An alternative approach to finding a suitable parasitic helminth vaccine has been to attempt to identify prominent antigens in the infective stage of the helminth. Researchers have identified several proteins in the infective stage of *D. immitis,* including, for example, a 35-kilodalton (kD) major surface antigen of *D. immitis* third stage larvae (Philipp, et al., 1986, *J. Immunol.* 136, 2621–2627; Ibrahim, et al., 1989, *Parasitol.* 99, 89–97; Scott, et al, 1990, *Acta Tropica* 47, 339–353) as well as three major surface proteins of the L4 having molecular weights of 150 kD, 52 kD, and 25 kD (Davis, et al., 1988, Abstract 404, 37th Annual Meeting, *Am. Soc. Trop. Med. Hyg.*). Scott et al., ibid., also identified a number of other proteins on the surface of *D. immitis* having molecular weights ranging from 3 kD to 66 kD. None of these proteins has yet been shown to be an effective vaccine.

Furthermore, although several Onchocerca genes have been isolated, genes encoding antigens targeted specifically to L3 and L4 stage larvae have apparently not been reported. In particular, genes encoding antigens that selectively bind to serum obtained from a host that is immune to Onchocerca infection (e.g., *O. volvulus* infection), apparently have not been isolated, nor apparently have such antigens been characterized.

As such, there remains a need to identify an efficacious composition that protects animals against diseases caused by parasitic helminths and that, preferably, also protects animals from infection by such helminths.

SUMMARY OF THE INVENTION

The present invention relates to parasitic helminth P39 proteins; to parasitic helminth P39 nucleic acid molecules, including those that encode such proteins; and to antibodies raised against such proteins (anti-parasitic helminth P39 antibodies). The present invention also includes methods to obtain such proteins, nucleic acid molecules and antibodies. Also included in the present invention are therapeutic compositions comprising such proteins, nucleic acid molecules and/or antibodies, as well as use of such therapeutic compositions to protect animals from diseases caused by parasitic helminths.

One embodiment of the present invention is an isolated parasitic helminth nucleic acid molecule that hybridizes under stringent hybridization conditions with a *Dirofilaria immitis* P39 gene, an *Onchocerca volvulus* P39 gene, and/or a *Brugia malayi* P39 gene. A *D. immitis* P39 gene preferably includes nucleic acid SEQ ID NO:1 and/or SEQ ID NO:8; an *O. volvulus* P39 gene preferably includes nucleic acid sequence SEQ ID NO:11; and a *B. malayi* P39 gene preferably includes nucleic acid sequence SEQ ID NO:18. A P39 nucleic acid molecule of the present invention can include a regulatory region of a parasitic helminth P39 gene and/or can encode a parasitic helminth P39 protein. Particularly preferred P39 nucleic acid molecules include nucleic acid sequence SEQ ID NO:1, nucleic acid sequence SEQ ID NO:3, nucleic acid sequence SEQ ID NO:4, nucleic acid sequence SEQ ID NO:6, nucleic acid sequence SEQ ID NO:8, nucleic acid sequence SEQ ID NO:9, nucleic acid sequence SEQ ID NO:11, nucleic acid sequence SEQ ID NO:13, nucleic acid sequence SEQ ID NO:14, nucleic acid sequence SEQ ID NO:16, nucleic acid sequence SEQ ID NO:18, nucleic acid sequence SEQ ID NO:19, nucleic acid sequence SEQ ID NO:21 and/or nucleic acid sequence SEQ ID NO:22, as well as allelic variants of one or more of those nucleic acid molecules.

The present invention also relates to recombinant molecules, recombinant viruses and recombinant cells that include parasitic helminth P39 nucleic acid molecules of the present invention. Also included are methods to produce such nucleic acid molecules, recombinant molecules, recombinant viruses and recombinant cells.

Another embodiment of the present invention includes an isolated parasitic helminth P39 protein, including a protein that includes a parasitic helminth P39 protein. A preferred parasitic helminth P39 protein, when administered to an animal, is capable of eliciting an immune response against a natural parasitic helminth P39 protein and/or of selectively binding to immune serum derived from an animal that is immune to infection by the parasitic helminth. A preferred parasitic helminth P39 protein is a third stage or fourth stage larval protein. In one embodiment, a preferred P39 protein has a molecular weight of about 39 kD as determined by Tris-glycine SDS PAGE. Particularly preferred P39 proteins are proteins that include amino acid sequence SEQ ID NO:2, amino acid sequence SEQ ID NO:5, amino acid sequence SEQ ID NO:7, amino acid sequence SEQ ID NO:10, amino acid sequence SEQ ID NO:12, amino acid sequence SEQ ID NO:15, amino acid sequence SEQ ID NO:17, amino acid sequence SEQ ID NO:20 and/or amino acid sequence SEQ ID NO:23, as well as proteins that are encoded by nucleic acid molecules that are allelic variants of the nucleic acid molecules that encode proteins having any of those SEQ ID NO's.

The present invention also relates to mimetopes of parasitic helminth P39 proteins as well as to isolated antibodies that selectively bind to parasitic helminth P39 proteins or mimetopes thereof. Also included are methods, including recombinant methods, to produce proteins, mimetopes and antibodies of the present invention.

Yet another embodiment of the present invention is a therapeutic composition that is capable of protecting an animal from disease caused by a parasitic helminth. Such a therapeutic composition includes one or more of the following protective compounds: an isolated parasitic helminth P39 protein or a mimetope thereof; an isolated parasitic helminth nucleic acid molecule that hybridizes under stringent hybridization conditions with a *Dirofilaria immitis* P39 gene, an *Onchocerca volvulus* P39 gene, and/or a *Brugia malayi* P39 gene; and an isolated antibody that selectively binds to a parasitic helminth P39 protein. A preferred therapeutic composition of the present invention also includes an excipient, an adjuvant and/or a carrier. Preferred P39 nucleic acid molecule compounds of the present invention include naked nucleic acid vaccines, recombinant virus vaccines and recombinant cell vaccines. Also included in the present invention is a method to protect an animal from disease caused by a parasitic helminth. The method includes the step of administering to the animal a therapeutic composition of the present invention.

Suitable parasitic helminths to use in the production (e.g., recombinant, natural, or synthetic production) of nucleic acid molecules, proteins and antibodies of the present invention include nematodes, cestodes and trematodes, with nematodes (such as filariid, ascarid, strongyle and trichostrongyle nematodes) being preferred, with filariids being more preferred, and with *D. immitis, O. volvulus,* and *B. malayi* being even more preferred.

Suitable and preferred parasitic helminths from which to protect animals are as disclosed for use in the production of nucleic acid molecules, proteins and antibodies of the present invention. As such, preferred diseases from which to protect animals include diseases caused by nematodes, cestodes and/or trematodes, with diseases caused by nematodes being more preferred targets, and with diseases caused by filariids being even more preferred targets. Particularly preferred diseases from which to protect animals include heartworm, onchocerciasis and filariasis.

BRIEF DESCRIPTION OF THE FIGURES

FIG. 1 shows Western blots of *D. immitis* proteins immunoreacted with canine sera derived from immune and non-immune dogs.

FIGS. 3A–B shows the results of SDS-PAGE on proteins labeled with S-35 methionine extracted from *D. immitis* L4 larvae and reacted with control and immune sera at various time points after immunization.

FIGS. 4A–B shows the results of proteins analyzed as set forth in FIG. 3, but wherein the larval surface proteins are labeled with I-125.

DETAILED DESCRIPTION OF THE INVENTION

Figure 2A:
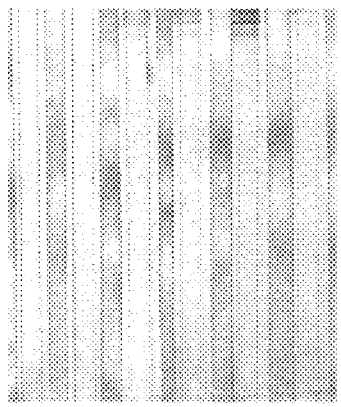
FIG. 2 shows Western blots of *D. immitis* proteins immunoreacted with canine sera at various time points (days) after immunization.
Figure 2B:
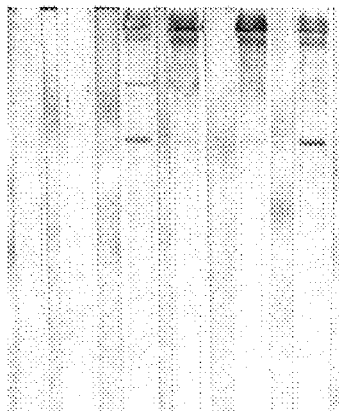
Figure 2C:
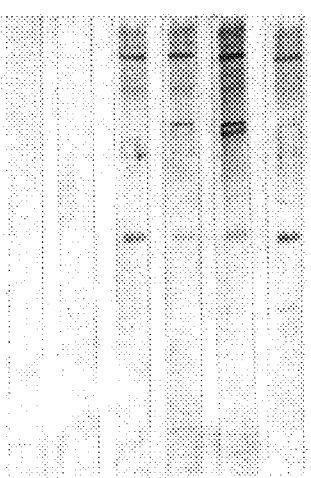
Figure 2D:
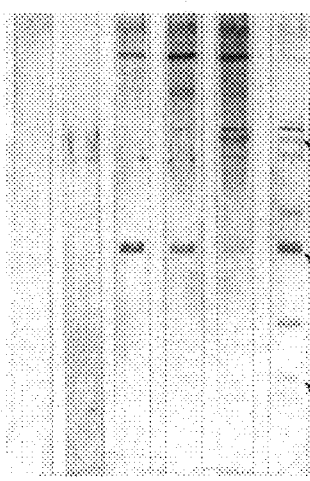
Figure 2E:
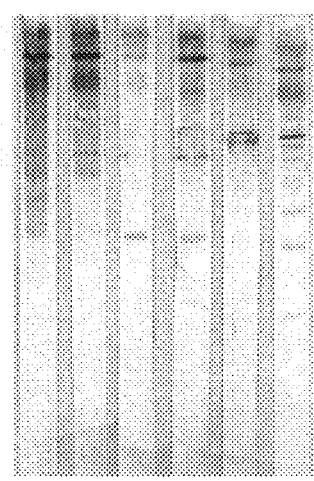

The present invention includes isolated parasitic helminth proteins that selectively bind to serum isolated from animals that are immune to parasitic heartworm infection. In particular, the present invention includes isolated *D. immitis* proteins of about 39 kD, as measured by Tris glycine SDS PAGE (i.e., polyacrylamide gel electrophoresis conducted in the presence of a Tris-glycine buffer containing sodium dodecyl sulfate), that selectively bind to serum isolated from dogs that are immune to heartworm infection. The present invention also includes nucleic acid molecules encoding such proteins and antibodies raised against such proteins. Also included is the use of serum collected from animals immune to parasitic helminth infection, *D. immitis* P39 proteins, *D. immitis* P39 nucleic acid molecules, and anti-*D. immitis* P39 antibodies to isolate additional parasitic helminth P39 proteins, nucleic acid molecules and antibodies. The present invention also includes the use of parasitic helminth P39 proteins, nucleic acid molecules and antibodies to protect animals from parasitic helminth diseases as well as in other applications, such as those disclosed below.

One embodiment of the present invention is an isolated parasitic helminth P39 protein. As used herein, a parasitic helminth P39 protein is a protein that is related to (i.e., bears structural similarity to) the *D. immitis* protein of about 39 kD, as measured by Tris glycine SDS PAGE, that selectively binds to immune dog serum. The original identification of such a protein is detailed in the Examples. A preferred parasitic helminth P39 protein is encoded by a nucleic acid molecule that hybridizes under stringent hybridization conditions to at least one of the following genes: (a) a gene encoding a *Dirofilaria immitis* P39 protein (i.e., a *D. immitis* P39 gene); (b) a gene encoding an *Onchocerca volvulus* P39 protein (i.e., an *O. volvulus* P39 gene); and (c) a gene encoding a *Brugia malayi* P39 protein (i.e., a *B. malayi* P39 gene). It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., *Molecular Cloning: A Laboratory Manual*, Cold Spring Harbor Labs Press, 1989. Examples of such conditions are provided in the Examples section of the present application.

As used herein, a *D. immitis* P39 gene includes all nucleic acid sequences related to a natural *D. immitis* P39 gene such as regulatory regions that control production of the *D. immitis* P39 protein encoded by that gene (such as, but not limited to, transcription, translation or post-translation control regions) as well as the coding region itself. In one embodiment, a *D. immitis* P39 gene includes the nucleic acid sequence SEQ ID NO:1. Nucleic acid sequence SEQ ID NO:1 represents the deduced sequence of a cDNA (complementary DNA) nucleic acid molecule denoted herein as nDiP39(1)$_{1185}$, the production of which is disclosed in the Examples. It should be noted that since nucleic acid sequencing technology is not entirely error-free, SEQ ID NO:1 (as well as other sequences presented herein), at best, represents an apparent nucleic acid sequence of the nucleic acid molecule encoding a *D. immitis* P39 protein of the present invention.

In another embodiment, a *D. immitis* P39 gene can be an allelic variant that includes a similar but not identical sequence to SEQ ID NO:1. An allelic variant of a *D. immitis* P39 gene including SEQ ID NO: 1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given parasitic helminth since the genome is diploid and/or among a population comprising two or more parasitic helminths. For example, it is believed that *D. immitis* nucleic acid molecule nDiP39(3)$_{1061}$, having nucleic acid sequence SEQ ID NO:8 and to be described in more detail below, represents an allelic variant of nDiP39(1)$_{1185}$.

Similarly, an *O. volvulus* P39 gene includes all nucleic acid sequences related to a natural *O. volvulus* P39 gene such as regulatory regions that control production of the *O. volvulus* P39 protein encoded by that gene as well as the coding region itself. In one embodiment, an *O. volvulus* P39 gene includes the nucleic acid sequence SEQ ID NO:11. Nucleic acid sequence SEQ ID NO:11 represents the deduced sequence of a cDNA nucleic acid molecule denoted herein as nOvP39$_{531}$, the production of which is disclosed in the Examples. In another embodiment, an *O. volvulus* P39 gene can be an allelic variant that includes a similar but not identical sequence to SEQ ID NO:11.

Similarly, a *B. malayi* P39 gene includes all nucleic acid sequences related to a natural *B. malayi* P39 gene such as regulatory regions that control production of the *B. malayi* P39 protein encoded by that gene as well as the coding region itself. In one embodiment, a *B. malayi* P39 gene includes the nucleic acid sequence SEQ ID NO:18. Nucleic acid sequence SEQ ID NO:18 represents the deduced sequence of a genomic nucleic acid molecule denoted herein as nBmP39$_{909}$, the production of which is disclosed in the Examples. In another embodiment, a *B. malayi* P39 gene can be an allelic variant that includes a similar but not identical sequence to SEQ ID NO:18.

According to the present invention, an isolated, or biologically pure, protein, is a protein that has been removed from its natural milieu. As such, "isolated" and "biologically pure" do not necessarily reflect the extent to which the protein has been purified. An isolated P39 protein of the present invention can be obtained from its natural source, can be produced using recombinant DNA technology or can be produced by chemical synthesis. As used herein, an isolated parasitic helminth P39 protein can be a full-length protein or any homologue of such a protein. Examples of P39 homologues include P39 proteins in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue includes at least one epitope capable of eliciting an immune response against a parasitic helminth P39 protein. That is, when the homologue is administered to an animal as an immunogen, using techniques known to those skilled in the art, the animal will produce a humoral and/or cellular immune response against at least one epitope of a parasitic helminth P39 protein. P39 homologues can also be selected by their ability to selectively bind to immune serum. Methods to measure such activities are disclosed herein.

Parasitic helminth P39 protein homologues can be the result of natural allelic variation or natural mutation. P39 protein homologues of the present invention can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to elicit an immune response against parasitic helminth P39 proteins. Examples of such identification techniques are disclosed herein.

Isolated parasitic helminth P39 proteins and mimetopes thereof of the present invention preferably are capable of selectively binding to serum collected from an animal that is immune to infection by the helminth, the serum being capable of inhibiting helminth development; that is, the protein is immunoreactive with at least one component in immune serum which is validated as protective in an immune host using, for example, the method disclosed in Grieve et al. in WO 92/13560, ibid. The ability of such proteins and mimetopes to selectively bind to components in such a serum is believed to suggest the ability of such proteins and mimetopes to protect an animal from parasite infection when such proteins and/or mimetopes are administered to an animal in an effective manner.

Animals that are immune to infection by parasitic helminths are animals that exhibit an immune response that is sufficient to protect the animal from such infection. Immune animals typically are animals that have been administered larval, adult and/or microfilarial helminths in a manner effective to elicit a protective response, preferably using irradiated helminths or a chemically-abbreviated infection protocol. For example, dogs receiving chemically abbreviated *D. immitis* larval infections exhibit significant immunity to challenge infections. Furthermore, sera obtained from such dogs are effective in passively transferring larval killing and stunting capabilities to mice. Preferred immune animals are those that have been immunized against helminth larvae, particularly against L3 and/or L4 larvae, since, in accordance with the present invention, it is particularly desirable to prevent L3 larvae introduced into an animal from developing into adult parasites. It should be noted, however, that immune animals do not preclude naturally-infected animals that generate protective antibodies.

In accordance with the present invention, a mimetope refers to any compound that is able to mimic the ability of an isolated parasitic helminth P39 protein of the present invention to selectively bind to anti-parasitic helminth immune serum (i.e., to bind to at least one component in immune serum that is protective against parasitic helminths) and/or to elicit an immune response against a parasitic helminth P39 protein of the present invention. A mimetope can be a peptide that has been modified to decrease its susceptibility to degradation but that still retains its selective binding ability. Other examples of mimetopes include, but are not limited to, anti-idiotypic antibodies or fragments thereof, that include at least one binding site that mimics one or more epitopes of an isolated protein of the present invention; non-proteinaceous immunogenic portions of an isolated protein (e.g., carbohydrate structures); and synthetic or natural organic molecules, including nucleic acids, that have a structure similar to at least one epitope of an isolated protein of the present invention. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

As used herein, the term "selectively binds to" immune serum refers to the ability of isolated proteins and mimetopes thereof to bind to serum collected from animals that are immune to parasitic helminth infection but essentially not to bind, according to standard detection techniques (such as those described in Sambrook et al., *Molecular Cloning: A Laboratory Manual*, Cold Spring Harbor Labs Press, 1989) to serum collected from animals that are not immune to parasitic helminth infection. Preferably, the isolated proteins and mimetopes are able to bind to anti-parasitic helminth immune serum with high affinity. The ability of a protein or mimetope thereof to selectively bind to anti-parasitic helminth immune serum can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy. It should be noted that the ability of an isolated protein or mimetope thereof to selectively bind to immune serum raised against a certain stage of helminth development does not preclude the isolated protein or mimetope from being able to also bind to immune serum raised against other stages of helminth development. For example, the ability of an isolated protein or mimetope thereof to selectively bind to an anti-larval immune serum does not preclude the isolated protein or mimetope from being able to also bind to anti- microfilarial and/or anti-adult immune serum.

As used herein, the phrases "capable of selectively binding to at least one component of a serum collected from an animal that is immune to infection by the helminth", "capable of selectively binding to immune serum", and "specifically immunoreactive with validated components of immune host serum or tissue" have similar meanings. "Validated components" are components which have been shown in the method of the invention, as described herein, to exert a deleterious effect on parasitic nematodes when supplied in a diffusion chamber to a host which has been administered the component. By "specifically immunoreactive" is meant that the immunogen is capable of binding the validated component as derived from an immune susceptible host, but is incapable of binding components found in nonimmune counterparts in this species. By "susceptible host" is meant a host species that is ordinarily susceptible to infestation by the nematode parasite in question. Individual members of the susceptible host species may have acquired immunity to this infestation.

One embodiment of the present invention is the use of anti-parasitic helminth immune serum to identify isolated proteins and mimetopes of the present invention, a technique referred to herein as an immune serum screening assay. Immune serum can be raised against a parasitic helminth by administering the helminth to an animal under conditions that elicit an immune response. Immune serum can be raised against larval, microfilarial, and/or adult helminths, preferably against larvae, and more preferably against L3 and/or L4 larvae. Immune sera of the present invention are capable not only of inhibiting development of the species of helminth that elicited the immune response, but also of helminth species that immunologically cross-react with the immune sera. Due to the similarity between helminths, immune sera of the present invention are capable of reacting with a large variety of helminths. Inhibiting the development of helminths includes killing, reducing the growth of, blocking the maturation of, altering the morphology of, altering the metabolism of, and/or otherwise being detrimental to the helminth.

Any animal that is capable of mounting an immune response to protect itself from helminth infection is a suitable animal to which helminths can be administered and from which immune serum can be collected. For example, a preferred animal from which to collect serum capable of inhibiting the development of *D. immitis* is a dog that has been administered L3 and/or L4 *D. immitis* larvae under conditions that elicit an immune response.

The ability of immune serum of the present invention to inhibit parasitic helminth development can be determined in a number of ways. A preferred method to monitor the ability of immune serum to inhibit the development of an infectious agent is disclosed by Grieve et al., WO 92/13560, ibid., and in the Examples. As disclosed therein, for example, the ability of an anti-parasitic helminth larval immune serum to inhibit larval development can be determined as follows. Briefly, a naive animal (i.e., an animal not previously exposed to parasitic helminth larvae) is implanted with at least one diffusion chamber containing helminth larvae, preferably L3 larvae. The animal is also administered either the anti-larval immune serum to be tested or a control non-immune serum, preferably at a site near the diffusion chambers. After a suitable period of time, for example, from about three to about four weeks for *D. immitis* larvae implanted in mice, the diffusion chambers are removed, and the effects of the immune serum on larval growth and development are determined by, for example, comparing larval growth and survival in chambers exposed to anti-larval immune serum with the growth and survival of larvae in diffusion chambers exposed to non-immune serum. A significant number of larvae exposed to anti-larval immune serum are either killed or stunted compared to larvae exposed to non-immune serum.

Grieve et al., WO 92/13560, ibid., further discloses use of the immune serum screening assay to screen for, and hence identify, desired proteins that selectively bind to the immune serum. Briefly, the immune serum can be contacted with a protein-containing composition under conditions that permit selective binding by desired proteins to components in the serum. Complexes between the proteins and serum components are recovered, the proteins are separated from the serum components and are then analyzed. Nucleic acid sequences encoding such proteins can be identified using known recombinant DNA techniques, such as those described in Sambrook et al., ibid. In another embodiment, the immune serum screening assay can be used to identify nucleic acid sequences encoding isolated proteins of the present invention by screening parasite helminth expression cDNA libraries with immune sera of the present invention to identify proteins expressed by individual clones that are capable of selectively binding to the immune sera. The immune serum screening assay can also be used to identify mimetopes capable of selectively binding to immune serum, such as to anti-L3 and/or L4 larval immune serum. Mimetopes can also be designed or improved using information derived from proteins identified by the immune serum screening assay. It should be appreciated that not only serum, but also other immunogenic components of bodily fluids collected from animals immune to helminth infection, such as cells, specific antibodies, and fragments thereof, can be used in the immune serum screening assay.

As disclosed in Grieve et al., WO 92/13560, ibid., anti-larval immune serum has been used to identify nematode *D. immitis* proteins expressed during L3 and/or L4 that have molecular weights of 66 kD, 65 kD, 59 kD, 39 kD, 33 kD, 23/24 kD, 22/20.5 kD and 14 kD, as determined by their migration patterns when subjected to Tris-glycine SDS PAGE.

The minimal size of a parasitic helminth P39 protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of a nucleic acid molecule such nucleic acid molecules is typically at least about 12 to about 15 nucleotides in length if the nucleic acid molecules are GC-rich and at least about 15 to about 17 bases in length if they are AT-rich.

As such, the minimal size of a nucleic acid molecule used to encode a P39 protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a P39 protein homologue of the present invention is from about 4 to about 6 amino acids in length, with preferred sizes depending on whether a full-length, fusion, multivalent, or functional portions of such proteins are desired.

Parasitic helminth proteins of the present invention, including homologues thereof, preferably are capable of eliciting an immune response against a parasitic helminth P39 protein and/or of selectively binding to immune serum. The minimum size of such a protein is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

Any parasitic helminth P39 protein is a suitable protein of the present invention. Suitable parasitic helminths from which to isolate P39 proteins (including isolation of the natural protein or production of the protein by recombinant or synthetic techniques) include nematodes, cestodes, and trematodes, with tissue-migrating nematodes being preferred. Preferred nematodes from which to isolate P39 proteins include filariid, ascarid, strongyle and trichostrongyle nematodes. Particularly preferred nematodes are those of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred nematodes include parasitic helminths of the genera Capillaria, Chabertia, Cooperia, Enterobius, Haemonchus, Nematodirus, Oesophagostomum, Ostertagia, Trichostrongylus and Trichuris. Preferred filariid nematodes include Dirofilaria, Onchocerca, Acanthocheilonema, Brugia, Dipetalonema, Loa, Parafilaria, Setaria, Stephanofilaria and *Wuchereria filariid* nematodes. Particularly preferred parasitic helminths are nematodes of the genera Dirofilaria, Onchocerca, and Brugia. A preferred Dirofilaria species is *D. immitis,* which causes heartworm. Preferred Onchocerca species include *O. volvulus* (which infects humans), *O. lienalis* (which infects cattle), *O. gutterosa* (which infects cattle), *O. gibsoni* (which infects cattle), *O. ochengi* (which infects cattle) and *O. cervicalis* (which infects horses), with *O. volvulus* being more preferred. Preferred Brugia species include *B. malayi* (which infects humans) and *B. pahangi* (which infects cats), with *B. malayi* being more preferred.

A preferred parasitic helminth P39 protein of the present invention is a compound that when administered to an animal in an effective manner, is capable of protecting that animal from disease caused by a parasitic helminth. As such, the parasitic helminth is incapable (i.e., essentially unable) of causing disease in an animal that is immunized with a parasitic helminth P39 protein of the present invention. In accordance with the present invention, the ability of a P39 protein of the present invention to protect an animal from disease by a parasitic helminth refers to the ability of that protein to treat, ameliorate and/or prevent disease, including infection leading to disease, caused by the parasitic helminth, preferably by eliciting an immune response against the parasitic helminth. As used herein, an immune response can include humoral and/or cellular immune responses.

Suitable parasites to target include any parasite that is incapable of causing disease in an animal administered a P39 protein of the present invention. As such, a parasite to target includes any parasite that produces a protein having one or more epitopes that can be targeted by a humoral and/or cellular immune response against a P39 protein of the present invention. Suitable and preferred parasites to target include those parasitic helminths disclosed above as being useful in the production of parasitic helminth proteins of the present invention.

One embodiment of the present invention is a fusion protein that includes a parasitic helminth P39 protein-containing domain attached to a fusion segment. Inclusion of a fusion segment as part of a P39 protein of the present invention can enhance the protein's stability during production, storage and/or use. Depending on the segment's characteristics, a fusion segment can also act as an immunopotentiator to enhance the immune response mounted by an animal immunized with a parasitic helminth P39 protein containing such a fusion segment. Furthermore, a fusion segment can function as a tool to simplify purification of a parasitic helminth P39 protein, such as to enable purification of the resultant fusion protein using affinity chromatography. A suitable fusion segment can be a domain of any size that has the desired function (e.g., imparts increased stability, imparts increased immunogenicity to a protein, and/or simplifies purification of a protein). It is within the scope of the present invention to use one or more fusion segments. Fusion segments can be joined to amino and/or carboxyl termini of the P39-containing domain of the protein. Linkages between fusion segments and P39-containing domains of fusion proteins can be susceptible to cleavage in order to enable straight-forward recovery of the P39-containing domains of such proteins. Fusion proteins are preferably produced by culturing a recombinant cell transformed with a fusion nucleic acid molecule that encodes a protein including the fusion segment attached to either the carboxyl and/or amino terminal end of a P39-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include PβGAL-PDiP39(1)$_{300}$, PβGAL-PDiP39(3)$_{300}$ and PHIS-PDiP39(3)$_{300}$, production of which are disclosed herein.

Another embodiment of the present invention is a parasitic helminth P39 protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a P39 protein of the present invention attached to one or more compounds protective against one or more other infectious agents, particularly an agent that infects humans, cats, dogs, cattle or horses, such as, but not limited to: viruses (e.g., caliciviruses, distemper viruses, hepatitis viruses, herpesviruses, immunodeficiency viruses, infectious peritonitis viruses, leukemia viruses, panleukopenia viruses, parvoviruses, rabies viruses, other cancercausing or cancer-related viruses); bacteria (e.g., Leptospira, Rochalimaea); fungi and fungal-related microorganisms (e.g., Candida, Cryptococcus, Histoplasma); and other parasites (e.g., Babesia, Cryptosporidium, Eimeria, Encephalitozoon, Hepatozoon, Isospora, Microsporidia, Neospora, Nosema, Plasmodium, Pneumocystis, Toxoplasma, as well as helminth parasites, such as those disclosed herein). In one embodiment, a *D. immitis* P39 protein of the present invention is attached to one or more additional compounds protective against heartworm. In another embodiment, an *O. volvulus* P39 protein of the present invention is attached to one or more additional compounds protective against onchocerciasis. In yet another embodiment, a *B. malayi* P39 protein of the present invention is attached to one or more additional compounds protective against filariasis.

A preferred parasitic helminth P39 protein of the present invention is a protein encoded by a nucleic acid molecule that hybridizes under stringent hybridization conditions with nucleic acid molecule $nDiP39(1)_{1185}$, $nDiP39(3)_{1061}$, $nOvP39_{531}$, and $nBmP39_{909}$. Such a P39 protein is encoded by a nucleic acid molecule that hybridizes under stringent hybridization conditions with a nucleic acid molecule having nucleic acid sequence SEQ ID NO:1, a nucleic acid molecule having nucleic acid sequence SEQ ID NO:8, a nucleic acid molecule having nucleic acid sequence SEQ ID NO:11, and/or SEQ ID NO:18.

Translation of SEQ ID NO:1 suggests that *D. immitis* nucleic acid molecule $nDiP39(1)_{1185}$ includes 2 open reading frames. The larger open reading frame encodes a *D. immitis* P39 protein of about 300 amino acids, referred to herein as $PDiP39(1)_{300}$ (the deduced amino acid sequence of which is represented herein as SEQ ID NO:2), assuming an open reading frame having an initiation (start) codon spanning from about nucleotide 216 through about nucleotide 218 of SEQ ID NO:1 and a termination (stop) codon spanning from about nucleotide 1116 through about nucleotide 1118 of SEQ ID NO:1. This open reading frame, excluding the stop codon, is referred to herein as nucleic acid molecule $nDiP39(1)_{900}$, the nucleic acid sequence of which is represented herein as SEQ ID NO:3. The calculated molecular weight of $PDiP39(1)_{300}$ is about 34.3 kD. PDiP39 $(1)_{300}$ has a calculated pI of about 4.68.

It is to be noted that the open frame of $nDiP39(1)_{1185}$ extends an additional 12 nucleotides upstream from the first ATG codon. This latter open reading frame, excluding the stop codon, is referred to herein as nucleic acid molecule $nDiP39(1)_{912}$, which has a nucleic acid sequence represented herein as SEQ ID NO:4, and which encodes a protein of about 304 amino acids, denoted herein as $PDiP39(1)_{304}$, the deduced amino acid sequence of which is represented herein as SEQ ID NO:5.

The smaller of the two open reading frames spans from about nucleotide 1 through about nucleotide 216, with a stop codon spanning from about nucleotide 217 through about nucleotide 219. The open reading frame, excluding the stop codon, is referred to herein as nucleic acid molecule $nDiP39(1)_{216}$, the nucleic acid sequence of which is represented herein as SEQ ID NO:6. Nucleic acid molecule $nDiP39(1)_{216}$ encodes a protein of about 72 amino acids, the deduced amino acid sequence of which is represented herein as SEQ ID NO:7.

Translation of SEQ ID NO:8 suggests that *D. immitis* nucleic acid molecule $nDiP39(3)_{1061}$ represents an allelic variant of $nDiP39(3)_{1185}$. Not only does $nDiP39(3)_{1061}$ lack the first 125 nucleotides of $nDiP39(1)_{1185}$, but $nDiP39(3)_{1061}$ also includes an extra "A" after nucleotide 203, as numbered for SEQ ID NO:1. Nucleic acid molecule nDiP39 $(3)_{1061}$ includes an open reading frame that encodes a *D. immitis* P39 protein of about 300 amino acids, referred to herein as $PDiP39(3)_{300}$ and having the same deduced amino acid sequence as does $PDiP39(1)_{300}$ (i.e., SEQ ID NO:2), assuming an open reading frame having an initiation (start) codon spanning from about nucleotide 92 through about nucleotide 94 of SEQ ID NO:8 and a termination (stop) codon spanning from about nucleotide 992 through about nucleotide 994 of SEQ ID NO:8. This open reading frame, excluding the stop codon, is referred to herein as nucleic acid molecule $nDiP39(3)_{900}$, the nucleic acid sequence of which is the same as that of $nDiP39(1)_{900}$, that being SEQ ID NO:3.

Due to the extra "A" at about position 79 of SEQ ID NO:8, however, $nDiP39(3)_{1061}$ has an uninterrupted open reading frame that extends from about nucleotide 2 through the stop codon spanning from about nucleotide 992 through about nucleotide 994 of SEQ ID NO:8 in the same reading frame as the open reading frame for the 300-amino acid $PDiP39(3)_{300}$ protein. The longer open reading frame, excluding the stop codon, is referred to herein as nucleic acid molecule $nDiP39(3)_{990}$, which has a nucleic acid sequence represented herein as SEQ ID NO:9, and which encodes a protein of about 330 amino acids, denoted herein as $PDiP39(3)_{330}$, the deduced amino acid sequence of which is represented herein as SEQ ID NO:10. Of particular interest is the extent of similarity between the first 30 amino acids of $PDiP39(3)_{330}$ and the last 30 amino acids of $PDiP39(1)_{72}$, the protein encoded by the smaller reading frame of SEQ ID NO:1, there being about 100% identity for the first 26 of the 30 amino acids. The calculated molecular weight of $PDiP39(3)_{330}$ is about 39.8 kD. $PDiP39(3)_{330}$ has a calculated pI of about 4.75.

Translation of SEQ ID NO:11 suggests that *O. volvulus* nucleic acid molecule $nOvP39_{531}$ has a structure similar to that of *D. immitis* $nDiP39(1)_{1185}$, except that $nOvP39_{531}$ is truncated at a position corresponding to about nucleotide 529 of SEQ ID NO:1. Similar to $nDiP39(1)_{1185}$, *O. volvulus* nucleic acid molecule $nOvP39_{531}$ includes 2 open reading frames. The open reading frame of $nOvP39_{531}$ that corresponds to the amino terminal third of $nDiP39(1)_{900}$ and $nDiP39(3)_{900}$ encodes a truncated *O. volvulus* P39 protein of about 104 amino acids, referred to herein as $POvP39_{104}$ (the deduced amino acid sequence of which is represented herein as SEQ ID NO:12), assuming an open reading frame having an initiation (start) codon spanning from about nucleotide 218 through about nucleotide 220 of SEQ ID NO:11 and ending at the last codon in $nOvP39_{531}$. This open reading frame is referred to herein as nucleic acid molecule $nOvP39_{312}$, the nucleic acid sequence of which is represented herein as SEQ ID NO:13.

It is to be noted that the open frame of $nOvP39_{531}$ including $nOvP39_{312}$ extends an additional 33 nucleotides upstream from the first ATG codon. This longer open reading frame is referred to herein as nucleic acid molecule $nOvP39_{345}$, which has a nucleic acid sequence represented herein as SEQ ID NO:14, and which encodes a protein of about 115 amino acids, denoted herein as $POvP39_{115}$, the deduced amino acid sequence of which is represented herein as SEQ ID NO:15.

The other independent open reading frame spans from about nucleotide 1 through about nucleotide 210, with a stop codon spanning from about nucleotide 211 through about nucleotide 213. This open reading frame is referred to herein as nucleic acid molecule $nOvP39_{210}$, the nucleic acid sequence of which is represented herein as SEQ ID NO:16. Nucleic acid molecule nOvP39$_{210}$ encodes a protein of about 70 amino acids, the deduced amino acid sequence of which is represented herein as SEQ ID NO:17.

Translation of SEQ ID NO:18 and comparing that sequence with SEQ ID NO:1 suggests that *B. malayi* nucleic acid molecule nBmP39$_{909}$ includes an extended open reading frame similar to that of *D. immitis* nDiP39(3)$_{1061}$, except that nBmP39$_{909}$ is truncated at a position corresponding to about nucleotide 405 of SEQ ID NO:8 (corresponds to about nucleotide 529 of SEQ ID NO:1). *B. malayi* nucleic acid molecule nBmP39$_{909}$, being a genomic DNA molecule, also includes 3 introns. As such, nBmP39$_{909}$ includes (in linear, contiguous order): (a) an open reading frame spanning from about nucleotide 1 through about nucleotide 32, (b) an about 106-nucleotide intron, (c) an open reading frame spanning from about nucleotide 139 through about nucleotide 257, (d) an about 161-nucleotide intron, (e) an open reading frame spanning from about nucleotide 419 through about nucleotide 681, (f) an about 106-nucleotide intron, and (g) an open reading frame spanning from about nucleotide 788 through about nucleotide 909.

A nucleic acid molecule containing a contiguous open reading frame of about 536 nucleotides derived from nBmP39$_{909}$ is denoted herein as nBmP39$_{536}$, and has nucleic acid sequence SEQ ID NO:19. The open reading frame of nBmP39$_{536}$ that corresponds to the amino terminal third of nDiP39(1)$_{900}$ and nDiP39(3)$_{900}$, as well as to nOvP39$_{312}$, encodes a truncated *B. malayi* P39 protein of about 105 amino acids, referred to herein as PBmP39$_{105}$ (the deduced amino acid sequence of which is represented herein as SEQ ID NO:20), assuming an open reading frame having an initiation (start) codon spanning from about nucleotide 220 through about nucleotide 222 of SEQ ID NO:19 and ending at the last codon in nBmP39$_{536}$. This open reading frame is referred to herein as nucleic acid molecule nBmP39$_{315}$, the nucleic acid sequence of which is represented herein as SEQ ID NO:21.

Similar to *D. immitis* nDiP39(3)$_{1061}$, *B. malayi* nBmP39$_{536}$ has an uninterrupted open reading frame that extends from about nucleotide 1 through about nucleotide 534 of SEQ ID NO:19 in the same reading frame as the open reading frame for the 105-amino acid PBmP39$_{105}$ protein. The longer open reading frame is referred to herein as nucleic acid molecule nBmP39$_{534}$, which has a nucleic acid sequence represented herein as SEQ ID NO:22, and which encodes a protein of about 178 amino acids, denoted herein as PBmP39$_{178}$, the deduced amino acid sequence of which is represented herein as SEQ ID NO:23.

Comparison of the *D. immitis*, *O. volvulus*, and *B. malayi* P39 nucleic acid sequences and amino acid sequences indicates that the three species of filariids possess similar P39 genes and proteins. Specifically, the nucleic acid sequence of *O. volvulus* P39 nucleic acid molecule nOvP39$_{531}$ (SEQ ID NO:11) is about 89% identical to the corresponding region of *D. immitis* P39 nucleic acid molecule nDiP39(1)$_{1185}$ (i.e., spanning from about nucleotide 22 through about nucleotide 509 of SEQ ID NO:1 (in this and other comparative analyses, the ends of the molecules comprising the primers were not included in determining percent identity)). The amino acid sequence of *O. volvulus* P39 protein POvP39$_{70}$ (i.e., SEQ ID NO:17), encoded by nOvP39$_{210}$, is about 82% identical to the corresponding region of *D. immitis* P39 protein PDiP39(1)$_{72}$ (i.e., SEQ ID NO:7), encoded by nDiP39(1)$_{216}$. The amino acid sequence of *O. volvulus* P39 protein POvP39$_{104}$ (i.e., SEQ ID NO:12), encoded by nOvP39$_{312}$, is about 81% identical to the corresponding region of *D. immitis* P39 protein PDiP39(1)$_{300}$ (i.e., spanning from about amino acid 1 through about amino acid 98 of SEQ ID NO:2), encoded by nDiP39(1)$_{900}$.

The nucleic acid sequence of *B. malayi* P39 nucleic acid molecule nBmP39$_{536}$ (SEQ ID NO:19) is about 80% identical to the corresponding region of *D. immitis* P39 nucleic acid molecule nDiP39(1)$_{1185}$ (i.e., spanning from about nucleotide 22 through about nucleotide 509 of SEQ ID NO:1). The amino acid sequence of *B. malayi* P39 protein PBmP39$_{178}$ (i.e., SEQ ID NO:23) from about amino acid 1 through about amino acid 73 is about 66% identical to the corresponding region of *D. immitis* P39 protein PDiP39(1)$_{72}$ (i.e., SEQ ID NO:7). The amino acid sequence of *B. malayi* P39 protein PBmP39$_{105}$ (i.e., SEQ ID NO:20), encoded by nBmP39$_{315}$, is about 76% identical to the corresponding region of *D. immitis* P39 protein PDiP39(1)$_{300}$ (i.e., spanning from about amino acid 1 through about amino acid 98 of SEQ ID NO:2).

Finding this degree of identity between *D. immitis*, *O. volvulus*, and *B. malayi* P39 nucleic acid sequences and amino acid sequences supports the ability to obtain any parasitic helminth P39 protein and nucleic acid molecule given the protein and nucleic acid sequences disclosed herein. It is to be noted that while the clones containing *D. immitis* nucleic acid molecules nDiP39(1)$_{1185}$ and nDiP39(3)$_{1061}$ were identified by screening with immune serum, *O. volvulus* nucleic acid molecule nOvP39$_{531}$ and *B. malayi* nucleic acid molecule nBmP39$_{909}$ were each obtained using oligonucleotide primers based on the nucleic acid sequences of *D. immitis* P39 nucleic acid molecules. Details are provided in the Examples.

Comparison of the deduced *D. immitis*, *O. volvulus*, and *B. malayi* P39 amino acid sequences with known nucleic acid and protein sequences indicates that there are no sequences in the data base showing similarity to any of the *D. immitis*, *O. volvulus*, *B. malayi* P39 amino acid sequences. As such, these parasitic helminth P39 proteins, and the nucleic acid molecules that encode them, represent novel compounds with utility in protecting an animal from diseases caused by parasitic helminths.

Preferred parasitic helminth P39 proteins of the present invention include proteins comprising amino acid sequences that are at least about 30%, preferably at least about 50%, more preferably at least about 75% and even more preferably at least about 90% identical to one or more of the amino acid sequences disclosed herein for *D. immitis*, *O. volvulus*, and *B. malayi* P39 proteins of the present invention. More preferred parasitic helminth P39 proteins of the present invention include: proteins encoded by at least a portion of SEQ ID NO:1 and, as such, have amino acid sequences that include at least a portion of SEQ ID NO:2, SEQ ID NO: 5 and/or SEQ ID NO: 7; proteins encoded by at least a portion of SEQ ID NO:8 and, as such, have amino acid sequences that include at least a portion of SEQ ID NO:2 and/or SEQ ID NO:10; proteins encoded by at least a portion of SEQ ID NO:11 and, as such, have amino acid sequences that include at least a portion of SEQ ID NO:12, SEQ ID NO:15 and/or SEQ ID NO:17; and proteins encoded by at least a portion of SEQ ID NO:19 and, as such, have amino acid sequences that include at least a portion of SEQ ID NO:20 and/or SEQ ID NO:23.

Particularly preferred parasitic helminth proteins of the present invention are proteins that include SEQ ID NO:2, SEQ ID NO:5, SEQ ID NO:7, SEQ ID NO:10, SEQ ID NO:12, SEQ ID NO:15, SEQ ID NO:17, SEQ ID NO:20 and/or SEQ ID NO:23 (including, but not limited to the encoded proteins, full-length proteins, processed proteins, fusion proteins and multivalent proteins thereof) as well as proteins that are truncated homologues of proteins that include at least portions of the aforementioned SEQ ID NOs. Even more preferred proteins include $PDiP39(1)_{304}$, $PDiP39(1)_{300}$, $PDiP39(1)_{72}$, $PDiP39(3)_{330}$, $PDiP39(3)_{300}$, $POvP39_{115}$, $POvP39_{104}$, $POvP39_{70}$, $PBmP39_{178}$, $PBmP39_{105}$, $P\beta GAL\text{-}PDiP39(1)_{300}$, $P\beta GAL\text{-}PDiP39(3)_{300}$ and $PHIS\text{-}PDiP39(3)_{300}$. Examples of methods to produce such proteins are disclosed herein, including in the Examples section.

One embodiment of the present invention is an isolated parasitic helminth nucleic acid molecule that hybridizes under stringent hybridization conditions with at least one of the following genes: a *D. immitis* P39 gene, an *O. volvulus* P39 gene, and a *B. malayi* P39 gene. The identifying characteristics of such genes are heretofore described. A nucleic acid molecule of the present invention can include an isolated natural parasitic helminth P39 gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with one of the aforementioned genes under stringent hybridization conditions. Suitable and preferred parasitic helminths are disclosed above.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated parasitic helminth P39 nucleic acid molecule of the present invention can be obtained from its natural source either as an entire (i.e., complete) gene or a portion thereof capable of forming a stable hybrid with that gene. An isolated parasitic helminth P39 nucleic acid molecule can also be produced using recombinant DNA technology (e.g., polymerase chain reaction (PCR) amplification, cloning) or chemical synthesis. Isolated parasitic helminth P39 nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a parasitic helminth P39 protein of the present invention or to form stable hybrids under stringent conditions with natural gene isolates.

A parasitic helminth P39 nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., ability to elicit an immune response against at least one epitope of a parasitic helminth P39 protein, ability to bind to immune serum) and/or by hybridization with a *D. immitis* P39 gene, with an *O. volvulus* P39 gene, and/or with a *B. malayi* P39 gene.

An isolated nucleic acid molecule of the present invention can include a nucleic acid sequence that encodes at least one parasitic helminth P39 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth P39 protein. As heretofore disclosed, parasitic helminth P39 proteins of the present invention include, but are not limited to, proteins having full-length parasitic helminth P39 coding regions, proteins having partial parasitic helminth P39 coding regions, fusion proteins, multivalent protective proteins and combinations thereof.

At least certain nucleic acid molecules of the present invention encode proteins that selectively bind to immune serum (i.e., to immune serum) derived from an animal that is immune to infection by the parasitic helminth from which the nucleic acid molecule was isolated. The immune serum is preferably derived from an animal immunized with a composition comprising parasitic helminth third stage and/or fourth stage larvae. Examples of such nucleic acid molecules include, but are not limited to, nucleic acid molecules $nDiP39(1)_{1185}$ and $nDiP39(3)_{1061}$.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, the nucleic acid molecule being delivered to the animal by direct injection (i.e., as a naked nucleic acid) or in a vehicle such as a recombinant virus vaccine or a recombinant cell vaccine.

One embodiment of the present invention is a parasitic helminth P39 nucleic acid molecule that hybridizes under stringent hybridization conditions with at least one of the following nucleic acid molecules: $nDiP39(1)_{1185}$, $nDiP39(3)_{1061}$, $nOvP39_{531}$, and $nBmP39_{909}$. Such parasitic helminth nucleic acid molecules can hybridize under stringent hybridization conditions with a nucleic acid molecule having nucleic acid sequence SEQ ID NO:1, with a nucleic acid molecule having nucleic acid sequence SEQ ID NO:8, with a nucleic acid molecule having nucleic acid sequence SEQ ID NO:11, and with a nucleic acid molecule having nucleic acid sequence SEQ ID NO:18. Preferred parasitic helminth nucleic acid molecules include nucleic acid molecules having a nucleic acid sequence that is at least about 50%, preferably at least about 70%, more preferably at least about 80%, and even more preferably at least about 90% identical to nucleic acid sequences SEQ ID NO:1, SEQ ID NO:8, SEQ ID NO:11 and SEQ ID NO:18.

A preferred nucleic acid molecule of the present invention includes at least a portion of nucleic acid sequence SEQ ID NO:1, SEQ ID NO: 8, SEQ ID NO: 11 and/or SEQ ID NO: 18 that is capable of hybridizing (i.e., the hybridizes under stringent hybridization conditions) to a *D. immitis* P39 gene, to an *O. volvulus* P39 gene, and/or to a *B. malayi* P39 gene of the present invention. More preferred is a nucleic acid molecule that includes nucleic acid sequence SEQ ID NO:1, nucleic acid sequence SEQ ID NO:3, nucleic acid sequence SEQ ID NO:4, nucleic acid sequence SEQ ID NO:6, nucleic acid sequence SEQ ID NO:8, nucleic acid sequence SEQ ID NO:9, nucleic acid sequence SEQ ID NO:11, nucleic acid sequence SEQ ID NO:13, nucleic acid sequence SEQ ID NO:14, nucleic acid sequence SEQ ID NO:16, nucleic acid sequence SEQ ID NO:18, nucleic acid sequence SEQ ID NO:19, nucleic acid sequence SEQ ID NO:21, and/or nucleic acid sequence SEQ ID NO:22, as well as a nucleic acid molecule that is an allelic variant of any of those nucleic acid molecules. Such preferred nucleic acid molecules can include nucleotides in addition to those included in the SEQ ID NOs, such as, but not limited to, a full-length gene, a full-length coding region, a nucleic acid molecule encoding a fusion protein, and/or a nucleic acid molecule encoding a multivalent protective compound. Particularly preferred nucleic acid molecules include $nDiP39(1)_{1185}$, $nDiP39(1)_{912}$, $nDiP39(1)_{900}$, $nDiP39(1)_{216}$, $nDiP39(1)_{910}$, $nDiP39(3)_{1061}$, $nDiP39(3)_{990}$, $nDiP39(3)_{900}$, $nDiP39(3)_{910}$, $nOvP39_{531}$, $nOvP39_{345}$, $nOvP39_{312}$, $nOvP39_{210}$, $nBmP39_{909}$, $nBmP39_{536}$, $nBmP39_{534}$, and $nBmP39_{315}$.

The present invention also includes nucleic acid molecules encoding a protein including at least a portion of SEQ ID NO:2, nucleic acid molecules encoding a protein having at least a portion of SEQ ID NO:5, nucleic acid molecules encoding a protein having at least a portion of SEQ ID NO:7, nucleic acid molecules encoding a protein having at least a portion of SEQ ID NO:10, nucleic acid molecules encoding a protein having at least a portion of SEQ ID NO:12, nucleic acid molecules encoding a protein having at least a portion of SEQ ID NO:15, nucleic acid molecules encoding a protein having at least a portion of SEQ ID NO:17, nucleic acid molecules encoding a protein having at least a portion of SEQ ID NO:20, and/or nucleic acid molecules encoding a protein having at least a portion of SEQ ID NO:23, including nucleic acid molecules that have been modified to accommodate codon usage properties of the cells in which such nucleic acid molecules are to be expressed.

Knowing the nucleic acid sequences of certain parasitic helminth P39 nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain P39 nucleic acid molecules for other parasitic helminths, particularly since, as described in detail in the Examples section, knowledge of *D. immitis* P39 nucleic acid molecules of the present invention enabled the isolation of *O. volvulus* and *B. malayi* P39 nucleic acid molecules of the present invention. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include parasitic helminth L3 and/or L4 larval libraries as well as genomic DNA libraries. Similarly, preferred DNA sources to screen or from which to amplify nucleic acid molecules include parasitic helminth L3 and/or L4 larval DNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising parasitic helminth P39 genes or other parasitic helminth P39 nucleic acid molecules. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit P39 protein production or activity. Such therapeutic applications include the use of such oligonucleotides in, for example, antisense-, triplex formation-, ribozyme- and/or RNA drug-based technologies. The present invention, therefore, includes such oligonucleotides and methods to protect animals from diseases caused by parasitic helminths by use of one or more of such technologies. Appropriate oligonucleotide-containing therapeutic compositions can be administered to an animal, using techniques known to those skilled in the art, either prior to or after infection by a parasitic helminth, such as *D. immitis*, *O. volvulus*, or *B. malayi*, in order to protect the animal from disease.

The present invention also includes a recombinant vector, which includes at least one parasitic helminth P39 nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule (s) are derived. The vector can be either RNA or DNA, either prokaryotic or eukaryotic, and typically is a virus or a plasmid. Recombinant vectors can be used in the cloning, sequencing, and/or otherwise manipulating of parasitic helminth P39 nucleic acid molecules of the present invention. One type of recombinant vector, referred to herein as a recombinant molecule and described in more detail below, can be used in the expression of nucleic acid molecules of the present invention. Preferred recombinant vectors are capable of replicating in the transformed cell.

Suitable and preferred nucleic acid molecules to include in recombinant vectors of the present invention are as disclosed herein for suitable and preferred parasitic helminth P39 nucleic acid molecules per se. Particularly preferred nucleic acid molecules to include in recombinant vectors, and particularly in recombinant molecules, of the present invention include $nDiP39(1)_{1185}$, $nDiP39(1)_{912}$, $nDiP39(1)_{900}$, $nDiP39(1)_{216}$, $nDiP39(1)_{910}$, $nDiP39(3)_{1061}$, $nDiP39(3)_{990}$, $nDiP39(3)_{900}$, $nDiP39(3)_{910}$, $nOvP39_{531}$, $nOvP39_{345}$, $nOvP39_{312}$, $nOvP39_{210}$, $nBmP39_{909}$, $nBmP39_{536}$, $nBmP39_{534}$, and $nBmP39_{315}$.

Isolated parasitic helminth P39 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred parasitic helminth P39 nucleic acid molecules per se. Particularly preferred nucleic acid molecules to include in recombinant cells of the present invention include $nDiP39(1)_{1185}$, $nDiP39(1)_{912}$, $nDiP39(1)_{900}$, $nDiP39(1)_{216}$, $nDiP39(1)_{910}$, $nDiP39(3)_{1061}$, $nDiP39(3)_{990}$, $nDiP39(3)_{900}$, $nDiP39(3)_{910}$, $nOvP39_{531}$, $nOvP39_{345}$, $nOvP39_{312}$, $nOvP39_{210}$, $nBmP39_{909}$, $nBmP39_{536}$, $nBmP39_{534}$, and $nBmP39_{315}$.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing parasitic helminth P39 proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_\chi$3987 and SR-11 $_\chi$4072: *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types heretofore disclosed.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments and fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Suitable signal segments include natural signal segments or any heterologous signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, $\alpha$-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, poxvirus, adenovirus, cytomegalovirus (such as intermediate early promoters, simian virus 40, retrovirus, actin, retroviral long terminal repeat, *Rous sarcoma* virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a parasitic helminth, such as a *D. immitis, O. volvulus* or *B. malayi* molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include pβgal-nDiP39(1)$_{1185}$, pβgal-nDiP39(3)$_{1061}$, pHis-nDiP39(3)$_{910}$, pSP-nDiP39(3)$_{910}$, pBV-nDiP39(3)$_{910}$, pSV-nDiP39(3)$_{910}$, pPVXC-nDiP39(1)$_{910}$ and pPVXRC-nDiP39(1)$_{910}$. Details regarding the production of such recombinant molecules are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include *E. coli*:pβgal-nDiP39(1)$_{1185}$, *E. coli*:pβgal-nDiP39(3)$_{1061}$), *E. coli*:pHis-nDiP39(3)$_{910}$, *E. coli*:pSP-nDiP39(3)$_{910}$, *S. frugiperda*:pBV-nDiP39(3)$_{910}$, and BHK:pSV-nDiP39(3)$_{910}$. Details regarding the production of these recombinant cells are disclosed herein.

Recombinant cells of the present invention can also be co-transformed with one or more recombinant molecules including parasitic helminth P39 nucleic acid molecules encoding one or more proteins of the present invention and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a parasitic helminth P39 protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli;* or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a parasitic helminth P39 protein of the present invention or to a mimetope thereof. Such antibodies are also referred to herein as anti-parasitic helminth P39 antibodies. Particularly preferred antibodies of this embodiment include anti-*D. immitis* P39 antibodies, anti-*O. volvulus* P39 antibodies, and anti-*B. malayi* P39 antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid. An anti-parasitic helminth P39 antibody preferably binds to a parasitic helminth P39 protein in such a way as to reduce the activity of that protein.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce parasitic helminth P39 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art. Suitable cytotoxic agents include, but are not limited to: double-chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but lack the toxin's intrinsic cell binding domain.

One embodiment of the present invention is a therapeutic composition that, when administered to an animal in an effective manner, is capable of protecting that animal from disease caused by a parasitic helminth. Therapeutic compositions of the present invention include at least one of the following protective compounds: (a) an isolated P39 protein or a mimetope thereof; (b) an isolated parasitic helminth nucleic acid molecule that hybridizes under stringent hybridization conditions with a gene selected from the group consisting of a *Dirofilaria immitis* P39 gene, an *Onchocerca volvulus* P39 gene, and a *Brugia malayi* P39 gene; (c) an isolated antibody that selectively binds to a parasitic helminth P39 protein; and (d) a mixture (i.e., combination) of at least two of the compounds. As used herein, a protective compound refers to a compound that, when administered to an animal in an effective manner, is able to treat, ameliorate, and/or prevent disease caused by a parasitic helminth of the present invention. Preferred helminths to target are heretofore disclosed. Examples of proteins, nucleic acid molecules, antibodies and methods to identify inhibitors of the present invention are disclosed herein.

The present invention also includes a therapeutic composition comprising at least one parasitic helminth P39-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm include dogs, cats, humans and ferrets, with dogs and cats being particularly preferred. Preferred animals to protect against onchocerciasis include humans, cattle and horses, with humans being particularly preferred. Preferred animals to protect against filariasis and other diseases caused by Brugia helminths include humans, cats and other felines.

In one embodiment, a therapeutic composition of the present invention can be administered to the vector in which the parasitic helminth develops, such as to a mosquito in order to prevent the spread of heartworm and/or filariasis or to a black fly in order to prevent the spread of onchocerciasis. Such administration could be orally or by developing transgenic vectors capable of producing at least one therapeutic composition of the present invention. In another embodiment, a vector, such as a mosquito or a black fly, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax™ adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from disease caused by a parasitic helminth of the present invention, a therapeutic composition of the present invention is administered to the animal in an effective manner such that the composition is capable of protecting that animal from a disease caused by a parasitic helminth. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of parasitic helminth P39 proteins in order to interfere with development of parasitic helminths targeted in accordance with the present invention.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. Such a vaccine can comprise any nucleic acid molecule or recombinant molecule of the present invention. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences, such as that of bovine growth hormone, are also preferred. Examples of nucleic acid vaccine embodiments include pPVXC-nDiP39(1)$_{910}$ or pPVXRC-nDiP39(1)910.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccine ranges from about 1 nanogram (ng) to about 100 $\mu$g, depending on the route of administration and/or method of delivery, as can be determined by those skilled in the art. Suitable delivery methods include, for example, by injection, as drops, aerosolized and/or topically. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

A recombinant virus vaccine of the present invention includes a recombinant molecule of the present invention that is packaged in a viral coat and that can be expressed in an animal after administration. Preferably, the recombinant molecule is packaging-deficient. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), species-specific herpesviruses and species-specific poxviruses. Methods to produce and use recombinant virus vaccines are disclosed in PCT Publication No. WO 94/17813, by Xiong et al., published Aug. 18, 1994, which is incorporated by reference herein in its entirety. Examples of recombinant virus vaccines of the present invention are disclosed in the Examples section.

When administered to an animal, a recombinant virus vaccine of the present invention infects cells within the immunized animal and directs the production of a protective protein or RNA nucleic acid molecule that is capable of protecting the animal from disease caused by a parasitic helminths as disclosed herein. For example, a recombinant virus vaccine comprising a *D. immitis* P39 nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells that express at least one protein of the present invention. Preferred recombinant cells for use in this embodiment include Salmonella, *E. coli,* Listeria, Mycobacterium, *S. frugiperda,* BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells or cell lysates.

In common with most other enteric pathogens, Salmonella strains normally enter the host orally. Once in the intestine, they interact with the mucosal surface, normally to establish an invasive infection. Most Salmonella infections are controlled at the epithelial surface, causing the typical Salmonella-induced gastroenteritis. Some strains of Salmonella, including *S. typhi* and some *S. typhimurium* isolates, have evolved the ability to penetrate deeper into the host, causing a disseminated systemic infection. It appears such strains have the capacity to resist the killing actions of macrophages and other immune cells. *S. typhi* can exist for long periods as a facultative intracellular parasite. Some of the live vaccine strains can also persist for long periods in the mononuclear phagocyte system. Hosts infected in such a manner develop, in addition to a mucosal immune response, systemic cellular and serum antibody responses to the Salmonella. Thus, invading Salmonella, whether virulent or attenuated, can stimulate strong immune responses, unlike many other enteric pathogens which only set up local, noninvasive gut infections. The potent immunogenicity of live Salmonella makes them attractive candidates for carrying parasitic helminth P39 nucleic acid molecules and proteins of the present invention to the immune system.

A preferred recombinant cell-based vaccine is one in which the cell is attenuated. *Salmonella typhimurium* strains, for example, can be attenuated by introducing mutations into genes critical for in vivo growth and survival. For example, genes encoding cyclic adenosine monophosphate (cAMP) receptor protein or adenylate cyclase are deleted to produce avirulent, vaccine strains. Such strains can deliver antigens to lymphoid tissue in the gut but demonstrate reduced capacity to invade the spleen and mesenteric lymph nodes. These strains are still capable of stimulating both humoral and cellular immunity in mammalian hosts.

Recombinant cell vaccines can be used to introduce parasitic helminth P39 proteins of the present invention into the immune systems of animals. For example, recombinant molecules comprising parasitic helminth nucleic acid molecules of the present invention operatively linked to expression vectors that function in Salmonella can be transformed into Salmonella host cells. The resultant recombinant cells are then introduced into the animal to be protected. Preferred Salmonella host cells are those for which survival depends on their ability to maintain the recombinant molecule (i.e., a balanced-lethal host-vector system). An example of such a preferred host/recombinant molecule combination is a Salmonella strain (e.g., UK-1 $_{102}$ 3987 or SR-11 $_{\chi}$4072) which is unable to produce aspartate β-semialdehyde dehydrogenase in combination with a recombinant molecule also capable of encoding the enzyme. Aspartate β-semialdehyde dehydrogenase, encoded by the asd gene, is an important enzyme in the pathway to produce diaminopimelic acid (DAP). DAP is an essential component of the peptidoglycan of the cell wall of Gram-negative bacteria, such as Salmonella, and, as such, is necessary for survival of the cell. Thus, Salmonella lacking a functional asd gene can only survive if they maintain a recombinant molecule that is also capable of expressing a functional asd gene.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Such techniques are known to those skilled in the art.

One preferred embodiment of the present invention is the use of parasitic helminth P39 proteins, nucleic acid molecules and antibodies of the present invention, and particularly *D. immitis* P39 proteins, nucleic acid molecules and antibodies of the present invention, to protect an animal from heartworm. It is particularly preferred to prevent L3 larvae that are delivered to the animal by the mosquito intermediate host from maturing into adult worms. As such, preferred therapeutic compositions are those that are able to inhibit at least one step in the portion of the parasite's development cycle that includes L3 larvae, third molt, L4 larvae, fourth molt, immature adult prior to entering the circulatory system. In dogs, this portion of the development cycle is about 70 days. Particularly preferred therapeutic compositions include *D. immitis* P39-based therapeutic compositions of the present invention, particularly since P39 expression is apparently linked to L3 and L4 development. Such compositions include *D. immitis* P39 nucleic acid molecules, *D. immitis* P39 proteins and mimetopes thereof, and anti-*D. immitis* P39 antibodies. Such compositions are administered to animals in a manner effective to protect the animals from heartworm. Additional protection may be obtained by administering additional protective compounds, including other *D. immitis* proteins, nucleic acid molecules and antibodies.

Another preferred embodiment of the present invention is the use of parasitic helminth P39 proteins, nucleic acid molecules and antibodies of the present invention, and particularly *O. volvulus* P39 proteins, nucleic acid molecules and antibodies of the present invention, to protect a human from onchocerciasis. It is particularly preferred to prevent L3 larvae that are delivered to the animal by the black fly intermediate host from maturing into adult worms. Preferred therapeutic compositions are those that are able to inhibit at least one step in the portion of the parasite's development cycle that includes L3 larvae, third molt, L4 larvae, fourth molt and immature adult prior to entering the subcutaneous tissues. In humans infected with *O. volvulus,* this portion of the development cycle is about 150 days. As such, preferred therapeutic compositions include *O. volvulus* P39-based therapeutic compositions of the present invention, particularly since P39 expression is apparently linked to L3 and L4 development. Such compositions include *O. volvulus* P39 nucleic acid molecules, *O. volvulus* P39 proteins and mimetopes thereof, and anti-*O. volvulus* P39 antibodies. Such compositions are administered to humans in a manner effective to protect humans from onchocerciasis. Additional protection may be obtained by administering additional protective compounds, including other Onchocerca, preferably *O. volvulus,* proteins, nucleic acid molecules and antibodies.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle.

The following examples are provided for the purposes of illustration and are not intended to limit the scope of the present invention.

EXAMPLES

The following examples include a number of recombinant DNA and protein chemistry techniques known to those skilled in the art; see, for example, Sambrook et al., ibid.

Example 1

This Example describes a procedure for producing and evaluating immune sera of the present invention.

Four dogs were immunized with chemically-abbreviated *D. immitis* larval infections (using the method described in Grieve et al., 1988, *Am. J. Trop. Med. Hyg.* 39, 373–379), and two dogs served as chemically-treated controls. The dogs were housed in indoor mosquito-free individual cages at a temperature of about 22° C. and about 40% to about 65% humidity. On day 532, post initial immunization, each dog was challenged with about 100 L3 *D. immitis* larvae by implanting 5 diffusion chambers per dog, each diffusion chamber containing about 20 L3 *D. immitis* larvae, using the method described in Grieve et al., 1988, ibid. Concomitant with chamber implantation, each dog was injected subcutaneously with about 50 L3 *D. immitis* larvae, and the infection was allowed to proceed beyond the anticipated pre-patent period. Challenge infections were repeated on day 588, post initial immunization, both by implanting 5 diffusion chambers per dog, each chamber having about 20 L3 *D. immitis* larvae and by subcutaneously inoculating about 30 L3 *D. immitis* larvae per dog. Serum samples were collected from the immunized dogs at numerous time points throughout the study period. Serum samples were analyzed for antibodies that selectively bound to L3 and/or L4 surface antigens using an indirect fluorescent antibody assay, and for antibodies that selectively bound to L3 soluble antigens, L4 soluble antigens and/or to an excretory/secretory antigen fraction using an indirect ELISA, as described by Grieve et al., 1988, ibid. The results indicated that serum from dogs that had been immunized and challenged with *D. immitis* larvae had produced antibodies to both surface and soluble *D. immitis* larval antigens. The sera were pooled, and those obtained from larval-immunized dogs (i.e., anti-larval immune sera) were shown to inhibit larval development; see, for example, Example 2. Immune sera were also shown to selectively bind to L3 and/or L4 larval proteins having molecular weights of about 15 kD, 23/24 kD doublet, 31 kD, 33 kD, 39 kD, 42 kD, 55 kD, 59 kD, 66 kD, 70 kD, 97 kD and 207 kD by Tris-glycine SDS PAGE.

Example 2

This Example demonstrates that serum collected from larval-immunized dogs, produced as described in Example 1, is capable of inhibiting parasite development whereas serum collected from non-immunized dogs is not.

One subcutaneous pocket was formed in each of about 3 to about 6 Balb/C BYJ mice that were about 10 weeks old. One diffusion chamber, containing 20 L3 *D. immitis* larvae, was implanted into each pocket alone with 0.5 ml of sera collected from immunized dogs or from non-immunized dogs, produced as described in Example 1. The diffusion chambers were recovered two or three weeks later. Living larvae in the chambers were counted and placed into glacial acetic acid, followed by 70% ethanol containing 5% glycerin. The ethanol was allowed to evaporate leaving the larvae in glycerin. The larvae were measured using projected images in the Macmeasure image analysis system on a Macintosh computer.

Three experiments, in which different serum samples were exposed to larvae in diffusion chambers, were conducted: Experiment 1 compared equal portions of sera collected from individual dogs at days 56, 77 and 117 after challenge. Experiments 2 and 3 compared serum collected from immunized dogs 117 days after initial challenge to control sera. In experiment 2, the control serum was a pool of sera collected from 12 naive dogs; in experiment 3, control serum was collected from a single naive dog. Each of the experiments also included controls in which the larvae were not exposed to any serum.

In experiment 1, chambers were recovered two weeks post-inoculation. The number of larvae retrieved from chambers implanted in mice receiving serum from immunized (i.e., immune) dogs was lower than that of larvae in chambers implanted in mice receiving naive dog serum, but the difference was not statistically significant. Also, no differences were seen between the length of larvae regardless of which serum was used.

In experiments 2 and 3, the chambers were recovered three weeks after infection. There were significant differences in the larval recoveries between those receiving serum from naive dogs and those from immune dogs; there were about 34% more larvae recovered from mice treated with naive dog serum than were recovered from mice treated with immune serum. The lengths of the larvae were also significantly shorter in those chambers exposed to sera from immune dogs compared to larvae in chambers exposed to naive dog sera. Thus, this Example shows that serum collected from dogs immune to *D. immitis* infection inhibits larval development, compared to serum collected from naive dogs.

Example 3

This Example describes the identification of antigens that selectively bind to serum from a dog that is immune to heartworm infection.

Crude extracts of L4 larvae were prepared as follows: All procedures were performed at 4° C. or on ice. L4 worms were collected and washed twice with wash buffer (PBS/ 0.1% Triton X-100) and then with extraction buffer (0.05 M Tris/HCl, pH 6.8; 2% CHAPSO; 1 mM PMSF; 1 mM EDTA; 1 mg/l leupeptin; 1 mg/l pepstatin). (Other detergents may be used in place of CHAPSO, including 0.5% Triton X-100, 0.5% CTAB, 2% DOC, or 2% SDS/5% 2-ME/8 M urea.) The worms were then homogenized 5 times for 1 minute each, with 1 minute rest periods, using 250 $\mu$l to 500 $\mu$l of extraction buffer for 10,000–20,000 worms ($\neq$500 $\mu$g). This volume was transferred to an additional tube, and the homogenizer washed with a clean 100 $\mu$l to 250 $\mu$l of extraction buffer and the wash pooled with the homogenate. The tube was rocked from 4 hours to overnight and centrifuged at 12,000 g for 10 minutes. The supernatant was harvested and the pellet washed once with extraction buffer and saved for additional extractions if desired. The combined total volume of extract was less than 1 ml and about 20 ng of protein was solubilized per L4 larva used.

Crude extracts of L3 were prepared in the same manner, except that the wash buffer was PBS without detergent.

The extracts were subjected to polyacrylamide gel electrophoresis and tested with portions of the serum shown to be protective in the murine model. When pooled canine sera which had been shown to stunt larval growth as described in Example 2 were used as the immunoreactant in the Western blots, the results were as shown in FIG. 1. The 39 kD band shown in FIG. 1 is separated from a 45 kD band when a second dimension is added to the electrophoresis. This 45 kD protein is not immunoreactive. As seen, the serum is specifically immunoreactive with a 39 kD protein present in the L4 larval stage. This protein has a pI of about 5. Control serum shows no immunoreactivity with this protein. Reactivity to the 39 kD molecule is present in immune dogs, but not in control dogs. Sera from dogs with microfilaremic infection or amicrofilaremic infection do not recognize this molecule.

In addition, bands were present at 66 kD, 24/23 kD, and 14 kD, as shown in FIG. 2.

The proteins associated with the larval stages were also metabolically labeled using S-35 methionine; or the surfaces were labeled, prior to extraction, with I-125 or with biotin. For labeling with S-35 methionine, the radiolabeled amino acid was added to the parasites after 48 hrs in culture according to the method of Abraham et al., 1987, *J. Parasitol.* 73, 377– 383. For labeling with I-125, the method of Mok et al., 1988, *Molec. Biochem. Parasitol.* 31, 173–182 was used. For biotinylation, a modification of the method of Alvarez et al., 1989, *Molec. Biochem. Parasitol.* 33, 183–190, was employed. In the modified procedure, NHS-long chain biotin was substituted for biotin per se.

Figure 5A:
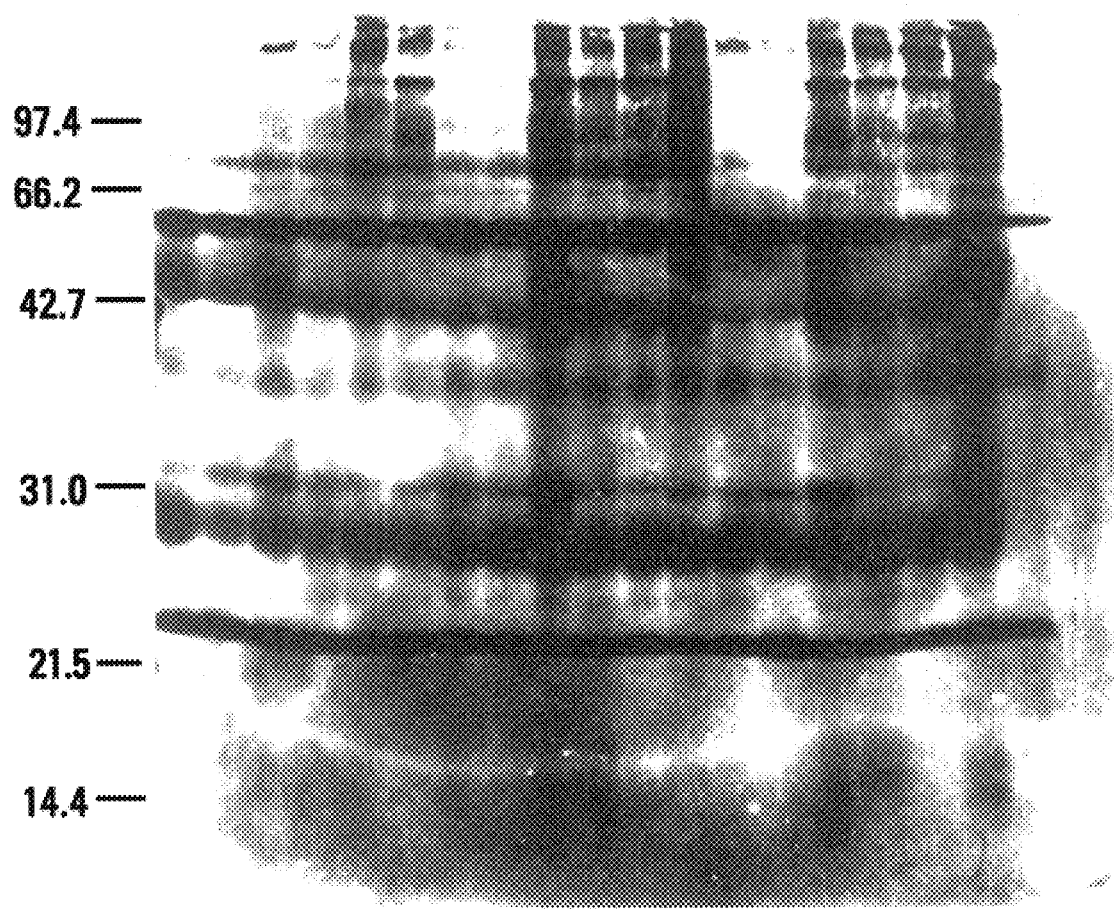
FIGS. 5A–B shows the results of proteins analyzed as in FIG. 3, but wherein the larval surface proteins are labeled using biotin.
Figure 5B:
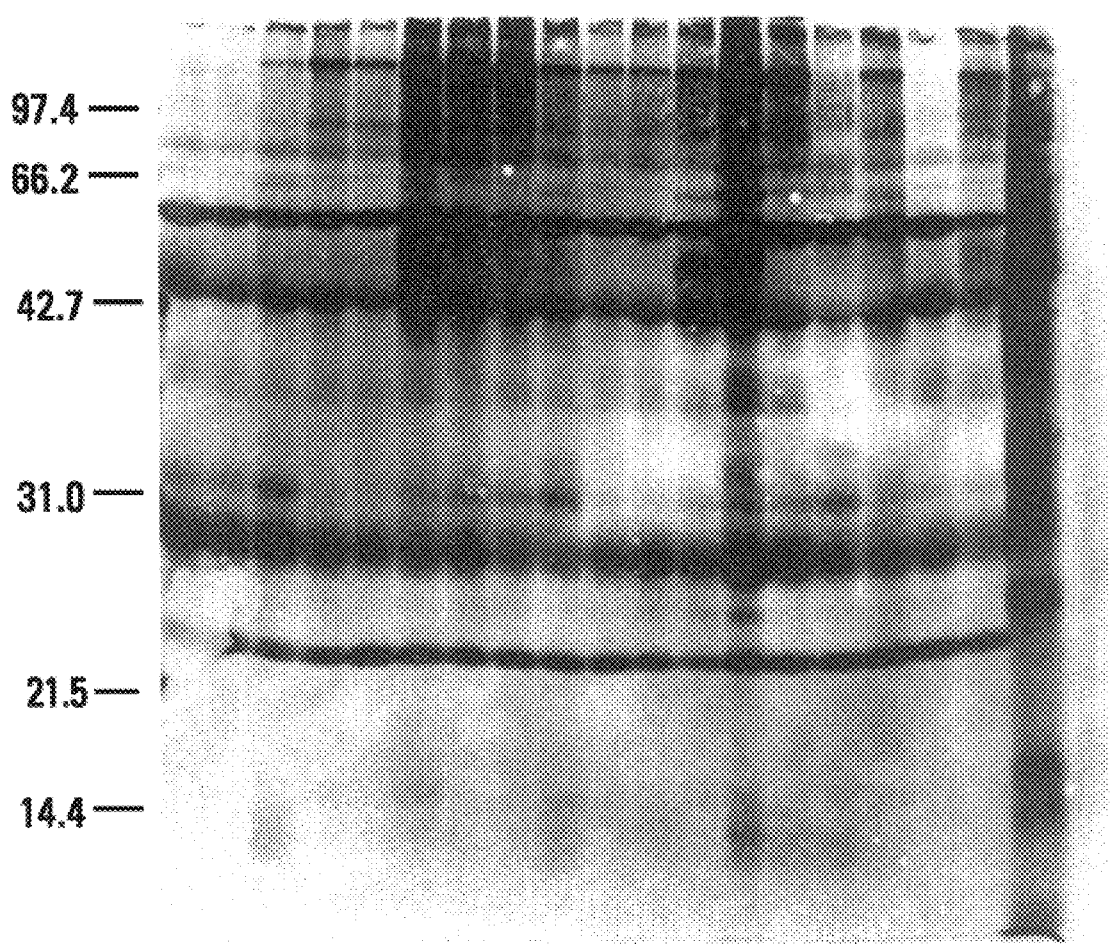

Thus, additional identification could be had using these prelabeled proteins which immunoprecipitated with the successfully validated immune serum. These results are shown in FIGS. 3, 4 and 5. As shown in FIG. 3, additional candidates are found at 59 kD and 16 kD, as indicated by the arrows. The radioactive iodine-labeled material shows a candidate at about 33 kD with a higher molecular weight smear at 35.8–34.5 kD. This was present beginning at day 345 and persisting until day 642 in some, but not all, immune dogs. An additional band was present at 14.5 kD. This is indicated in FIG. 4.

FIG. 5 shows the results when the proteins were labeled by biotinylation in an enhanced chemiluminescence assay. A transient band represented by 65.3 kD was recognized by 3 of 4 immune dogs.

In addition, passive transfer of the earliest immune dog serum which showed uniform responses to the 39 kD protein (i.e., the day-142 immune serum shown in FIG. 3) was able to effect killing of the entrapped larvae; recoveries of intact larvae were only 58.3% in the case of immune serum compared to 65.8% for controls.

To summarize, the following antigen candidates were obtained:

A 39 kD protein which reacted with sera from all immune dogs but not with sera from naive cohorts. The protein is shown to be present in Western blots obtained from L4 soluble antigen and solubilized L4 larval pellets and is shown to be present, although apparently to a lesser degree, in L3. This protein appears to be absent from adult *D. immitis* and the microfilariae. It is clearly a distinct protein from the p35 protein described by Scott et al., ibid., and P39 is relatively acidic, having a pI of approximately 5.

A 14 kD immunogen is detected with immune dog serum using Western blots and immunoprecipitation employing S-35 and iodine-labeled components. The protein is detected with immune dog serum, but not by serum from controls.

Additional proteins detected are of 66 kD and 23/24 kD.

Figure 6:
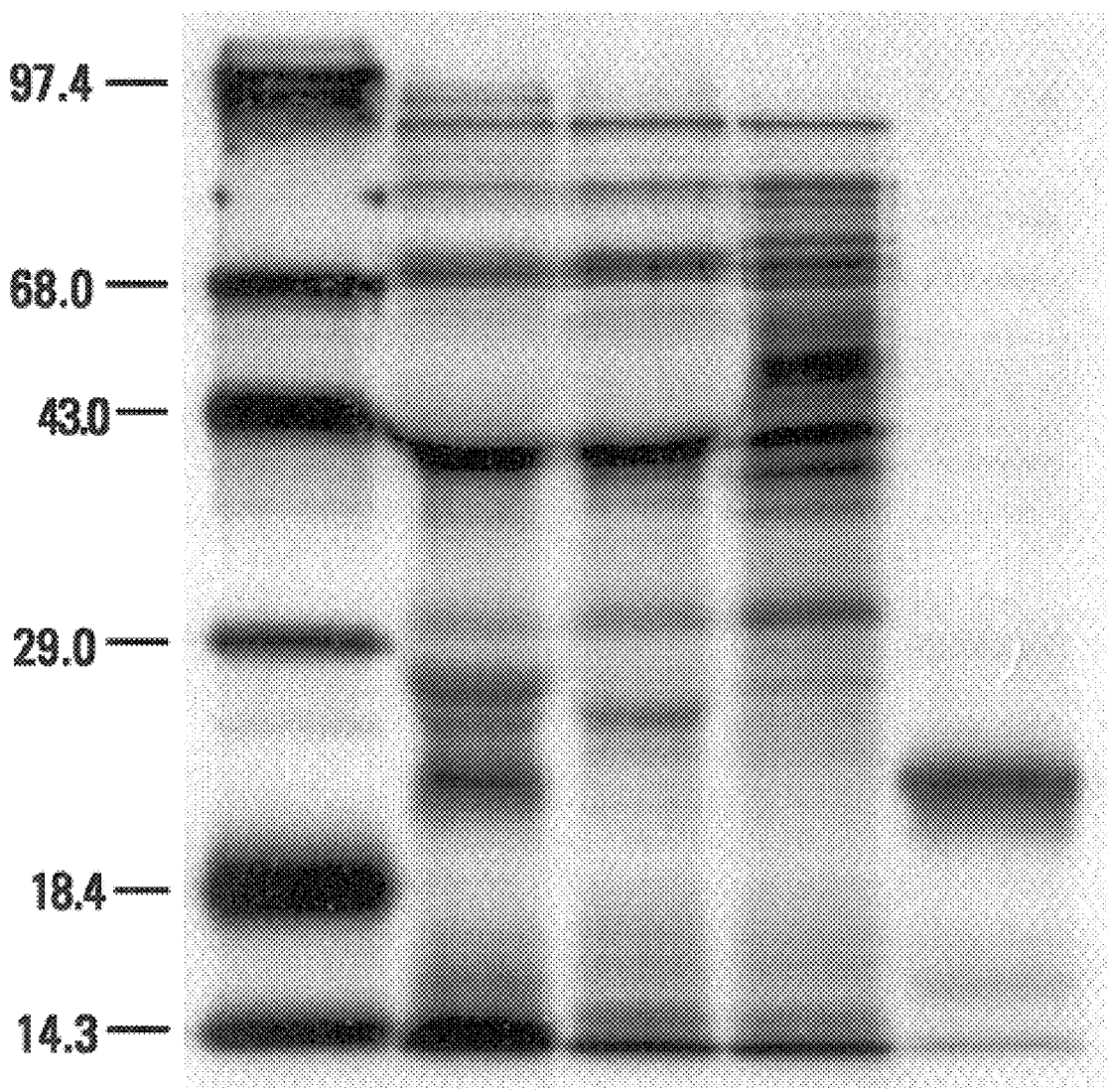
FIG. 6 shows the results of analysis of proteins present in the excretory/secretory material which characterizes the transition from L3 to L4 and maintenance of L4s for 3–4 days thereafter.

Another potential source of protective antigens in parasitic diseases are excretory/secretory products which are associated with various stages of the parasite. The transition between L3 and L4 involves excretion/secretion of a number of proteins which were harvested as follows: Larvae were cultured at 250–400/ml, washed at 48 hr and cultured an additional 4 days. The worms were then settled out and the supernatant collected. The supernatant was filtered through a 0.45 $\mu$m filter and protease inhibitors added as in L4 solubilization. The ES was then concentrated and buffer exchanged by ultrafiltration over a 10 kD membrane (Amicon Centriprep-10 and/or Centricon-10). The final buffer was 0.05 M Tris/HCl pH 6.8 with protease inhibitors. Yields may be about 5 ng of protein per larva, frequently in a final volume of 150 $\mu$l to 250 $\mu$l. This extract, referred to as DILEX, was prepared using larvae which were metabolically labeled with S-35 methionine and tested with respect to immune and control sera from dogs. The immune serum was that obtained on day 554 post immunization as set forth in Example 1. Immunoprecipitation with respect to the immune serum was obtained at 22/20.5 kD and 14.3 kD, as shown in FIG. 6. In FIG. 6, lane 1 shows molecular weight standards; lane 2, the immunoprecipitates from immune dog; lane 3, from control dog; lane 4, bead control; and lane 5, DILEX itself.

Example 4

This Example describes the cloning and sequence of a *D. immitis* P39 nucleic acid molecule (also referred to as *D. immitis* nucleic acid sequence p39) that was identified by its ability to encode a protein that selectively bound to at least one component of immune serum collected from a dog immunized with *D. immitis* larvae.

Genomic and cDNA expression libraries in λZapII (Short, J. M., et al., 1988, Nuc. Acids Res. 16, 7583–7600), a derivative of λgt11, were prepared from total genomic DNA, or L4 or L3 larval stage mRNAs, or male or female adult worms, respectively, using standard procedures (*Short Protocols in Molecular Biology*, 1989, Ausubel et al., (ed.). RNA samples were prepared as follows. *D. immitis* L3 or L4 larvae were harvested from mosquitos using standard techniques and cultivated in vitro in 50:50 NCTC-135/IMDM (NI) media (Sigma) supplemented with 20% serum supplement at 37° C., 5% carbon dioxide for 48 hours or 6 days, respectively. Adult worms were collected from dogs at necropsy, separated by gender, immediately washed three times in NI medium at 37° C., snap frozen in sterile 15 ml conical tubes in liquid nitrogen and ground to a fine powder in liquid nitrogen. Total RNA was extracted from the larvae and adult worms using an acid-guanidinium-phenol-chloroform method similar to that described by Chomczynski et al., 1987, *Anal. Biochem.* 162, 156–159. Approximately 15,000 to 30,000 larvae or about 13–15 adults were used in an RNA preparation. Poly A+ selected RNA was separated from total RNA by oligo-dT cellulose chromatography using Oligo dT cellulose from Collaborative Research, Inc., Waltham, Mass., according to the method recommended by the manufacturer.

In this example, four cDNA expression libraries were prepared from *D. immitis* adult female, adult male, 48 hour third stage (L3), and 6 day fourth stage (L4) larvae mRNA in lambda (λA) Uni-ZAP™ XR vector (available from Stratagene Cloning Systems, La Jolla, Calif.) using Stratagene's ZAP-cDNA Synthesis Kit® protocol and about 5 μg to about 6 μg of each of the respective poly A+ RNA samples. The resultant libraries were amplified one time and the titers were:
Adult male: $1.15 \times 10^{10}$ pfu/ml with 99% recombinants;
Adult female: $1.4 \times 10^9$ pfu/ml with 97% recombinants;
48 hour L3 larvae: $4.88 \times 10^9$ pfu/ml with 97% recombinants;
6 day L4 larvae: $1.05 \times 10^9$ pfu/ml with 98% recombinants.

Using the protocol described in the Stratagene picoBlue immunoscreening kit, the cDNA expression libraries were screened with pooled immune dog sera prepared as described in Example 1. Antibodies specific for a highly immunoreactive protein termed the "ladder protein" had been adsorbed from this serum by affinity chromatography.

Development of immunoblots containing adult female worm, and L3 or L4 larval protein lysates with the adsorbed sera showed reactivity to the previously recognized 39 kD protein and one other >100 kD protein only in the larval lysates. Immunoscreening of duplicate plaque lifts of the 48 hour L3 library with this sera identified 4 positive clones named p39-1 through p39-4. p39-4 has been renamed p4 and is described in greater detail in U.S. patent application Ser. No. 08/109,391, (U.S. Pat. No. 5,639,876) ibid. p39-1, p39-2 and p39-3 each represent p39 nucleic acid sequences that encode P39 proteins as defined herein.

An antibody select technique (Hall et al., 1984, *Nature* 311, 379–382) was used to obtain clone-specific antibodies for p39-1 and p39-3. Using the protocol described for library immunoscreening, two 90 mm agar plates, each containing $1.5 \times 10^4$ purified phage were overlaid with nitrocellulose filters, previously soaked in 10 mM IPTG. The plaque lifts were incubated overnight in immune dog sera prepared as described in Example 1 diluted 1:200 in TBS-1% gelatin, and washed 4× in TBST (20 mM Tris-HCl, pH 7.5, 150 mM NaCl, 0.05% Tween-20) and 2× in TBS (TBST without the Tween-20). Like filters were treated with 2.0 ml glycine buffer (0.1 M glycine-HCl, pH 2.6, 0.15 M NaCl) for 15 minutes on ice to elute clone-specific antibodies. The acidic eluate was immediately neutralized by the dropwise addition of 1 M Tris, pH 8.0. The clone-specific antibodies were concentrated in an Amicon centricon 30 microconcentrator and used to develop immunoblots of *D. immitis* adult female, and L3 and L4 larval proteins. Clone-specific antibodies eluted from clones p39-1 and p39-3 detected a single 39 kD larval specific protein that migrated at the same position as the larval 39 kD native protein selectively bound by immune dog serum. Antibodies selected from a non-recombinant phage showed no reactivity to the *D. immitis* proteins. These data indicate that these p39 recombinant clones encode the 39 kD protein selectively detected by immune dog sera. The clones identified as immunoreactive with the immune serum provide a source of DNA encoding desired proteins.

Plaque-purified clones including *D. immitis* P39 nucleic acid molecules were converted into double stranded recombinant molecules using R408 helper phage and XL1-Blue *E. coli* according to the in vivo excision protocol described in the Stratagene ZAP-cDNA Synthesis Kit. Double stranded plasmid DNAs were prepared using an alkaline lysis protocol, such as that described in Sambrook et al., ibid. Plasmid DNAs containing p39-1 and p39-2 were digested with EcoRI and XhoI restriction endonucleases to release two *D. immitis* DNA fragments of about 1000 and about 200 nucleotides, the entire *D. immitis* fragments each being about 1200 nucleotides in size. Digestion of plasmid DNAs containing p39-3 with EcoRI and XhoI restriction endonucleases released two *D. immitis* DNA fragments of about 1000 and about 60 nucleotides, the entire *D. immitis* fragment being about 1060 nucleotides in size.

Double stranded p39-1, p39-2 and p39-3 nucleic acid sequences were sequenced using the Sanger dideoxy chain termination method, as described in Sambrook et al., ibid. The Promega Erase a Base method (available from Promega Corp., Madison, Wis.) was used to generate deletion clones for sequence analysis. MacVector™ version 3.5 sequence analysis software (International Biotechnologies, Inc., New Haven, Conn.) was used for amino acid translations, protein molecular weight and isoelectric point calculations, and hydrophilicity calculations. The nucleic acid sequences of p39-1 and p39-2 were identical and are represented herein as SEQ ID NO:1. A nucleic acid molecule containing SEQ ID NO:1 is also referred to herein as nDiP39(1)$_{1185}$. Nucleic acid molecule p39-3, also referred to herein as nDiP39(3)$_{1061}$, has a nucleic acid sequence represented herein as SEQ ID NO:8. The nucleic acid sequence of nDiP39(3)$_{1061}$ is similar to that of nDiP39(1)$_{1185}$, except that nDiP39(3)$_{1061}$ lacks the first 125 nucleotides of nDiP39(1)$_{1185}$ and has an additional "A" after nucleotide 203 (referring to the numbering of SEQ ID NO:1).

Translation of SEQ ID NO:1 suggests that *D. immitis* nucleic acid molecule nDiP39(1)$_{1185}$ includes 2 open reading frames. The larger open reading frame encodes a *D. immitis* P39 protein of about 300 amino acids, referred to herein as PDiP39(1)$_{300}$ (the deduced amino acid sequence of which is represented herein as SEQ ID NO:2), assuming an open reading frame having an initiation (start) codon spanning from about nucleotide 216 through about nucleotide 218 of SEQ ID NO:1 and a termination (stop) codon spanning from about nucleotide 1116 through about nucleotide 1118 of SEQ ID NO:1. This open reading frame, excluding the stop codon, is referred to herein as nucleic acid molecule nDiP39(1)$_{900}$, the nucleic acid sequence of which is represented herein as SEQ ID NO:3. The calculated molecular weight of PDiP39(1)$_{300}$ is about 34.3 kD (i.e., 34,332 daltons). PDiP39(1)$_{300}$ has a calculated pI of about 4.68, which agrees reasonably well with the pI of the natural *D. immitis* protein subjected to isoelectric focussing, namely a pI of about 5.0.

It is to be noted that the open frame of nDiP39(1)$_{1185}$ extends an additional 12 nucleotides upstream from the first ATG codon. This latter open reading frame, excluding the stop codon, is referred to herein as nucleic acid molecule nDiP39(1)$_{912}$, which has a nucleic acid sequence represented herein as SEQ ID NO:4, and which encodes a protein of about 304 amino acids, denoted herein as PDiP39(1)$_{304}$, the deduced amino acid sequence of which is represented herein as SEQ ID NO:5.

The smaller of the two open reading frames spans from about nucleotide 1 through about nucleotide 216, with a stop codon spanning from about nucleotide 217 through about nucleotide 219. The open reading frame, excluding the stop codon, is referred to herein as nucleic acid molecule nDiP39(1)$_{216}$, the nucleic acid sequence of which is represented herein as SEQ ID NO:6. Nucleic acid molecule nDiP39(1)$_{216}$ encodes a protein of about 72 amino acids, the deduced amino acid sequence of which is represented herein as SEQ ID NO:7.

Translation of SEQ ID NO:8 suggests that *D. immitis* nucleic acid molecule nDiP39(3)$_{1061}$ represents an allelic variant of nDiP39(3)$_{1185}$. Not only does nDiP39(3)$_{1061}$ lack the first 125 nucleotides of nDiP39(1)$_{1185}$, but nDiP39(3)$_{1061}$ also includes an extra "A" after nucleotide 203, as numbered for SEQ ID NO:1. Nucleic acid molecule nDiP39(3)$_{1061}$ includes an open reading frame that encodes a *D. immitis* P39 protein of about 300 amino acids, referred to herein as PDiP39(3)$_{300}$ and having the same deduced amino acid sequence as does PDiP39(1)$_{300}$ (i.e., SEQ ID NO:2), assuming an open reading frame having an initiation (start) codon spanning from about nucleotide 92 through about nucleotide 94 of SEQ ID NO:8 and a termination (stop) codon spanning from about nucleotide 992 through about nucleotide 994 of SEQ ID NO:8. This open reading frame, excluding the stop codon, is referred to herein as nucleic acid molecule nDiP39(3)$_{900}$, the nucleic acid sequence of which is the same as that of nDiP39(1)$_{900}$, that being SEQ ID NO:3.

Due to the extra "A" at about position 79 of SEQ ID NO:8, however, nDiP39(3)$_{1061}$ has an uninterrupted open reading frame that extends from about nucleotide 2 through the stop codon spanning from about nucleotide 992 through about nucleotide 994 of SEQ ID NO:8 in the same reading frame as the open reading frame for the 300-amino acid PDiP39(3)$_{300}$ protein. The longer open reading frame, excluding the stop codon, is referred to herein as nucleic acid molecule nDiP39(3)$_{990}$, which has a nucleic acid sequence represented herein as SEQ ID NO:9, and which encodes a protein of about 330 amino acids, denoted herein as PDiP39(3)$_{330}$, the deduced amino acid sequence of which is represented herein as SEQ ID NO:10. Of particular interest is the extent of similarity between the first 30 amino acids of PDiP39(3)$_{330}$ and the last 30 amino acids of PDiP39(1)$_{72}$, the protein encoded by the smaller reading frame of SEQ ID NO:1, there being about 100% identity for the first 26 of the 30 amino acids. The calculated molecular weight of PDiP39(3)$_{330}$ is about 39.8 kD (i.e., 39,820 daltons). PDiP39(3)$_{330}$ has a calculated pI of about 4.75, which also agrees reasonably well with the pI of the natural *D. immitis* protein subjected to isoelectric focussing, namely, a pI of about 5.0.

Example 5

This Example also demonstrates the ability of a *D. immitis* P39 nucleic acid molecule to encode a protein that selectively binds to immune serum. Furthermore, monospecific antibodies that are selected by their ability to bind to the recombinant P39 protein are also capable of binding to 39-kD *D. immitis* L3 and L4 antigens.

Recombinant molecule pHis-nDiP39(3)$_{910}$ (also referred to as pHis-p39$_{910}$), containing *D. immitis* nucleotides from about 92 through about 1001 of SEQ ID NO:8 operatively linked to trc transcription control sequences and to a fusion sequence encoding a poly-histidine segment comprising 6 histidines was produced in the following manner. An about 910-nucleotide fragment containing nucleotides spanning from about nucleotide 92 through about nucleotide 1001 of SEQ ID No:8 (equivalent to a fragment spanning from about nucleotide 216 through about nucleotide 1125 of SEQ ID NO:1) was PCR amplified from nucleic acid molecule nDiP39(3)$_{1061}$ using the following primers: oligonucleotide 39CT, having the nucleic acid sequence 5' CGCGGATC-CCGCAAATGAGATCATG 3' (BamHI site in bold), represented herein as SEQ ID NO:24; and oligonucleotide 39COOH, having nucleic acid sequence 5' GCCAACG-GATCCATTCAGTCAACATACC 3' (BamHI site in bold), represented herein as SEQ ID NO:25. The resulting PCR product was digested with BamHI and subcloned into a BamHI digested, CIP (calf intestine phosphatase)-treated pTrcHisB vector (available from InVitrogen, Corp., San Diego, Calif.) to form recombinant molecule pHis-nDiP39(3)$_{910}$. Proper 5' to 3' orientation of the P39 nucleic acid molecule within the vector was verified. Recombinant molecule pHis-nDiP39(3)$_{910}$ was transformed into *E. coli* to form recombinant cell *E. coli*:pHis-nDiP39(3)$_{910}$.

Recombinant cell *E. coli*:pHis-nDiP39(3)$_{910}$ was cultured in shake flasks containing an enriched bacterial growth medium containing 0.1 mg/ml ampicillin at about 37° C. When the cells reached an OD$_{600}$ of about 0.3, expression of the encoded *D. immitis* P39 protein was induced by addition of about 1 mM IPTG. Protein production was monitored by SDS PAGE of recombinant cell lysates, followed by Coomassie blue staining, using standard techniques.

Recombinant cell *E. coli*:pHis-nDiP39(3)$_{910}$ produced a protein, denoted herein as PHIS-PDiP39(3)$_{300}$ (also referred to as PHIS-P39$_{900}$), that migrated with an apparent molecular weight of about 46 kD. Such a protein was not produced by cells transformed with the pTrcHisB plasmid lacking a *D. immitis* DNA insert.

Immunoblot analysis of recombinant cell *E. coli*:pHis-nDiP39(3)$_{910}$ lysates indicates that the 46-kD protein was able to selectively bind to immune dog serum and, as such, was capable of binding to at least one component of a serum that is capable of inhibiting *D. immitis* larval development.

Immune dog serum essentially did not bind to lysates of cells transformed with only the pTrcHisB plasmid.

Purified PHIS-PDiP39(3)$_{300}$ fusion protein was incubated with immune dog sera produced as in Example 1, the monospecific antibodies eluted from the protein and reacted with Western blots of *D. immitis* life stage specific antigens. The clone-specific antibodies recognized a 39-kD larval-specific antigen in 0-hr L3, 48-hr L3, and 6-day L4 antigen preparations but did not detect this protein in adult male, female or microfilaria preparations. These data verify the *D. immitis* P39 nucleic acid molecule encodes a larval specific 39 kD protein recognized by immune dog sera.

Example 6

This Example demonstrates the production of a P39 protein in eukaryotic cells as well as the production of a recombinant virus vaccine capable of expressing P39.

An intermediate recombinant molecule was produced in the following manner. An XhoI restriction site was added to a pSP64 vector (available from Promega) by linearizing pSP64 with SmaI, ligating an XhoI linker to one end, and recircularizing the vector with T4 DNA ligase to form pSP64-Xho. The pSP64-Xho vector was digested with BamHI, CIP-treated and ligated with *D. immitis* P39 nucleic acid molecule nDiP39(3)$_{910}$ which was released from recombinant molecule pHis-nDiP39(3)$_{910}$ by BamHI cleavage. The resultant molecule is referred to herein as pSP-nDiP39(3)$_{910}$ (also denoted p76-80.B3).

In order to subclone a *D. immitis* P39 nucleic acid molecule into baculovirus or Sindbis expression vectors, nDiP39(3)$_{910}$-containing fragments were PCR amplified from pSP-nDiP39(3)$_{910}$ using the following primers: an antisense primer denoted 76-58.B, having nucleic acid sequence 5' GTGGAATTGTGAGCGG 3', referred to herein as SEQ ID NO:26, which is homologous to pSP64 sequences located downstream of the nDiP39(3)$_{910}$ sequence; and an N-terminal primer designed from nDiP39 (3)$_{910}$ sequence with modifications to enhance expression in the individual systems. Specifically, the N-terminal primer 105-47.A, having nucleic acid sequence 5' GCGGGATC-CTATAAATATGATAGATTTGAAGAAG 3' (BamHI site in bold), referred to herein as SEQ ID NO:27, was used to generate an nDiP39(3)$_{910}$-containing PCR product, referred to as nBV/DiP39(3)$_{910}$ (also denoted SVp39), for subcloning into the baculovirus shuttle plasmid BlueBacIII (available from InVitrogen). An N-terminal primer 105-08.A, having nucleic acid sequence 5' GCTCTAGACCAT-GATAGATTTGAAGAAG 3' (XbaI site in bold), referred to herein as SEQ ID NO:28, was used to produce an nDiP39 (3)$_{910}$-containing PCR product, referred to as nSV/DiP39 (3)$_{910}$ (also denoted SVp39), for subcloning into the Sindbis virus shuttle plasmid Toto2J1-minus.

In order to produce a baculovirus recombinant molecule capable of directing the production of PDiP39(3)$_{300}$, nBV/DiP39(3)$_{910}$ was digested with BamHI and ligated into the unique BamHI site of BlueBacIII (available from InVitrogen) shuttle plasmid. The orientation of the insert was verified and the resultant recombinant molecule designated pBv-nDiP39(3)$_{910}$ (also referred to as p105-72.5C). This recombinant molecule and linear Baculogold baculovirus DNA (available from Pharmingen, San Diego, Calif.) were cotransfected into *Spodoptera frugiperda* Sf9 host cells (donated by the Colorado Bioprocessing Center, Fort Collins, Colo.) to form *S. frugiperda*:pBV-nDiP39(3)$_{910}$ (also referred to as *S. frugiperda*:p105-72.5C). The recombinant virus, vBV-nDiP39(3)$_{910}$, (also denoted 105-92.1), was verified for proper insert orientation and cultivated for increased production of recombinant virus and to verify expression of PDiP39(3)$_{300}$ by Western blot. Immunoblot analysis indicates that PDiP39(3)$_{300}$ produced using baculovirus vectors is capable of being selectively bound by immune sera isolated from Dog 93; the immune sera was prepared and isolated as described in Example 1.

In order to produce a recombinant virus particle vaccine in which PDiP39(3)$_{300}$ expression is under the control of a Sindbis virus promoter, nSV/DiP39(3)$_{910}$ was directionally ligated into the XbaI and XhoI restriction sites of Sindbis virus vector Toto2J1 following removal of the chloramphenicol acetyltransferase (CAT) gene from this location in the vector. The resulting recombinant molecule is denoted pSV-nDiP39(3)$_{910}$ (also referred to as p105-42.1A). Note that Toto2J1 is a Sindbis virus expression vector that contains the SP6 RNA polymerase promoter and the entire Sindbis virus genome through to the NsiI restriction site at nucleotide 11452 (i.e., each of the nonstructural polypeptide genes, the subgenomic promoter, and each of the structural polypeptide genes) ligated to an SspI (nucleotide position 7499)/SstI restriction fragment from TRCAT62 which contains the subgenomic promoter, 14 nucleotides of the 5' untranslated sequence of the subgenomic mRNA, the CAT gene, 62 nucleotides of Sindbis virus 3' untranslated sequence, and the Sindbis virus poly-A sequence (see Xiong et al., 1989, *Science* 243, 1188–1191).

Recombinant molecule pSV-nDiP39(3)$_{910}$ was linearized by digestion with MluI, infectious recombinant Sindbis transcripts generated with SP6 RNA Polymerase and used to infect BHK (baby hamster kidney) host cells using techniques as described in Xiong et al., ibid., thereby forming recombinant cell BHK:pSV-nDiP39(3)$_{910}$. The resulting recombinant virus vSV-nDiP39(3)$_{910}$ (also denoted 105-71.1) was cultivated for increased production and is analyzed for expression by Western blot. Immunoblot analysis indicates that P39$_{900}$ produced by this recombinant virus is capable of being selectively bound by immune sera. The infectious recombinant virus can be used as a live vaccine or in an expression system to produce *D. immitis* P39 proteins.

Example 7

This Example demonstrates the production and use of two naked nucleic acid vaccines of the present invention.

*D. immitis* P39 naked nucleic acid vaccines comprising recombinant molecules pPVXC-nDiP39(1)$_{910}$ or pPVXRC-nDiP39(1)$_{910}$ were produced as follows. Vector pRc/RSV (available from InVitrogen) was cleaved by restriction enzyme PvuII, and the 2963-base pair PvuII fragment gel purified. That fragment was self-ligated to form vector pRc/RSV(Pvu), which contains a Rous Sarcoma Virus (RSV) long terminal repeat, a multiple cloning site, a bovine growth hormone polyadenylation sequence, a bacterial origin of replication and an ampicillin resistance gene.

Expression vector PVXRC was produced by introducing a HindIII fragment containing the cytomegalovirus (CMV) intermediate early promoter and first intron (i.e., Intron A) into pRc/RSV(Pvu) that had been cleaved by HindIII. Expression vector PVXC was produced by introducing a HindIII/SspI fragment containing the CMV intermediate early promoter and first intron (i.e., Intron A) into pRc/RSV (Pvu) that had been cleaved by HindIII and NruI.

Nucleic acid molecule nDiP39(1)$_{910}$, which encodes PDiP39(1)$_{300}$, and spans from about nucleotide 216 through about nucleotide 1125 of SEQ ID NO:1, was produced by PCR amplification of that molecule from nDiP39(1)$_{1185}$ using the following primers: oligonucleotide p39pRcS (sense), having nucleic acid sequence 5' GTTGAGGATC-CGCCACCATGATAGATTTGAAGAAG 3', represented herein as SEQ ID NO:33; and oligonucleotide 39COOH (antisense) having SEQ ID NO:25 (described in Example 5). Recombinant molecule pPVXC-nDiP39(1)$_{910}$ was produced by ligating nucleic acid molecule nDiP39(1)$_{910}$ cleaved by BamHI into PVXC that had been cleaved by BamHI. Similarly, recombinant molecule pPVXRC-nDiP39(1)$_{910}$ was produced by ligating nucleic acid molecule nDiP39(1)$_{910}$ cleaved by BamHI into PVXRC that had been cleaved by BamHI.

Transfection of naked nucleic acid vaccines comprising recombinant molecules pPVXC-nDiP39(1)$_{910}$ or pPVXRC-nDiP39(1)$_{910}$ was performed by standard procedures. Briefly, six-well polystyrene tissue culture plates were seeded with about $3 \times 10^5$ cells/well in 2 ml of MEM NEAA Earle's salts (available from Irvine Scientific, Santa Ana, Calif.) with 100 mM L-glutamine, 5% FBS (complete growth media). Cells were grown to 80% confluence (about 48 hr). The recombinant molecules to be transfected were purified using Qiagen tips (available from Qiagen, Chatsworth, Calif.) per manufacturer's instructions. Using polystyrene plates, about 2 µg of each recombinant molecule was mixed with about 100 µl OptiMEM (available from Gibco BRL). About 15 µl Lipofectamine (available from Gibco BRL) was mixed with about 100 µl OptiMEM. The Lipofectamine mixture was then added to the recombinant molecule mixture and incubated at room temperature for about 30 min. After incubation, about 800 µl OptiMEM was added and the entire mixture overlaid onto the BHK cells that had been rinsed with OptiMEM. Cells were incubated at 37° C., 5% CO$_2$, 90% relative humidity. The transfection mixture was then removed and replaced with about 2 ml complete growth media.

Transfected cells were incubated at 37° C., 5% CO$_2$, 90% relative humidity for about 24 hr and harvested. The media was removed, the cells washed twice with about 2 ml PBS and scraped off the plate in about 1.5 ml PBS. The cells were pelleted by centrifugation, the PBS removed and the cells frozen.

Immunoblot analysis of cell pellets that were subjected to SDS PAGE was performed by standard procedures. Immune dog serum, prepared as described in Example 1, selectively bound to a protein of about 34 kD expressed by cells about 17 hours after transfection with naked nucleic acid vaccine pPVXC-nDiP39(1)$_{910}$.

Example 8

This Example describes the isolation and sequencing of an *O. volvulus* P39 nucleic acid molecule of the present invention.

A nucleic acid molecule comprising at least a portion of an *O. volvulus* P39 gene was produced as follows. Primers were designed using the nucleic acid sequences of certain *D. immitis* P39 nucleic acid molecules of the present invention, such as SEQ ID NO:1 and SEQ ID NO:8. Primer pairs were used to PCR amplify DNA fragments from four independent *O. volvulus* adult cDNA libraries, purchased from American Type Culture Collection (ATCC), identification number 37509 through 37512. Amplified fragments were individually screened by hybridization analysis using oligonucleotide probes corresponding to certain regions of the *D. immitis* P39 gene.

Specifically, the *D. immitis*-based primers used to identify an *O. volvulus* P39 nucleic acid molecule were as follows: oligonucleotide primer 39 Nterm, having nucleic acid sequence 5° CGCGGATCCGGTTGTGCTTCT-CAACTTTGTC 3' (corresponding to nucleic acid positions about 1 through about 21 of SEQ ID NO:1 joined to a restriction site-containing fragment indicated in bold), represented herein as SEQ ID NO:29; and Primer 391REV, having nucleic acid sequence 5' GGTTTCAGAGCAT-TGAATGC 3' (corresponding to the complement of nucleotide positions about 510 through about 529 of SEQ ID NO:1), represented herein as SEQ ID NO:30. PCR using this primer pair amplified an *O. volvulus* cDNA fragment of approximately 531 nucleotides from library number three (ATCC number 375911), referred to herein as nOvP39$_{531}$ and as Ov3. A PCR fragment of the same apparent size was also amplified in library number one (ATCC number 37509), referred to herein as Ov1. A PCR fragment of approximately 531 nucleotides was amplified from *D. immitis* nucleic acid molecule nDiP39(1)$_{1185}$ as a positive control. PCR amplification using the *D. immitis* adult female cDNA library with the 39 N term and 391 REV primers did not produce a nucleotide fragment detectable with homologous *D. immitis* nucleotide sequences.

Ov3 and Ov1 hybridized under stringent hybridization conditions with: oligonucleotide probe 116-70B, having nucleic acid sequence 5' CATTTTTATCAGGCTTCAC 3', represented herein as SEQ ID NO:31; and oligonucleotide probe 116-90A, having nucleic acid sequence 5' GATAGC-GATGATGATGAC 3', represented herein as SEQ ID NO:32. Probe 116-70B spans from about nucleotide 261 through about nucleotide 279 of SEQ ID NO:1; probe 116-90A spans from about nucleotide 345 through about nucleotide 362 of SEQ ID NO:1.

The PCR product nOvP39$_{531}$ was gel purified, cloned into the pCRII vector (available from InVitrogen) and sequenced. The nucleic acid sequence of *O. volvulus* nOvP39$_{531}$ is represented herein as SEQ ID NO:11; it is to be noted that the first about 21 nucleotides and the last about 20 nucleotides correspond to the *D. immitis*-based primers used to PCR amplify nOvP39$_{531}$.

Translation of SEQ ID NO:11 suggests that *O. volvulus* nucleic acid molecule nOvP39$_{531}$ has a structure similar to that of *D. immitis* nDiP39(1)$_{1185}$, except that nOvP39$_{531}$ is truncated at a position corresponding to about nucleotide 529 of SEQ ID NO:1. Similar to nDiP39(1)$_{1185}$, *O. volvulus* nucleic acid molecule novP39$_{531}$ includes 2 open reading frames. The open reading frame of nOvP39$_{531}$ that corresponds to the amino terminal third of nDiP39(1)$_{900}$ and nDiP39(3)$_{900}$ encodes a truncated *O. volvulus* P39 protein of about 104 amino acids, referred to herein as POvP39$_{104}$ (the deduced amino acid sequence of which is represented herein as SEQ ID NO:12), assuming an open reading frame having an initiation (start) codon spanning from about nucleotide 218 through about nucleotide 220 of SEQ ID NO:11 and ending at the last codon in nOvP39$_{531}$. This open reading frame is referred to herein as nucleic acid molecule nOvP39$_{312}$, the nucleic acid sequence of which is represented herein as SEQ ID NO:13.

It is to be noted that the open frame of nOvP39$_{531}$ including nOvP39$_{312}$ extends an additional 33 nucleotides upstream from the first ATG codon. This longer open reading frame is referred to herein as nucleic acid molecule nOvP39$_{345}$, which has a nucleic acid sequence represented herein as SEQ ID NO:14, and which encodes a protein of about 115 amino acids, denoted herein as POvP39$_{115}$, the deduced amino acid sequence of which is represented herein as SEQ ID NO:15.

The other independent open reading frame spans from about nucleotide 1 through about nucleotide 210, with a stop codon spanning from about nucleotide 211 through about nucleotide 213. This open reading frame is referred to herein as nucleic acid molecule nOvP39$_{210}$, the nucleic acid sequence of which is represented herein as SEQ ID NO:16. Nucleic acid molecule nOvP39$_{210}$ encodes a protein of about 70 amino acids, the deduced amino acid sequence of which is represented herein as SEQ ID NO:17.

The nucleic acid sequence of O. volvulus P39 nucleic acid molecule nOvP39$_{531}$ (SEQ ID NO:11) is about 89% identical to the corresponding region of D. immitis P39 nucleic acid molecule nDiP39(1)$_{1185}$ (i.e., spanning from about nucleotide 22 through about nucleotide 509 of SEQ ID NO:1). The amino acid sequence of O. volvulus P39 protein POvP39$_{70}$ (i.e., SEQ ID NO:17), encoded by nOvP39$_{210}$, is about 82% identical to the corresponding region of D. immitis P39 protein PDiP39(1)$_{72}$ (i.e., SEQ ID NO:7), encoded by nDiP39(1)$_{216}$. The amino acid sequence of O. volvulus P39 protein POvP39$_{104}$ (i.e., SEQ ID NO:12), encoded by nOvP39$_{312}$, is about 81% identical to the corresponding region of D. immitis P39 protein PDiP39(1)$_{300}$ (i.e., spanning from about amino acid 1 through about amino acid 98 of SEQ ID NO:2), encoded by nDiP39(1)$_{900}$. This high degree of conservation among the D. immitis and O. volvulus p39 genes at both the nucleic acid and deduced amino acid level, suggests a functional role for the entire gene sequence.

A homology search of the nonredundant protein sequence database was performed through the National Center for Biotechnology Information using the BLAST network. Both reading frames of nOvP39$_{531}$ were independently subjected and showed no significant homology to sequences in this database.

Example 9

This Example describes the isolation and sequencing of a B. malayi P39 nucleic acid molecule of the present invention.

A nucleic acid molecule comprising at least a portion of a B. malayi P39 gene was produced using the D. immitis P39-based primers described in Example 8 (i.e., primers having SEQ ID NO:29 and SEQ ID NO:30) to PCR amplify a B. malayi P39 nucleic acid molecule from B. malayi genomic DNA. The resulting PCR product, denoted herein as nBmP39$_{909}$ hybridized to D. immitis P39-based probes having SEQ ID NO:31 and SEQ ID NO:32, described in more detail in Example 8.

The PCR product nBmP39$_{909}$ was gel purified, cloned into the pCRII vector (available from InVitrogen) and sequenced. The nucleic acid sequence of B. malayi nBmP39$_{909}$ is represented herein as SEQ ID NO:18; it is to be noted that the first about 21 nucleotides and the last about 20 nucleotides correspond to the D. immitis-based primers used to PCR amplify nBmP39$_{909}$.

Translation of SEQ ID NO:18 and comparing that sequence with SEQ ID NO:1 suggests that B. malayi nucleic acid molecule nBmP39$_{909}$ includes an extended open reading frame similar to that of D. immitis nDiP39(3)$_{1061}$, except that nBmP39$_{909}$ is truncated at a position corresponding to about nucleotide 405 of SEQ ID NO:8 (corresponds to about nucleotide 529 of SEQ ID NO:1). B. malayi nucleic acid molecule nBmP39$_{909}$, being a genomic DNA molecule, also includes 3 introns. As such, nBmP39$_{909}$ includes (in linear, contiguous order): (a) an open reading frame spanning from about nucleotide 1 through about nucleotide 32, (b) an about 106-nucleotide intron, (c) an open reading frame spanning from about nucleotide 139 through about nucleotide 257, (d) an about 161-nucleotide intron, (e) an open reading frame spanning from about nucleotide 419 through about nucleotide 681, (f) an about 106-nucleotide intron, and (g) an open reading frame spanning from about nucleotide 788 through about nucleotide 909.

A nucleic acid molecule containing a contiguous open reading frame of about 536 nucleotides derived from nBmP39$_{909}$ is denoted herein as nBmP39$_{536}$, and has nucleic acid sequence SEQ ID NO:19. The open reading frame of nBmP39$_{536}$ that corresponds to the amino terminal third of nDiP39(1)$_{900}$ and nDiP39(3)$_{900}$, as well as to nOvP39$_{312}$, encodes a truncated B. malayi P39 protein of about 105 amino acids, referred to herein as PBmP39$_{105}$ (the deduced amino acid sequence of which is represented herein as SEQ ID NO:20), assuming an open reading frame having an initiation (start) codon spanning from about nucleotide 220 through about nucleotide 222 of SEQ ID NO:19 and ending at the last codon in nBmP39$_{536}$. This open reading frame is referred to herein as nucleic acid molecule nBmP39$_{315}$, the nucleic acid sequence of which is represented herein as SEQ ID NO:21.

Similar to D. immitis nDiP39(3)$_{1061}$, B. malayi nBmP39$_{536}$ has an uninterrupted open reading frame that extends from about nucleotide 1 through about nucleotide 534 of SEQ ID NO:19 in the same reading frame as the open reading frame for the 105-amino acid PBmP39$_{105}$ protein. The longer open reading frame is referred to herein as nucleic acid molecule nBmP39$_{534}$, which has a nucleic acid sequence represented herein as SEQ ID NO:22, and which encodes a protein of about 178 amino acids, denoted herein as PBmP39$_{178}$, the deduced amino acid sequence of which is represented herein as SEQ ID NO:23.

The nucleic acid sequence of B. malayi P39 nucleic acid molecule nBmP39$_{536}$ (SEQ ID NO:19) is about 80% identical to the corresponding region of D. immitis P39 nucleic acid molecule nDiP39(1)$_{1185}$ (i.e., spanning from about nucleotide 22 through about nucleotide 509 of SEQ ID NO:1). The amino acid sequence of B. malayi P39 protein PBmP39$_{178}$ (i.e., SEQ ID NO:23) from about amino acid 1 through about amino acid 73 is about 66% identical to the corresponding region of D. immitis P39 protein PDiP39(1)$_{72}$ (i.e., SEQ ID NO:7). The amino acid sequence of B. malayi P39 protein PBmP39$_{105}$ (i.e., SEQ ID NO:20), encoded by nBmP39$_{315}$, is about 76% identical to the corresponding region of D. immitis P39 protein PDiP39(1)$_{300}$ (i.e., spanning from about amino acid 1 through about amino acid 98 of SEQ ID NO:2). O. volvulus POvP39$_{70}$ is about 69% identical with the corresponding N-terminal region of B. malayi PBm39$_{178}$. O. volvulus POvP39$_{104}$ is about 69% identical to B. malayi PBm39$_{105}$.

Finding this degree of identity between D. immitis, O. volvulus, and B. malayi P39 nucleic acid sequences and amino acid sequences (see also Example 8) supports the ability to obtain any parasitic helminth P39 protein and nucleic acid molecule given the protein and nucleic acid sequences disclosed herein.

A homology search of the nonredundant protein sequence database was performed through the National Center for Biotechnology Information using the BLAST network. Proteins encoded by nBmP39$_{909}$ showed no significant homology to sequences in this database.

Example 10

This Example demonstrates that a recombinant P39 protein of the present invention affects *D. immitis* larval growth and survival in vivo.

*D. immitis* P39 protein PHIS-PDiP39(3)$_{300}$, produced as described in Example 6, was used in an immunization and evaluation study as follows. Two groups of mice were injected subcutaneously with the following preparations a total of two times, the injections being about 3.5 weeks apart:

7 mice received about 25 μg of PHIS-PDiP39(3)$_{300}$ protein in PBS (phosphate-buffered saline) emulsified with Hunter's Titermax™ adjuvant, from Vaxcel™, Inc. Norcross, Ga.;

6 mice were administered PBS emulsified with Titermax™ (adjuvant control group).

Two weeks after the second injection, a diffusion chamber containing 20 L3 was implanted into a sub-cutaneous pocket in each mouse using techniques similar to those described in Example 2 of the present application. Chambers were recovered from the mice after 3 weeks. Surviving larvae were counted and their lengths measured. The results are presented below:

| Group | Mice | Avg. larval recovery (std. dev.) | Avg. larval length (std. dev.) |
|---|---|---|---|
| Adjuvant control | 6 | 12.7 (2.3) | 1.344 (0.140) |
| PHIS-PDiP39(3)$_{300}$ | 7 | 12.0 (4.0) | 1.225 (0.187)** |

**Significant at P ≦0.05 by Student's one tailed t-test using worm lengths in mm.

These results indicate that growth of larvae implanted in mice administered PHIS-PDiP39(3)$_{300}$ was significantly stunted (p≦0.05) compared to growth of larvae implanted in adjuvant control mice. Larval survival (i.e., larval recovery) also appeared to be somewhat reduced in mice administered PHIS-PDiP39(3)$_{300}$ than in adjuvant control mice, but the difference was not significant at p≦0.05. As such, these results indicate a utility for P39 proteins of the present invention.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule selected from the group consisting of: (a) a nucleic acid molecule comprising a nucleic acid sequence selected from the group consisting of SEQ ID NO:1, SEQ ID NO:3, SEQ ID NO:4, SEQ ID NO:6, SEQ ID NO:8, SEQ ID NO:9, SEQ ID NO:11, SEQ ID NO:13, SEQ ID NO:14, SEQ ID NO:16, SEQ ID NO:18, SEQ ID NO:19, SEQ ID NO:21 and SEQ ID NO:22; (b) a nucleic acid molecule from a filariid nematode selected from the group consisting of Dirofilaria immitis, Onchocerca volvulus and Brugia malayi comprising a homologue of a nucleic acid molecule comprising a nucleic acid sequence selected from the group consisting of SEQ ID NO:1, SEQ ID NO:3, SEQ ID NO:4, SEQ ID NO:6, SEQ ID NO:8 and SEQ ID NO:9, wherein said homologue encodes a protein containing one or more amino acid deletions, substitutions, or insertions, wherein said protein encoded by said homologue comprises at least one epitope comprising at least 5 contiguous amino acids that elicits an immune response against a protein comprising an amino acid sequence selected from the group consisting of SEQ ID NO:2, SEQ ID NO:5, SEQ ID NO:7 and SEQ ID NO:10, wherein said homologue has at least a 15 contiguous nucleotide portion identical in sequence to a 15 contiguous nucleotide portion of a sequence selected from the group consisting of SEQ ID NO: 1, SEQ ID NO: 3, SEQ ID NO: 4, SEQ ID NO: 6, SEQ ID NO: 8 and SEQ ID NO:9; and (c) nucleic acid molecules that are fully complementary to any of said nucleic acid molecule of (a) or (b).

2. The nucleic acid molecule of claim 1, wherein said nucleic acid molecule comprises a nucleic acid sequence that encodes a protein selected from the group consisting of SEQ ID NO:2, SEQ ID NO:5, SEQ ID NO:7, SEQ ID NO:10, SEQ ID NO:12, SEQ ID NO:15, SEQ ID NO:17, SEQ ID NO:20, SEQ ID NO:23 and a homologue of said proteins containing amino acid deletions, substitutions or insertions, wherein said homologue comprises at least one epitope that elicits an antibody response against said proteins.

3. The nucleic acid molecule of claim 1, wherein said nucleic acid molecule is selected from the group consisting of: nDiP39(1)$_{1185}$ (characterized by a coding strand having the nucleic acid sequence of SEQ ID NO:1), nDiP39(1)$_{912}$ (characterized by a coding strand having the nucleic acid sequence of SEQ ID NO:4), nDiP39(1)$_{900}$ (characterized by a coding strand having the nucleic acid sequence of SEQ ID NO:3), nDiP39(1)$_{216}$ (characterized by a coding strand having the nucleic acid sequence of SEQ ID NO:6) nDiP39

(1)$_{920}$ (characterized by a coding strand having the nucleic acid sequence of nucleotides 216–1125 of SEQ ID NO:1), nDiP39(3)$_{1061}$ (characterized by a coding strand having the nucleic acid sequence of SEQ ID NO:8), nDiP39(3)$_{990}$ (characterized by a coding strand having the nucleic acid sequence of SEQ ID NO:9), niP39(3)$_{900}$ (characterized by a coding strand having the nucleic acid sequence of SEQ ID NO:3), nDiP39(3)$_{920}$ (characterized by a coding strand having the nucleic acid sequence of nucleotides 92–1001 of SEQ ID NO:8), nOvP39$_{531}$ (characterized by a coding strand having the nucleic acid sequence of SEQ ID NO:11), nOvP39$_{345}$ (characterized by a coding strand having the nucleic acid sequence of SEQ ID NO:14), nOvP393$_{312}$ (characterized by a coding strand having the nucleic acid sequence of SEQ ID NO:13), nOvP39$_{210}$ (characterized by a coding strand having the nucleic acid sequence of SEQ ID NO:16), nBmP39$_{909}$ (characterized by a coding strand having the nucleic acid sequence of SEQ ID NO.18), nBmP39$_{536}$ (characterized by a coding strand having the nucleic acid sequence of SEQ ID NO:19), nBmP39$_{534}$ (characterized by a coding strand having the nucleic acid sequence of SEQ ID NO:22), and nBmP39$_{315}$ (characterized by a coding strand having the nucleic acid sequence of SEQ ID NO:21).

4. A recombinant molecule comprising a nucleic acid molecule as set forth in claim 1 operatively linked to a transcription control sequence.

5. A recombinant virus comprising a recombinant molecule as set forth in claim 4.

6. An isolated recombinant cell comprising a nucleic acid molecule as set forth in claim 1, said cell being capable of expressing said nucleic acid molecule.

7. A method to produce a protein encoded by a nucleic acid molecule comprising a nucleic acid molecule selected from the group consisting of: (a) a nucleic acid molecule comprising a nucleic acid sequence selected from the group consisting of SEQ ID NO:1, SEQ ID NO:3, SEQ ID NO: 4, SEQ ID NO: 6, SEQ ID NO: 8, SEQ ID NO: 9, SEQ ID NO: 11, SEQ ID NO:13, SEQ ID NO:14, SEQ ID NO:16, SEQ ID NO:18, SEQ ID NO:19, SEQ ID NO:21 and SEQ ID NO:22; and (b) a nucleic acid molecule from a filariid nematode selected from the group consisting of *Dirofilaria immitis, Onchocerca volvulus* and *Brugia malayi* comprising a homologue of a nucleic acid molecule comprising a nucleic acid sequence selected from the group consisting of SEQ ID NO:1, SEQ ID NO:3, SEQ ID NO:4, SEQ ID NO:6, SEQ ID NO:8, SEQ ID NO:9, wherein said homologue encodes a protein containing one or more amino acid deletions, substitutions, or insertions, wherein said protein encoded by said homologue comprises at least one epitope comprising at least 5 contiguous amino acids that elicits an immune response against a protein comprising an amino acid sequence selected from the group consisting of SEQ ID NO:2, SEQ ID NO:5, SEQ ID NO:7 and SEQ ID NO:10, wherein said homologue has at least a 15 contiguous nucleotide portion identical in sequence to a 15 contiguous nucleotide portion of a sequence selected from the group consisting of SEQ ID NO:1, SEQ ID NO:3, SEQ ID NO:4, SEQ ID NO:6, SEQ ID NO:8 and SEQ ID NO:9.

8. The nucleic acid molecule of claim 1, wherein said nucleic acid molecule is selected from the group consisting of: (a) a nucleic acid molecule comprising a nucleic acid sequence selected from the group consisting of SEQ ID NO:1, SEQ ID NO: 3, SEQ ID NO:4, SEQ ID NO:6, SEQ ID NO8, SEQ ID NO:9, SEQ ID NO:11, SEQ ID NO:13, SEQ ID NO:14, SEQ ID NO:16, SEQ ID NO:18, SEQ ID NO:19, SEQ ID NO:21 and SEQ ID NO:22; and (b) a nucleic acid molecule comprising a nucleic acid sequence that is fully complementary to a nucleic acid sequence selected from the group consisting of SEQ ID NO:1, SEQ ID NO:3, SEQ ID NO:4, SEQ ID NO:6, SEQ ID NO:8, SEQ ID NO:9, SEQ ID NO:11, SEQ ID NO:13, SEQ ID NO:14, SEQ ID NO:16, SEQ ID NO:18, SEQ ID NO:19, SEQ ID NO:21, SEQ ID NO:22.

9. The nucleic acid molecule of claim 1, wherein said nucleic acid molecule is an oligonucleotide.

10. The nucleic acid molecule of claim 1, wherein said amino acid sequence is at least 9 contiguous amino acids.

\* \* \* \* \*

UNITED STATES PATENT AND TRADEMARK OFFICE
CERTIFICATE OF CORRECTION

PATENT NO : 6,114,142
DATED : September 5, 2000
INVENTOR(S) : Grieve et al.

It is certified that error appears in the above-identified patent and that said Letters Patent are hereby corrected as shown below:

Claim 3, column 80, line 67 through column 81, line 1, please delete "nDiP39(1)$_{920}$" and insert --nDiP39(1)$_{910}$-- therefor.

Claim 3, column 81, line 8, please delete "nDiP39(3)$_{920}$" and insert --nDiP39(3)$_{910}$-- therefor.

Signed and Sealed this

First Day of May, 2001

Attest:

NICHOLAS P. GODICI

Attesting Officer

*Acting Director of the United States Patent and Trademark Office*